(12) United States Patent
Zhao et al.

(10) Patent No.: US 9,388,382 B2
(45) Date of Patent: *Jul. 12, 2016

(54) ISOLATION OF CD14 NEGATIVE, CD45 POSITIVE AND CD117 POSITIVE EMBRYONIC-LIKE STEM CELLS FREE OF MONOCYTES FROM HUMAN UMBILICAL CORD BLOOD MONONUCLEAR CELLS

(75) Inventors: Yong Zhao, Lisle, IL (US); Theodore Mazzone, Wilmette, IL (US)

(73) Assignee: THE BOARD OF TRUSTEES OF THE UNIVERSITY OF ILLINOIS, Urbana, IL (US)

( * ) Notice: Subject to any disclaimer, the term of this patent is extended or adjusted under 35 U.S.C. 154(b) by 840 days.

This patent is subject to a terminal disclaimer.

(21) Appl. No.: 12/099,054

(22) Filed: Apr. 7, 2008

(65) Prior Publication Data

US 2009/0175832 A1 Jul. 9, 2009

Related U.S. Application Data

(63) Continuation-in-part of application No. PCT/US2006/038524, filed on Oct. 3, 2006, and a continuation-in-part of application No. PCT/US2007/022260, filed on Oct. 18, 2007.

(60) Provisional application No. 60/724,328, filed on Oct. 5, 2005, provisional application No. 60/852,901, filed on Oct. 18, 2006, provisional application No. 60/926,846, filed on Apr. 30, 2007, provisional application No. 60/927,011, filed on May 1, 2007.

(51) Int. Cl.
*C12N 5/00* (2006.01)
*C12N 5/074* (2010.01)
*A61K 35/12* (2015.01)

(52) U.S. Cl.
CPC ......... *C12N 5/0607* (2013.01); *A61K 2035/122* (2013.01)

(58) Field of Classification Search
CPC ............... C12N 5/0647; C12N 5/0663; C12N 2501/23; C12N 2506/1353; C12N 5/0675; C12N 5/0692; C12N 5/0662; C12N 5/0669; C12N 5/0678; C12N 5/0665; C12N 5/0667; C12N 5/0676; C12N 2500/90; C12N 5/0607; C12N 5/0664; C12N 5/0666; A61K 38/57; A61K 35/28; A61K 2035/124; A61K 35/50; A61K 35/51
See application file for complete search history.

(56) References Cited

U.S. PATENT DOCUMENTS

| | | |
|---|---|---|
| 4,281,061 A | 7/1981 | Zuk et al. |
| 4,362,155 A | 12/1982 | Skurkovich |
| 4,614,513 A | 9/1986 | Bensinger |
| 4,959,313 A | 9/1990 | Taketo |
| 5,286,632 A | 2/1994 | Jones |
| 5,320,962 A | 6/1994 | Stiles et al. |
| 5,342,761 A | 8/1994 | MacLeod |
| 5,618,698 A | 4/1997 | Lin |
| 5,639,275 A | 6/1997 | Baetge et al. |
| 5,670,488 A | 9/1997 | Gregory et al. |
| 5,733,541 A | 3/1998 | Taichman et al. |
| 5,981,225 A | 11/1999 | Kochanek et al. |
| 6,258,354 B1 | 7/2001 | Greenberger |
| 6,274,378 B1 | 8/2001 | Steinman et al. |
| 6,309,883 B1 | 10/2001 | Minshull et al. |
| 6,392,118 B1 | 5/2002 | Hammang et al. |
| 6,465,247 B1 | 10/2002 | Weissman et al. |
| 6,503,498 B1 | 1/2003 | Gerard et al. |
| 6,534,055 B1 | 3/2003 | June et al. |
| 6,544,780 B1 | 4/2003 | Wang |
| 6,667,391 B1 | 12/2003 | Drmanac et al. |
| 6,783,964 B2 | 8/2004 | Opara |
| 7,045,148 B2 | 5/2006 | Hariri |
| 2002/0028510 A1 | 3/2002 | Sanberg et al. |
| 2002/0160510 A1 | 10/2002 | Hariri |
| 2002/0182728 A1 | 12/2002 | Ramiya et al. |
| 2003/0180269 A1 | 9/2003 | Hariri |
| 2003/0235909 A1 | 12/2003 | Hariri et al. |

(Continued)

FOREIGN PATENT DOCUMENTS

| | | |
|---|---|---|
| WO | 90/11354 A1 | 10/1990 |
| WO | 92/03917 A1 | 3/1992 |

(Continued)

OTHER PUBLICATIONS

Mareschi et al.Isolation of human mesenchymal stem cells: bone marrow versus umbilical cord blood. Haematologica, 2001, vol. 86, pp. 1099-1100.*
Aria et al. Mesenchymal Stem Cells in Perichondrium Express Activated Leukocyte Cell Adhesion Molecule and Participate in Bone Marrow FormationJ. Exper. Med., 2002, vol. 195, pp. 1549-1563.*
Tsai et al. Isolation of human multipotent mesenchymal stem cells from second-trimester amniotic fluid using a novel two-stage culture protocol. Human Reproduction, 2004, vol. 19, pp. 1450-1456.*
In 't Anker et al. Isolation of human multipotent mesenchymal stem cells from second-trimester amniotic fluid using a novel two-stage culture protocol. Hematologica, 2003, vol. 88, pp. 845-852.*

(Continued)

*Primary Examiner* — Deborah Crouch
(74) *Attorney, Agent, or Firm* — Weisun Rao; Greenberg Traurig, LLP

(57) ABSTRACT

The present invention is related generally to embryonic-like stem cells isolated from human umbilical cord blood, designated herein as cord blood-stem cells (CB-SC's), which display the characteristics of embryonic stem cells and hematopoietic cells. These cells have the capability of proliferation and are able to differentiate to multiple types of cells. In addition, the CB-SC display low immunogenicity and immune regulation. These cells are, therefore, suitable for use in stem cell-based therapies for the treatment of diseases such as Parkinson's disease, diabetes, spinal cord damage, multiple sclerosis, cardiovascular disease, stroke and birth defects, and for preventing, treating and/or reducing an autoimmune disease in a mammalian subject.

25 Claims, 23 Drawing Sheets

(56) References Cited

U.S. PATENT DOCUMENTS

| | | |
|---|---|---|
| 2004/0022403 A1 | 2/2004 | Ballisager et al. |
| 2004/0028658 A1 | 2/2004 | Faustman |
| 2004/0028660 A1 | 2/2004 | Hariri et al. |
| 2004/0224403 A1 | 11/2004 | Bhatia |
| 2005/0118715 A1 | 6/2005 | Hariri et al. |
| 2005/0148034 A1 | 7/2005 | Hariri et al. |
| 2006/0078993 A1 | 4/2006 | Phan et al. |
| 2006/0147426 A1 | 7/2006 | Schiller et al. |
| 2007/0059824 A1 | 3/2007 | Zhao et al. |
| 2008/0159998 A1 | 7/2008 | Ichim |
| 2008/0293135 A1 | 11/2008 | Orr et al. |
| 2009/0175832 A1* | 7/2009 | Zhao et al. .................... 424/93.7 |
| 2010/0129440 A1 | 5/2010 | Zhao et al. |

FOREIGN PATENT DOCUMENTS

| | | |
|---|---|---|
| WO | 9218615 A1 | 10/1992 |
| WO | 93/04169 A1 | 3/1993 |
| WO | 9312805 A1 | 7/1993 |
| WO | 95/17911 A1 | 7/1995 |
| WO | 9920741 A1 | 4/1999 |
| WO | 9961584 A1 | 12/1999 |
| WO | 0162895 A2 | 8/2001 |
| WO | WO02/076501 | 10/2002 |
| WO | 02097067 A1 | 12/2002 |
| WO | WO 03/055989 | 7/2003 |
| WO | WO03/068937 | 8/2003 |
| WO | 03083092 A1 | 10/2003 |
| WO | WO2005097979 | * 10/2005 |
| WO | WO 2006/044842 | 4/2006 |
| WO | WO 2007/044314 | 4/2007 |
| WO | 2008048671 | 4/2008 |

OTHER PUBLICATIONS

Lee et al. Isolation of Mesenchymal Stem Cells from Cryopreserved Human Umbilical Cord BloodInternational Journal of Hematology, 2005, vol. 81, 126-130.*
Dominici et al.Minimal criteria for defining multipotent mesenchymal stromal cells. The International Society for Cellular Therapy position statement Cytotherapy, 2006, vol. 8, pp. 315-317.*
Rogers et al. Identification and analysis of in vitro cultured CD45-positive cells capable of multi-lineage differentiation Experimental Cell Research, 2007, vol. 313, pp. 1839-1852.*
Thermo Scientific Catalog. Nunc Nalgene T25 Flasks Untreated. 2014, p. 1.*
Lee et al. Isolation of multipotent mesenchymal stem cells from umbilical cord blood. Blood, 2004, vol. 103, pp. 1669-1675.*
Tilden et al. A comparison of pge, effects on human suppressor cell function and on Interleukin 2 function. J. Immunol., 1982, vol. 129, pp. 2469-2473.*
Alberts, Molecular Biology of the Cell, 2th Edition, Alberts, B et al, ed., Garland Publishing Inc, 1989.*
Thorsson et al. New Eng. J Med., 1977, vol. 297, pp. 909-912.*
Ham, R. Clonal Growth of Mammalian Cells in a Chemically Defined, Synthetic Medium. PNAS, 1965, vol. 53, pp. 288-293.*
UCLA School of Medicine. Virology Core Lab Protocol, Monocyte Separation Protocol, Feb. 24, 2009.*
Birkmann et la., "Effects of Recombinant Human Thrombopoietin Alone and in Combination With Erythropoietin and Early-Acting Cytokines on Human Mobilized Purified CD34+ Progenitor Cells Cultured in Serum-Depleted Medium", Stem Cells, vol. 15, pp. 18-32, 1997.
Bjorklund, A. et al., "Cell Replacement Therapies for Central Nervous System Disorders", Nature Neuroscience, vol. 3, pp. 537-544, 2000.
Buzanska, L. et al., "Human Cord Blood-Derived Cells Attain Neuronal and Glial Features In Vitro", J. Cell Sci., vol. 115, pp. 2131-2138, 2002.
Carpenter, G., "EGF: New Tricks for an Old Growth Factor", Current Opinion in Cell Biology, vol. 5, pp. 261-264, 1993.

Chang, C-J et al., "Placenta-Derived Multipotent Cells Exhibit Immunosuppressive Properties That Are Enhanced in the Presence of Interferon-?", Stem Cells, vol. 24, pp. 2466-2477, 2006.
Djouad, F. et al., "Immunosuppressive Effect of Mesenchymal Stem Cells Favors Tumor Growth in Allogeneic Animals", Blood, vol. 102, pp. 3837-3844, 2003.
Donovan, P.J. et al., "The End of the Beginning for Pluripotent Stem Cells", Nature, vol. 414, pp. 92-97, 2001.
Ellis, M.H. et al., "The Regulation of Megakaryocytopoiesis", Blood Reviews, vol. 9, pp. 1-6, 1995.
Encinas, M. et al., "Sequential Treatment of SH-SY5Y Cells With Retinoic Acid and Brain-Derived Neurotrophic Factor Gives Rise to Fully Differentiated, Neurotrophic Factor-Dependent, Human Neuron-Like Cells", Journal of Neurochemistry, vol. 75, pp. 991-1003, 2000.
Gluckman, E. et al., "Hematopoietic Reconstitution in a Patient With Fanconi's Anemia B Means of Umbilical-Cord Blood From an HLA-Identical Sibling", NEJM, vol. 321, pp. 1174-1178, 1989.
Gordon, S. et al., "Molecular Immunobiology of Macrophages: Recent Progress", Current Opinion in Immunology, vol. 7, pp. 24-33, 1995.
Gotze, K. et al., "Flt3high and Flt3low CD34+ Progenitor Cells Isolated From Human Bone Marrow Are Functionally Distinct", Blood, vol. 91, pp. 1947-1958, 1998.
Grage-Griebenow, E. et al., "Heterogeneity of Human Peripheral Blood Monocyte Subsets", Journal of Leukocyte Biology, vol. 69, pp. 11-20, 2001.
Graversen, J.H. et al., "Molecules in Focus CD163: A Signal Receptor Scavenging Haptoglobin-Hemoglobin Complexes From Plasma", J. Biochem. & Cell Biol., vol. 34, pp. 309-314, 2002.
Griffith, L. G. et al., "Tissue Engineering-Current Challenges and Expanding Opportunities", Science, vol. 295, pp. 1009-1014, 2002.
Gu, D. et al., "Epithelial Cell Proliferation and Islet Neogenesis in IFN-g Transgenic Mice", Development, vol. 118, pp. 33-46, 1993.
Hamazaki, T. et al., "Hepatic Maturation in Differentiating Embryonic Stem Cells in Vitro", FEBS Letters, vol. 497, pp. 15-19, 2001.
Hamid, M. et al., "Comparative Functional Study of Clonal Insulin-Secreting Cells Cultured in Five Commercially Available Tissue Culture Media", Cell Transplantation, vol. 10, pp. 153-159, 2001.
Huss, R., "Isolation of Primary and Immortalized CD34 Hematopoietic and Mesenchymal Stem Cells From Various Sources", Stem Cells, vol. 18, pp. 1-9, 2000.
Ishikawa, F. et al., "Tranplanted Human Cord Blood Cells Give Rise to Hepatocytes in Engrafted Mice", Annals NY Acad Sci., vol. 996, pp. 174-185, 2003.
Jacovina, A.T. et al., "Neuritogenesis and the Nerve Growth Factor-Induced Differentiation of PC-12 Cells Requires Annexin II-Mediated Plasmin Generation", The Journal of Biological Chemistry, vol. 276, pp. 49350-49358, 2001.
Jiang, Y. et al., "Pluripotency of Mesenchymal Stem Cells Derived From Adult Marrow", Nature, vol. 418, pp. 41-49, 2002.
Karkkainen, M. et al., "Lymphatic Endothelium: A New Frontier of Metastasis Research", Nature Cell Biology, vol. 4, pp. E2-E5, 2002.
Korbling, M. et al., "Hepatocytes and Epithelial Cells of Donor Origin in Recipients of Peripheral-Blood Stem Cells", N Engl J Med, vol. 346, pp. 738-746, 2002.
Lagasse, E. et al., "Purified Hematopoietic Stem Cells Differentiate Into Hepatocytes In Vivo", Nature Medicine, vol. 6, pp. 1229-1234, 2000.
Lederman, S. et al., "Antigen Presenting Cells Integrate Opposing Signals From CD4+ and CD8+ Regulatory T Lymphocytes to Arbitrate the Outcomes of Immune Responses", vol. 60, pp. 553-561, 1999.
Lee, O.K. et al., "Isolation of Multipotent Mesenchymal Stem Cells From umbilical Cord Blood", Blood, vol. 103, pp. 1669-1675, 2004.
Lee, M.W. et al., "Mesenchymal Stem Cells From Cryopreserved Human Umbilical Cord Blood", Biochem Biophy Res Comm, vol. 320, pp. 273-278, 2004.
Li, J. et al., "The End Is Just the Beginning: Megakaryocyte Apoptosis and Platelet Release", International Journal of Hematology, vol. 74, pp. 365-374, 2001.
Lovell-Badge, R., "The Future for Stem Cell Research", Nature, vol. 414, pp. 88-91, 2001.

(56) References Cited

OTHER PUBLICATIONS

Lumelsky, N. et al., "Differentiation of Embryonic Stem Cells to Insulin-Secreting Structures Similar to Pancreatic Islets", Science, vol. 292, pp. 1389-1394, 2001.
Mayani, H. et al., "Biology of Human Umbilical Cord Blood-Derived Hematopoietic Stem/Progenitor Cells", Stem Cells, vol. 16, pp. 153-165, 1998.
McAllister, A.K., "Neurotrophins and Neuronal Differentiation in the Central Nervous System", CMLS, Cell. Mol. Life Sci., vol. 58, pp. 1054-1060, 2001.
Nakabo, Y. et al., "Lysis of Leukemic Cells by Human Macrophages: Inhibition by 4-(2-Aminoethyl)-Benzenesulfonyl Fluoride (AEBSF), A Serine Protease Inhibitor", Journal of Leukocyte, vol. 60, pp. 328-336, 1996.
Orlic, D. et al., "Bone Marrow Cells Regenerate Infarcted Myocardium", Nature, vol. 410, pp. 701-705, 2001.
Pittenger, M.F. et al., "Multilineage Potential of Adult Human Mesenchymal Stem Cells", Nature, vol. 284, pp. 143-147, 1999.
Randall, T.D. et al., "Characterization of a Population of Cells in the Bone Marrow That Phenotypically Mimics Hematopoietic Stem Cells: Resting Stem Cells or Mystery Population", Stem Cells, vol. 16, pp. 38-48, 1998.
Ruck, P. et al., "Hepatic Stem-Like Cells in Hepatoblastoma: Expression of Cytokeratin 7, Albumin and Oval Cell Associated Antigens Detected by OV-1 and OV-6", Histopathology, vol. 31, pp. 324-329, 1997.
Ryffel, B. et al., "Differentiation of Human T-Lymphoid Leukemia Cells Into Cells That Have a Suppressor Phenotype Is Induced by Phorbol 12-Myristate 13-Acetate", Proc. Natl. Acad. Sci. USA, vol. 79, pp. 7336-7340, 1982.
Schmidt, C. et al., "Scatter Factor/Hepatocyte Growth Factor Is Essential for Liver Development", Nature, vol. 373, pp. 699-702, 1995.
Schuit, F. et al., "Metabolic Fate of Glucose in Purified Islet Cells", The Journal of Biological Chemistry, vol. 272, pp. 18572-18579, 1997.
Sorg, R.V. et al., "Phenotypic and Functional Comparison of Monocytes From Cord Blood and Granulocyte Colony-Stimulating Factor-Mobilized Apheresis Product", Experimental Hematology, vol. 29, pp. 1289-1294, 2001.
Swanson, J.A. et al., "Cellular Dimensions Affecting the Nucleocytoplasmic vol. Ratio", The Journal of Cell Biology, vol. 115, pp. 941-948, 1991.
Terada, N. et al., "Bone Marrow Cells Adopt the Phenotype of Other Cells by Spontoneous Cell Fusion", Nature, vol. 416, pp. 542-545, 2002.
Tontonoz, P. et al., "PPAR? Promotes Monocyte/Macrophage Differentiation and Uptake of Oxidized LDL", Cell, v. 93, pp. 241-252, 1998.
Tseng, S.C. et al., "Correlation of Specific Keratins With Different types of Epithelial Differentiation: Monoclonal Antibody Studies", Cell, vol. 30, pp. 361-372, 1982.
Vadiveloo, P.K., "Macrophages-Proliferation, Activation, and Cell Cycle Proteins", Journal of Leukocyte Biology, vol. 66, pp. 579-582, 1999.
Weissman, "Stem Cells—Scientific, Medical, and Political Issues", N Engl J Med, vol. 346, pp. 1576-1579, 2002.
Ying, Q-L et al., "Changing Potency by Spontaneous Fusion", Nature, vol. 416, pp. 545-548, 2002.
Zhou, L-J et al., " CD14+ Blood Monocytes Can Differentiate Into functionally Mature CD83 Dendritic Cells", Proc. Natl. Acad. Sci. USA, vol. 93, pp. 2588-2592, 1996.
Rehman, J. et al., "Peripheral Blood Endothelial Progenitor Cells Are Derived From Monocyte/Macrophages and Secrete Angiogenic Growth Factors", Circulation, vol. 107 pp. 1164-1169, 2003.
Written Opinion of International Searching Authority for PCT/US2006/038524, dated Jun. 25, 2007 (4 pages).
International Preliminary Report on Patentability for PCT/US2007/022260, dated Apr. 30, 2009 (9 pages).
Written Opinion of International Searching Authority for PCT/US2007/022260, dated Mar. 17, 2008 (7 pages).
Written Opinion of International Searching Authority for PCT/US2010/059522, dated Apr. 28, 2011 (5 pages).
Adamson, "Cord Blood Stem Cell Banking and Transplantation. Hematopoietic Stem Cells", Stem Cells, vol. 15, Suppl. 1, pp. 57-61, 1997.
Cairo et al., "Placental and/or Umbilical Cord Blood: An Alternative Source of Hematopoietic Stem Cells for Transplantation", Blood, vol. 90, pp. 4665-4678, 1997.
Harris, D.T., "Experience in Autologous and Allogeneic Cord Blood Banking", J. Hematotherapy, vol. 5, pp. 123-128, 1996.
Holz, G., "New Insights Concerning the Glucose-Dependent Insulin Secretagogue Action of Glucagon-Like Peptide-1 in Pancreatic β-Cells", Horm Metab Res, v. 36, pp. 787-794, 2004.
Hunnestad et al., "Thrombopoietin Combined With Early-Acting Growth Factors Effectively Expands Human Hematopoietic Progenitor Cells in Vitro", Stem Cells, vol. 17, pp. 31-38, 1999.
Kucia et al., "Morphological and Molecular Characterization of Novel Population of CXCR4+ SSEA-4+, Oct-4+ Very Small Embryonic-Like Cell Purified From Human Cord Blood—Preliminary Report", Leukemia, vol. 21, pp. 297-303, 2007.
Rasmusson, "Immune Modulation by Mesenchymal Stem Cells", Experimental Cell Research, v. 312, pp. 2169-2179, 2006.
Romagnani et al., "CD14+CD341$^{low}$ Cells With Stem Cell Phenotypic and Functional Features Are the Major Source of Circulating Endothelial Progenitors", Circulation Research, v. 97, pp. 314-322, 2005.
Ruhnke et al., "Differentiation of in Vitro-Modified Human Peripheral Blood Monocytes Into Hepatocyte-Like and Pancreatic Islet-Like Cells", Gastroenterology, v. 128, pp. 1774-1786, 2005.
Sirchia, G. et al., "Placental/Umbilical Cord Blood Transplantation", Hematologica, vol. 84, pp. 738-747, 1999.
Yoshida et al., "Human Cord Blood-Derived Cells Generate Insulin-Producing Cells In Vivo", Stem Cells, vol. 23, No. 9, pp. 1409-1416, 2005.
Zhao et al., "Identification of Stem Cells From Human Umbilical Cord Blood With Embryonic and Hematopoietic Characteristics", Experimental Cell Research, v. 312, pp. 2454-2464, 2006.
Zhao, Y. et al., "A Unique Human Blood-Derived Cell Population Displays High Potential for Producing Insulin", Biochemical and Biophysical Research Communications, vol. 360, pp. 205-211, 2007.
Zhao, Y. et al., "Immune Regulation of T Lymphocyte by a Newly Characterized Human Umbilical Cord Blood Stem Cell", Immunology Letters, vol. 108, pp. 78-87, 2007.
Zhao, Y. et al., "Human Unbilical Cord Blood-Derived F-Macrophages Retain PluripotentialityAfter Thrombopoietin Expansion", Experimental Cell Research, vol. 310, pp. 311-318, 2005.
Zhao, Y. et al., "A Human Peripheral Blood Monocyte-Derived Subset Acts As Pluripotent Stem Cells", PNAS, vol. 100, pp. 2426-2431, 2003.
Birkmann, J. et al., "Effects of Recombinant Human Thrombopoietin Alone and in Combination With Erythropietin and Early-Acting Cytokines on Human Mobilized Purified CD34 Progenitor Cells Cultured in Serum-Depleted Medium", Stem Cells, vol. 15, pp. 18-32, 1997.
Graversen, J. et al., "Molecules in Focus CD163: A Signal Receptor Scavenging Haptoglobin-Hemoglobin Complexes From Plasma", The International Journal of Biochemistry & Cell Biology, vol. 34, pp. 309-314, 2002.
Huss, R., "Isolation of Primary and Immortalized CD34— Hematopoietic and Mesenchymal Stem Cells From Various Sources", Stem Cells, vol. 18, pp. 1-9, 2000.
Mayani, H, "Biology of Human Umbilical Cord Blood-Derived Hematopoietic Stem/Progenitor Cells", Stem Cells, vol. 16, pp. 153-165, 1998.
Zhu, X. et al., "Severe Block in Processing of Proinsulin to Insulin Accompanied by Elevation of Des-64,65 Proinsulin Intermediates in Islets of Mice Lacking Prohormone Convertase 1/3", PNAS, vol. 99, pp. 10299-10304, 2002.
Zucker-Franklin, D., Megakaryocyte and Platelet Structure in Thrombocytopoiesis: The Effect of Cytokines, Stem Cells, vol. 14 (Suppl 1), pp. 1-17, 1996.

(56) References Cited

OTHER PUBLICATIONS

Michalopoulos, G.K. et al., "Liver Regeneration", Science, vol. 276, p. 60, 1997.
Abuljadayel et al. Curr Med Res Opin 2003; 19:355-75.
Carlin et al. Rep rod Bioi Endocrinol Feb. 2006;4:8, 1-13.
De Mulder et al. Clin Exp Immunol 1983; 54:681-8.
European Office Action for Application No. 06825367.3, dated Jul. 5, 2012. (4 pages).
Galic et al. PNAS 2006; 103:11742-7.
GeneTex, Inc. 2010.
Preffer et al. Stem Cells 2002;20:417-27.
Price et al. Stem Cells Dev 2006; 15:507-22.
Rutella et al. J Immunol 2003; 171:2977-88.
Xiao et al., Stem Cell Develop 2005; 14:722-33.
International Preliminary Report on Patentability for Application No. PCT/US2010/059522, dated Jun. 21, 2012 (7 pages).
Silani et al., Stem-cell therapy for amyotrophic lateral sclerosis. Lancet. Jul. 10-16, 2004;364(9429):200-2.
Sutherland et al., Characterization and partial purification of human marrow cells capable of initiating long-term hematopoiesis in vitro. Blood. Oct. 1989;74(5):1563-70.
Taneera et al., Failure of transplanted bone marrow cells to adopt a pancreatic beta-cell fate. Diabetes. Feb. 2006;55(2):290-6.
Taylor et al., Curbing activation: proprotein convertases in homeostasis and pathology. FASEB J. Jul. 2003;17(10):1215-27.
Thorens, B., GLUT2 in pancreatic and extra-pancreatic gluco-detection (review). Mol Membr Biol. Oct.-Dec. 2001;18(4):265-73.
Underhill et al., The Toll-like receptor 2 is recruited to macrophage phagosomes and discriminates between pathogens. Nature. Oct. 21, 1999;401(6755):811-5.
Vats et al., Stem cells. Lancet. Aug. 13-19, 2005;366(9485):592-602.
Wagers et al., Plasticity of adult stem cells. Cell. Mar. 5, 2004;116(5):639-48.
Wilan et al., Chasing a cellular fountain of youth. Nat Biotechnol. Jul. 2005;23(7):807-15.
Yamada et al., Relationship between beta cell mass of NOD donors and diabetes development of NOD-scid recipients in adoptive transfer system. Ann N Y Acad Sci. Nov. 2003;1005:211-4.
Yanagi et al., Performance of a new hybrid artificial liver support system using hepatocytes entrapped within a hydrogel. ASAIO Trans. Jul.-Sep. 1989;35(3):570-2.
Yu et al., Mid-trimester fetal blood-derived adherent cells share characteristics similar to mesenchymal stem cells but full-term umbilical cord blood does not. Br J Haematol. Mar. 2004;124(5):666-75.
Zalzman et al., Reversal of hyperglycemia in mice by using human expandable insulin-producing cells differentiated from fetal liver progenitor cells. Proc Natl Acad Sci U S A. Jun. 10, 2003;100(12):7253-8. Epub May 19, 2003.
Zalzman et al., Differentiation of human liver-derived, insulin-producing cells toward the beta-cell phenotype. Diabetes. Sep. 2005;54(9):2568-75.
Ziche et al., Nitric oxide mediates angiogenesis in vivo and endothelial cell growth and migration in vitro promoted by substance P. J Clin Invest. Nov. 1994;94(5):2036-44.
Cai et al., Microencapsulated hepatocytes for bioartificial liver support. Artif Organs. Oct. 1988;12(5):388-93.
Chang, TM, Artificial liver support based on artificial cells with emphasis on encapsulated hepatocytes. Artif Organs. Feb. 1992;16(1):71-4.
Chang et al., The in vivo delivery of heterologous proteins by microencapsulated recombinant cells. Trends Biotechnol. Feb. 1999;17(2):78-83.
Choileain et al., Regulatory T-cells and autoimmunity. J Surg Res. Jan. 2006;130(1):124-35. Epub Sep. 8, 2005.
Cicuttini et al., Characterization of CD34+HLA-DR-CD38+ and CD34+HLA-DR-CD38− progenitor cells from human umbilical cord blood. Growth Factors. 1994;10(2):127-34.
Craig et al., CD45 isoform expression on human haemopoietic cells at different stages of development. Br J Haematol. Sep. 1994;88(1):24-30.

da Silva Meirelles et al., Mesenchymal stem cells reside in virtually all post-natal organs and tissues. J Cell Sci. Jun. 1, 2006;119(Pt 11):2204-13. Epub May 9, 2006.
Del Prete et al., Human IL-10 is produced by both type 1 helper (Th1) and type 2 helper (Th2) T cell clones and inhibits their antigen-specific proliferation and cytokine production. J Immunol. Jan. 15, 1993;150(2):353-60.
Dennis et al., 'Ethical' routes to stem cells highlight political divide. Nature. Oct. 20, 2005;437(7062):1076-7.
Docherty et al., Carboxypeptidase activity in the insulin secretory granule. FEBS Lett. Oct. 3, 1983;162(1):137-41.
Drukker et al., Characterization of the expression of MHC proteins in human embryonic stem cells. Proc Natl Acad Sci U S A. Jul. 23, 2002;99(15):9864-9. Epub Jul. 11, 2002.
Edlund, H, Pancreatic organogenesis—developmental mechanisms and implications for therapy. Nat Rev Genet. Jul. 2002;3(7):524-32.
Evans, M., Ethical sourcing of human embryonic stem cells—rational solutions? Nat Rev Mol Cell Biol. Aug. 2005;6(8):663-7.
Gang et al., In vitro mesengenic potential of human umbilical cord blood-derived mesenchymal stem cells. Biochem Biophys Res Commun. Aug. 13, 2004;321(1):102-8.
Grove et al., Plasticity of bone marrow-derived stem cells. Stem Cells. 2004;22(4):487-500.
Hadkar et al., Carboxypeptidase-mediated enhancement of nitric oxide production in rat lungs and microvascular endothelial cells. Am J Physiol Lung Cell Mol Physiol. Jul. 2004;287(1):L35-45. Epub Feb. 20, 2004.
Hawrylowicz et al., Potential role of interleukin-10-secreting regulatory T cells in allergy and asthma. Nat Rev Immunol. Apr. 2005;5(4):271-83.
Hawrylowicz, CM, Regulatory T cells and IL-10 in allergic inflammation. J Exp Med. Dec. 5, 2005;202(11):1459-63.
Hayek et al., Experimental transplantation of human fetal and adult pancreatic islets. J Clin Endocrinol Metab. Aug. 1997;82(8):2471-5.
Hoffman et al., Characterization and culture of human embryonic stem cells. Nat Biotechnol. Jun. 2005;23(6):699-708.
Hori et al., Growth inhibitors promote differentiation of insulin-producing tissue from embryonic stem cells. Proc Natl Acad Sci U S A. Dec. 10, 2002;99(25):16105-10. Epub Nov. 19, 2002.
Hori et al., Differentiation of insulin-producing cells from human neural progenitor cells. PLoS Med. Apr. 2005;2(4):e103. Epub Apr. 26, 2005.
Hussain et al., Stem-cell therapy for diabetes mellitus. Lancet. Jul. 10-16, 2004;364(9429):203-5.
Ianus et al., In vivo derivation of glucose-competent pancreatic endocrine cells from bone marrow without evidence of cell fusion. J Clin Invest. Mar. 2003;111(6):843-50.
Ingram et al., Identification of a novel hierarchy of endothelial progenitor cells using human peripheral and umbilical cord blood. Blood. Nov. 1, 2004;104(9):2752-60. Epub Jun. 29, 2004.
Kayali et al., The stromal cell-derived factor-1alpha/CXCR4 ligand-receptor axis is critical for progenitor survival and migration in the pancreas. J Cell Biol. Nov. 24, 2003;163(4):859-69.
Klimanskaya et al., Human embryonic stem cells derived without feeder cells. Lancet. May 7-13, 2005;365(9471):1636-41.
Kogler et al., A new human somatic stem cell from placental cord blood with intrinsic pluripotent differentiation potential. J Exp Med. Jul. 19, 2004;200(2):123-35.
Kuwana et al., Human circulating CD14+ monocytes as a source of progenitors that exhibit mesenchymal cell differentiation. J Leukoc Biol. Nov. 2003;74(5):833-45. Epub Jul. 22, 2003.
Lansdorp et al., Long-term erythropoiesis from constant numbers of CD34+ cells in serum-free cultures initiated with highly purified progenitor cells from human bone marrow. J Exp Med. Jun. 1, 1992;175(6):1501-9.
Lapidot et al., How do stem cells find their way home? Blood. Sep. 15, 2005;106(6):1901-10. Epub May 12, 2005.
Lechner et al., No evidence for significant transdifferentiation of bone marrow into pancreatic beta-cells in vivo. Diabetes. Mar. 2004;53(3):616-23.
Matsuoka et al., The MafA transcription factor appears to be responsible for tissue-specific expression of insulin. Proc Natl Acad Sci U S A. Mar. 2, 2004;101(9):2930-3. Epub Feb. 18, 2004.

(56) References Cited

OTHER PUBLICATIONS

Matthew et al., Microencapsulated hepatocytes. Prospects for extracorporeal liver support. ASAIO Trans. Jul.-Sep. 1991;37(3):M328-30.
McGuckin et al., Production of stem cells with embryonic characteristics from human umbilical cord blood. Cell Prolif. Aug. 2005;38(4):245-55.
Melton et al., Altered nuclear transfer in stem-cell research—a flawed proposal. N Engl J Med. Dec. 30, 2004;351(27):2791-2.
Miyazaki et al., Regulated expression of pdx-1 promotes in vitro differentiation of insulin-producing cells from embryonic stem cells. Diabetes. Apr. 2004;53(4):1030-7.
Moore et al., Interleukin-10. Annu Rev Immunol. 1993;11:165-90.
Mousa et al., Subcellular pathways of beta-endorphin synthesis, processing, and release from immunocytes in inflammatory pain. Endocrinology. Mar. 2004;145(3):1331-41. Epub Nov. 20, 2003.
Orkin, SH, Chipping away at the embryonic stem cell network. Cell. Sep. 23, 2005;122(6):828-30.
Paust et al., Regulatory T cells and autoimmune disease. Immunol Rev. Apr. 2005;204:195-207.
Peterson, D.A, Umbilical cord blood cells and brain stroke injury: bringing in fresh blood to address an old problem. J Clin Invest. Aug. 2004;114(3):312-4.
Randolph et al., Cd4+Cd25+ regulatory T cells and their therapeutic potential. Annu Rev Med. 2006;57:381-402.
Rice et al., Adult stem cells—reprogramming neurological repair? Lancet. Jul. 10-16, 2004;364(9429):193-9.
Richards et al., Human feeders support prolonged undifferentiated growth of human inner cell masses and embryonic stem cells. Nat Biotechnol. Sep. 2002;20(9):933-6. Epub Aug. 5, 2002.
Sanberg et al., Umbilical cord blood-derived stem cells and brain repair. Ann N Y Acad Sci. May 2005;1049:67-83.
Sancho et al., CD69 is an immunoregulatory molecule induced following activation. Trends Immunol. Mar. 2005;26(3):136-40.
Segev et al., Differentiation of human embryonic stem cells into insulin-producing clusters.Stem Cells. 2004;22(3):265-74.
Shea et al., DNA delivery from polymer matrices for tissue engineering. Nat Biotechnol. Jun. 1999;17(6):551-4.
Shibasaki et al., Integration of ATP, cAMP, and Ca2+ signals in insulin granule exocytosis. Diabetes. Dec. 2004;53 Suppl 3:S59-62.
[No Author Listed] GenBank Accession No. AAO65969. Updated Mar. 24, 2003, 1 page.
[No Author Listed] GenBank Accession No. AF005058. Updated Sep. 21, 2000, 5 pages.
[No Author Listed] GenBank Accession No. CAA83435. Updated Apr. 18, 2005, 2 pages.
[No Author Listed] GenBank Accession No. CAG46675. Updated Jun. 29, 2004, 2 pages.
[No Author Listed] GenBank Accession No. CAG46893. Updated Jun. 29, 2004, 2 pages.
[No Author Listed] GenBank Accession No. EAW94647. Updated Dec. 18, 2006, 2 pages.
[No Author Listed] GenBank Accession No. M27394. Updated Jul. 15, 1993, 2 pages.
[No Author Listed] GenBank Accession No. M38690. Updated Nov. 11, 1995, 2 pages.
[No Author Listed] GenBank Accession No. NM_000222. Updated Jun. 21, 2009, 11 pages.
[No Author Listed] GenBank Accession No. NM_000632. Updated Apr. 6, 2008, 11 pages.
[No Author Listed] GenBank Accession No. NM_000887. Updated Apr. 6, 2008, 12 pages.
[No Author Listed] GenBank Accession No. NM_001769. Updated May 24, 2009, 7 pages.
[No Author Listed] GenBank Accession No. NM_002045. Updated Sep. 28, 2008, 7 pages.
[No Author Listed] GenBank Accession No. NM_002473. Updated Apr. 6, 2008, 15 pages.
[No Author Listed] GenBank Accession No. NM_002701. Updated Apr. 6, 2008, 6 pages.
[No Author Listed] GenBank Accession No. NM_002838. Updated May 10, 2009, 12 pages.
[No Author Listed] GenBank Accession No. NM_002851. Updated Jun. 7, 2009, 14 pages.
[No Author Listed] GenBank Accession No. NM_003413. Updated Dec. 21, 2008, 6 pages.
[No Author Listed] GenBank Accession No. NM_004426. Updated Feb. 1, 2009, 9 pages.
[No Author Listed] GenBank Accession No. NM_005397. Updated May 10, 2009, 9 pages.
[No Author Listed] GenBank Accession No. NM_007129. Updated May 10, 2009, 7 pages.
[No Author Listed] GenBank Accession No. NM_024504. Updated Mar. 27, 2008, 5 pages.
[No Author Listed] GenBank Accession No. NM_024865. Updated Feb. 11, 2008, 7 pages.
[No Author Listed] GenBank Accession No. NM_032805.1. Updated Feb. 10, 2008, 4 pages.
[No Author Listed] GenBank Accession No. NM_001040021. Updated Apr. 6, 2008, 6 pages.
[No Author Listed] GenBank Accession No. NP_001618. Updated Apr. 18, 2005, 2 pages.
[No Author Listed] GenBank Accession No. NP_005202. Updated Mar. 30, 2008, 4 pages.
[No Author Listed] GenBank Accession No. NP_057173.1. Updated Nov. 17, 2006, 2 pages.
[No Author Listed] GenBank Accession No. NP_079141. Updated Feb. 11, 2008, 3 pages.
[No Author Listed] GenBank Accession No. NP_116194.1. Updated Feb. 10, 2008, 2 pages.
[No Author Listed] GenBank Accession No. NP_001020329. Updated Mar. 16, 2008, 3 pages.
[No Author Listed] GenBank Accession No. P08571. Updated Dec. 4, 2007, 7 pages.
[No Author Listed] GenBank Accession No. P08575. Updated Jun. 16, 2009, 24 pages.
[No Author Listed] GenBank Accession No. P10721. Updated Jun. 16, 2009, 24 pages.
[No Author Listed] GenBank Accession No. P28906. Updated Mar. 18, 2008, 6 pages.
[No Author Listed] GenBank Accession No. Q01860. Updated Mar. 18, 2008, 5 pages.
[No Author Listed] GenBank Accession No. Z11898. Updated Apr. 18, 2005, 3 pages.
[No Author Listed] GenBank Accession No. Z31560. Updated Apr. 18, 2005, 2 pages.
Aoki et al., Derivation of functional endothelial progenitor cells from human umbilical cord blood mononuclear cells isolated by a novel cell filtration device. Stem Cells. 2004;22(6):994-1002.
Andressen et al., Beta1 integrin deficiency impairs migration and differentiation of mouse embryonic stem cell derived neurons. Neurosci Lett. Jul. 31, 1998;251(3):165-8.
Baal et al., Expression of transcription factor Oct-4 and other embryonic genes in CD133 positive cells from human umbilical cord blood. Thromb Haemost. Oct. 2004;92(4):767-75.
Ballen, K.K., New trends in umbilical cord blood transplantation. Blood. May 15, 2005;105(10):3786-92. Epub Jan. 27, 2005.
Bally-Cuif et al., Induction and patterning of neuronal development, and its connection to cell cycle control. Curr Opin Neurobiol. Feb. 2003;13(1):16-25.
Baron, M, Induction of embryonic hematopoietic and endothelial stem/progenitor cells by hedgehog-mediated signals. Differentiation. Oct. 2001;68(4-5):175-85.
Battaglia et al., IL-10-producing T regulatory type 1 cells and oral tolerance. Ann N Y Acad Sci. Dec. 2004;1029:142-53.
Bieback et al., Critical parameters for the isolation of mesenchymal stem cells from umbilical cord blood. Stem Cells. 2004;22(4):625-34.
Bonadio et al., Localized, direct plasmid gene delivery in vivo: prolonged therapy results in reproducible tissue regeneration. Nat Med. Jul. 1999;5(7):753-9.
Bonde et al., Recent advances in hematopoietic stem cell biology. Curr Opin Hematol. Nov. 2004;11(6):392-8.

(56) References Cited

OTHER PUBLICATIONS

Bradley et al., Stem cell medicine encounters the immune system. Nat Rev Immunol. Nov. 2002;2(11):859-71.

Brolen et al., Signals from the embryonic mouse pancreas induce differentiation of human embryonic stem cells into insulin-producing beta-cell-like cells. Diabetes. Oct. 2005;54(10):2867-74.

* cited by examiner

FIG. 1
A
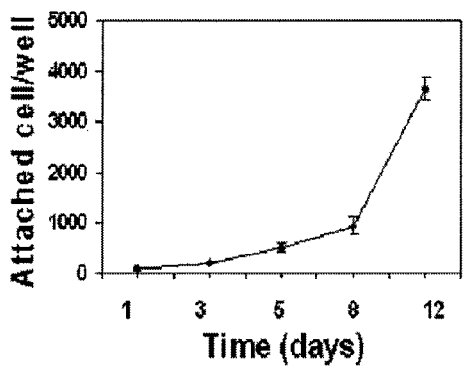
B.
ES cell markers:
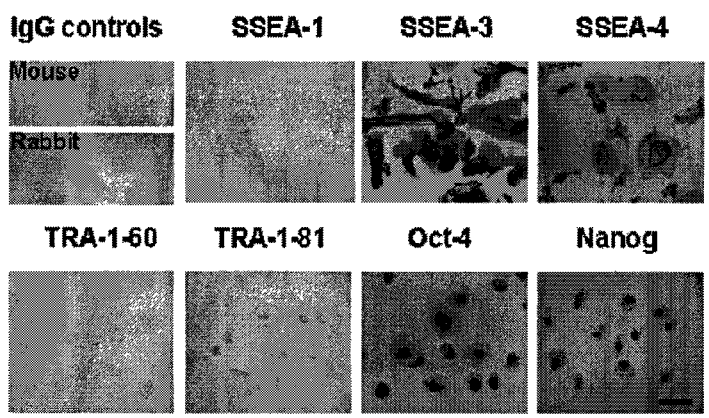
C. Hematopoietic cell markers:
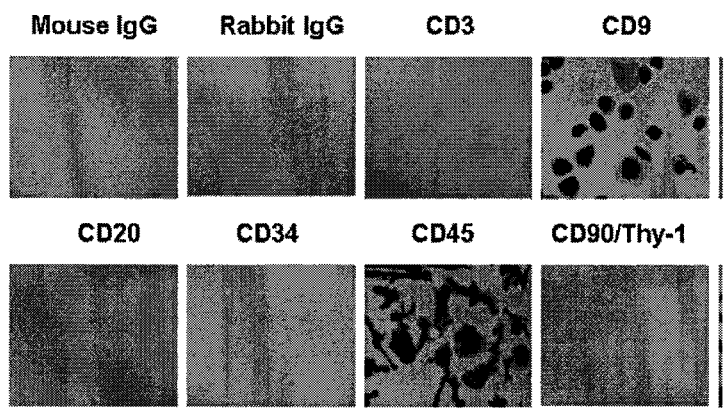

FIG. 4
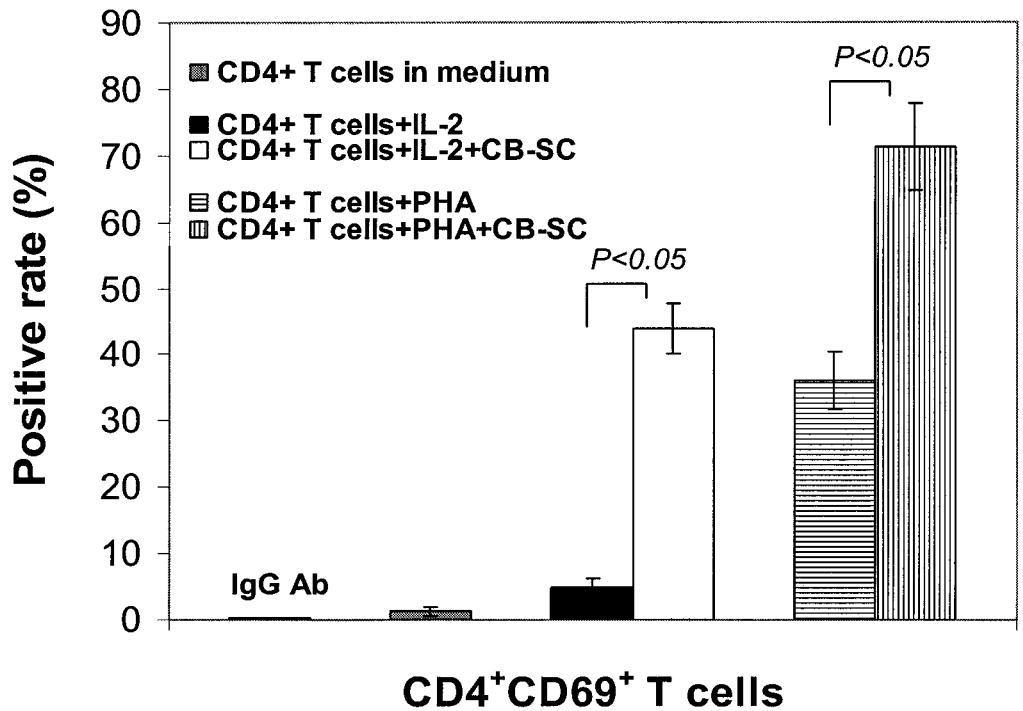
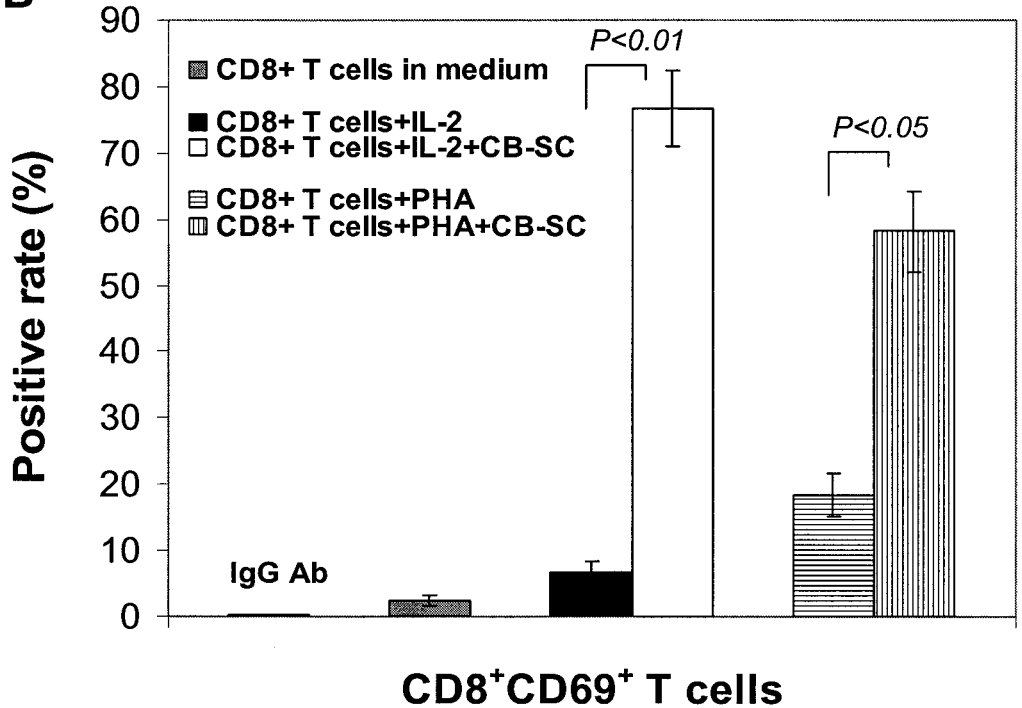

FIG. 5A&B
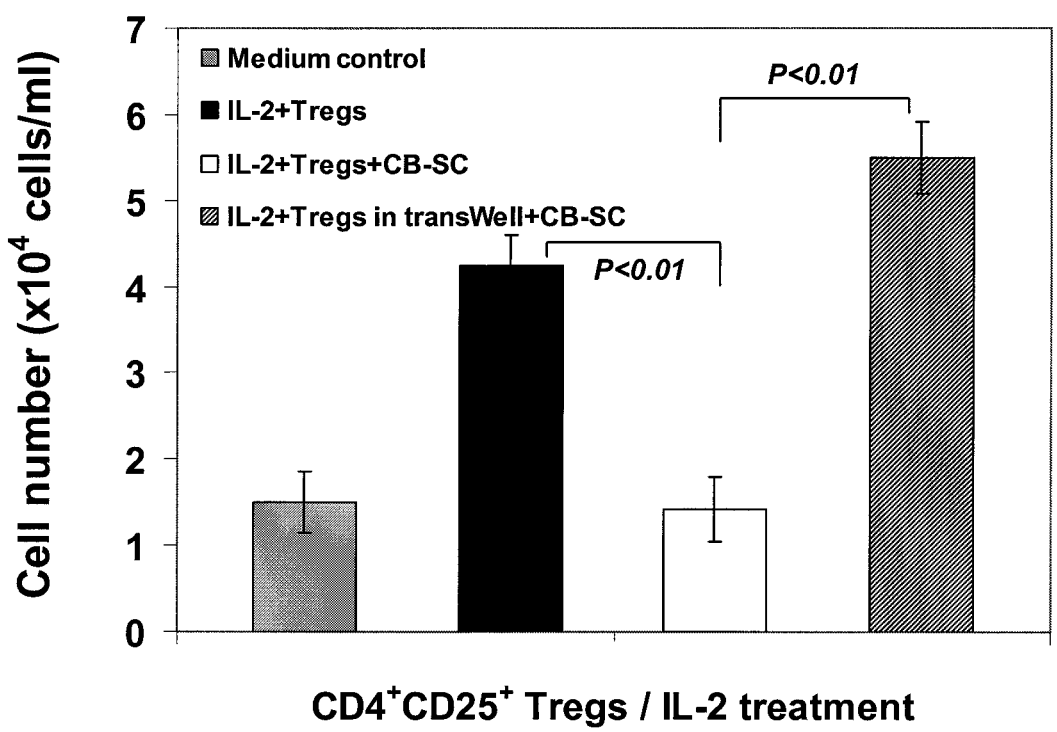
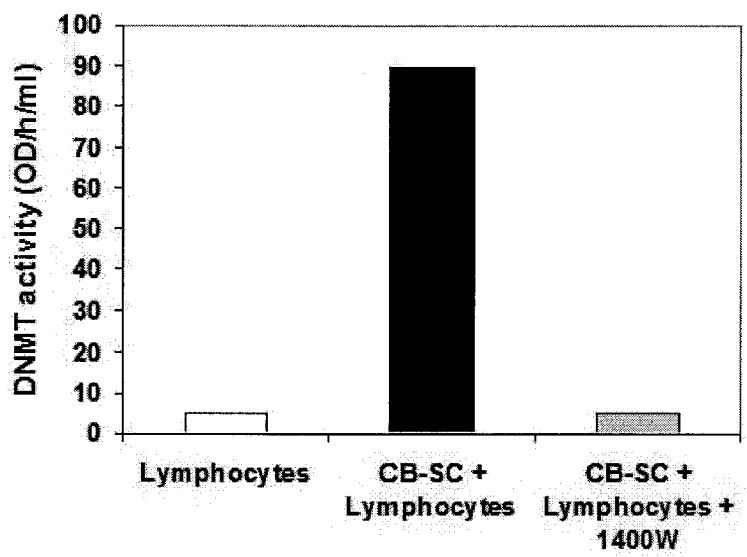

FIG. 8
A
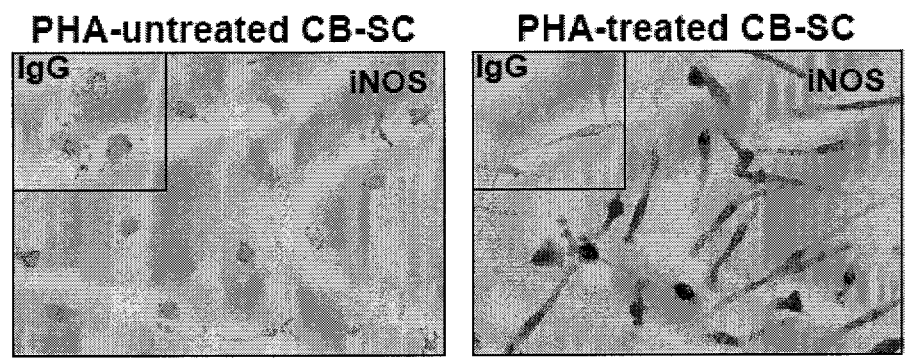
B
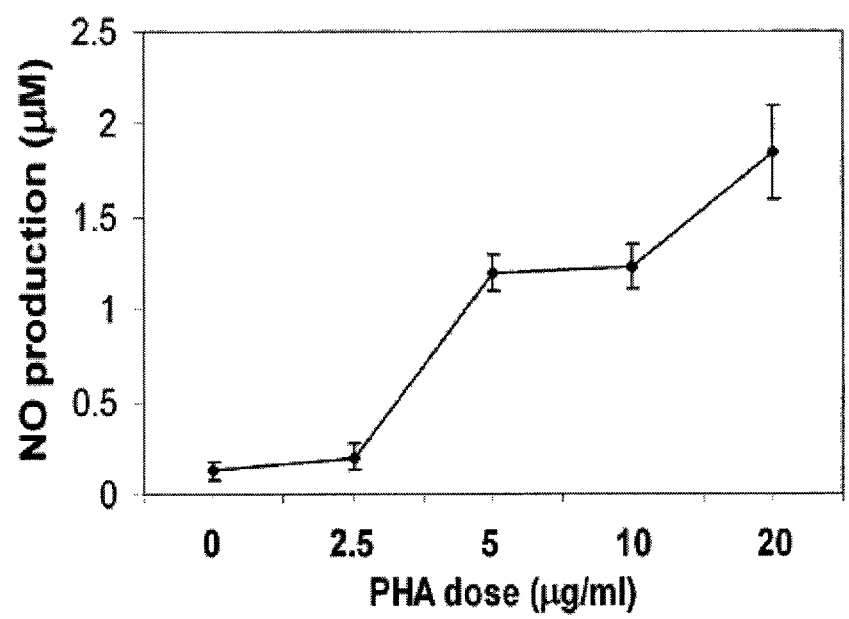

FIG. 10
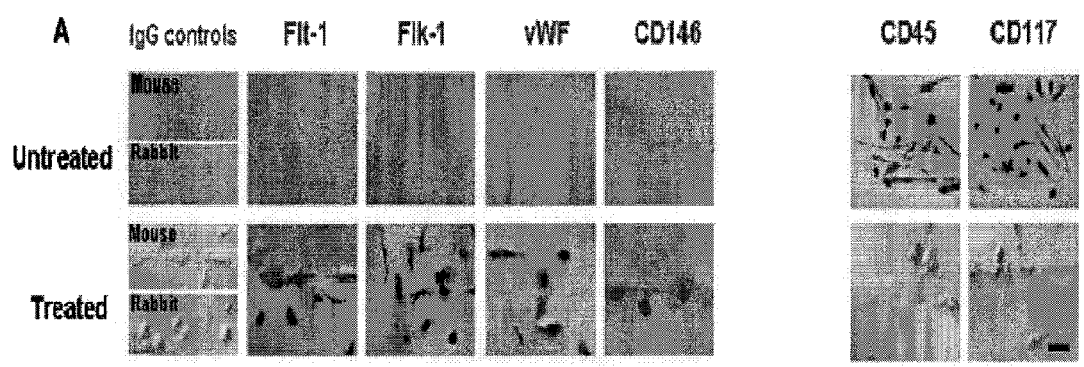
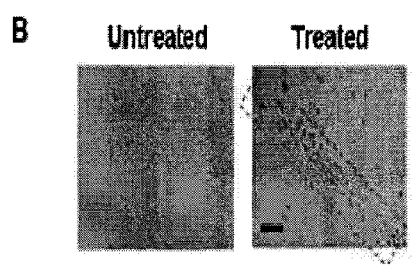

Expression of chemokine SDF-1 in islets:

Expression of SDF-1 receptor CXCR4 on CB-SC

FIG. 23A&B
A.
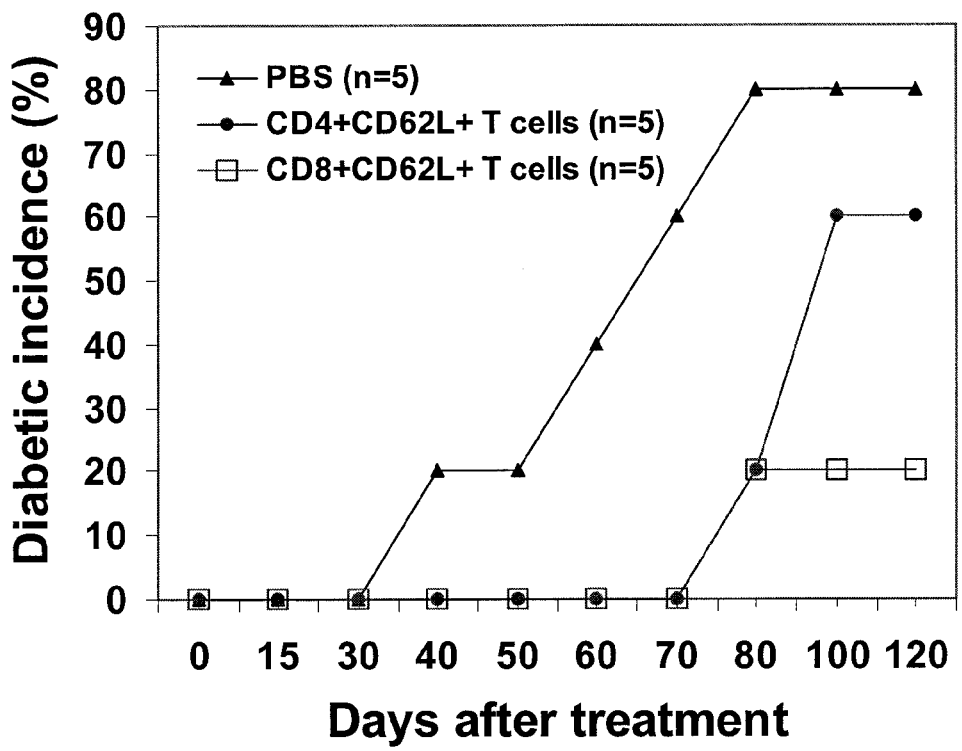
B.
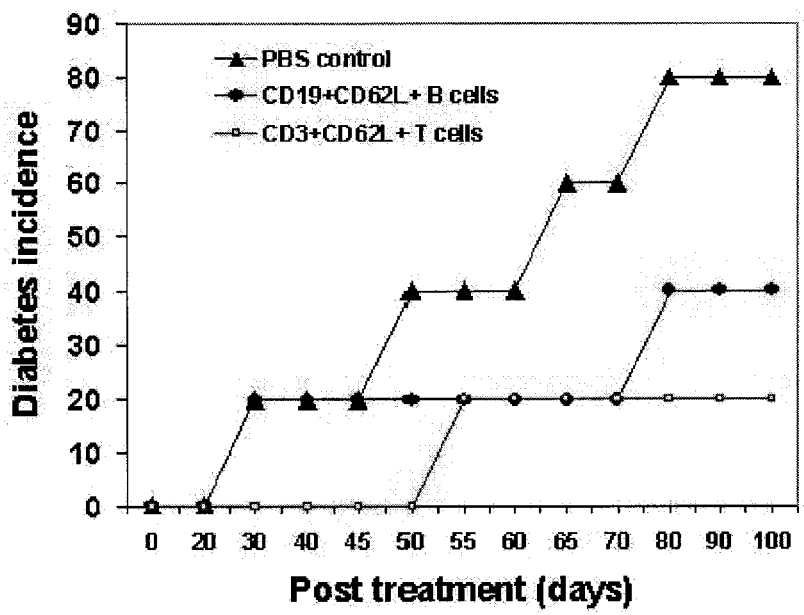

FIG. 24A-D
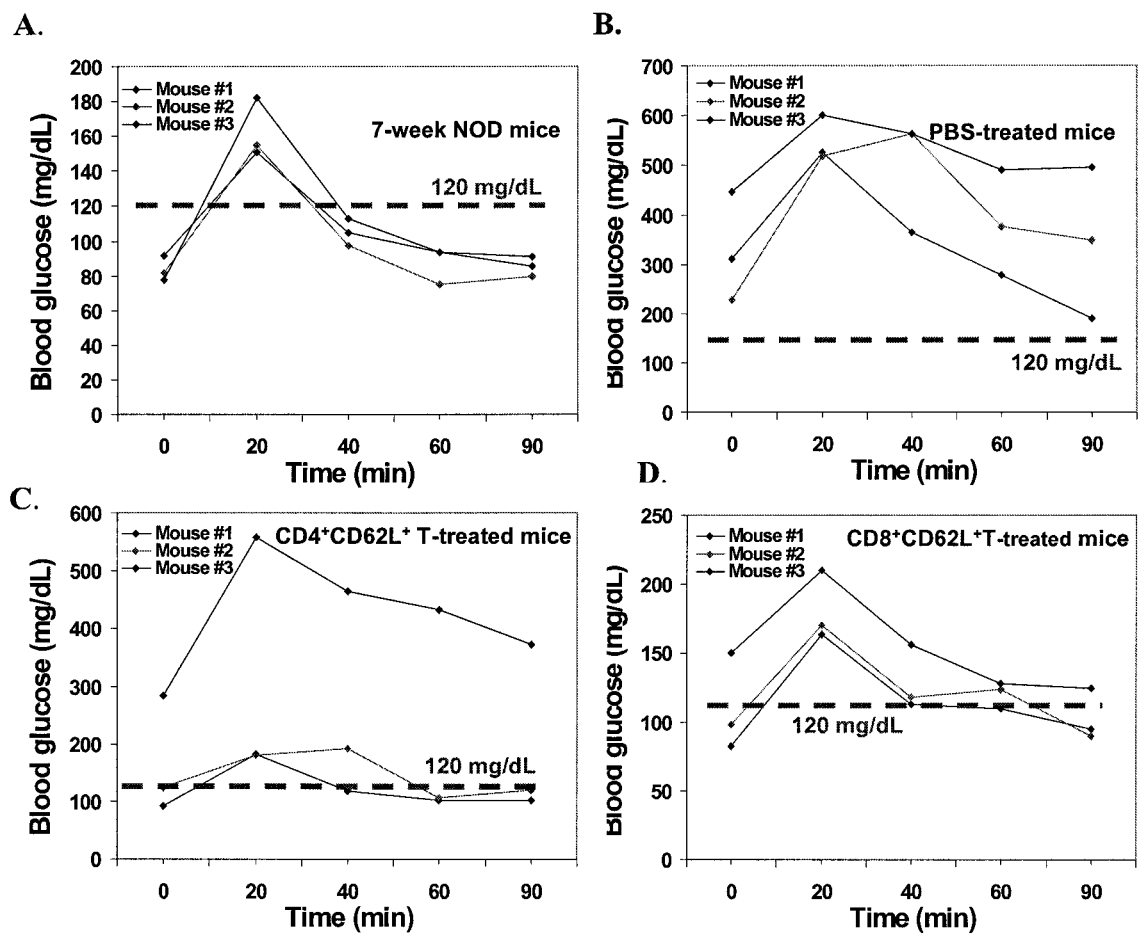

Figure 25A&B
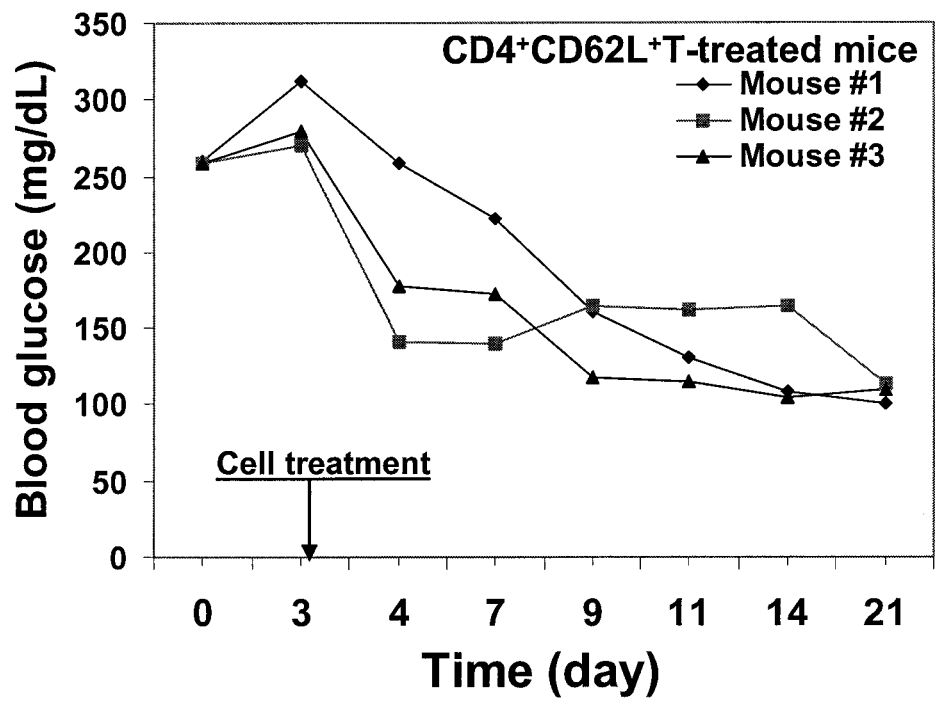
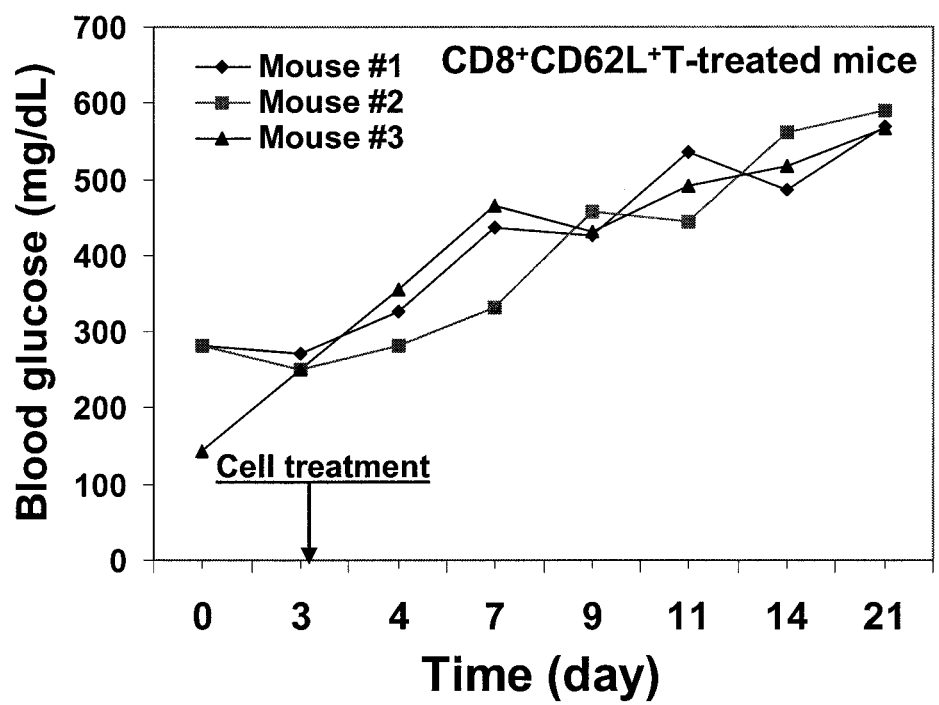

SEQUENCE LISTING

```
<160> NUMBER OF SEQ ID NOS: 8

<210> SEQ ID NO 1
<211> LENGTH: 360
<212> TYPE: PRT
<213> ORGANISM: Homo sapiens

<400> SEQUENCE: 1

Met Ala Gly His Leu Ala Ser Asp Phe Ala Phe Ser Pro Pro Pro Gly
1               5                   10                  15

Gly Gly Gly Asp Gly Pro Gly Gly Pro Glu Pro Gly Trp Val Asp Pro
            20                  25                  30

Arg Thr Trp Leu Ser Phe Gln Gly Pro Pro Gly Gly Pro Gly Ile Gly
        35                  40                  45

Pro Gly Val Gly Pro Gly Ser Glu Val Trp Gly Ile Pro Pro Cys Pro
    50                  55                  60

Pro Pro Tyr Glu Phe Cys Gly Gly Met Ala Tyr Cys Gly Pro Gln Val
65                  70                  75                  80

Gly Val Gly Leu Val Pro Gln Gly Gly Leu Glu Thr Ser Gln Pro Glu
                85                  90                  95

Gly Glu Ala Gly Val Gly Val Glu Ser Asn Ser Asp Gly Ala Ser Pro
            100                 105                 110

Glu Pro Cys Thr Val Thr Pro Gly Ala Val Lys Leu Glu Lys Glu Lys
        115                 120                 125

Leu Glu Gln Asn Pro Glu Glu Ser Gln Asp Ile Lys Ala Leu Gln Lys
    130                 135                 140

Glu Leu Glu Gln Phe Ala Lys Leu Leu Lys Gln Lys Arg Ile Thr Leu
145                 150                 155                 160

Gly Tyr Thr Gln Ala Asp Val Gly Leu Thr Leu Gly Val Leu Phe Gly
                165                 170                 175

Lys Val Phe Ser Gln Thr Thr Ile Cys Arg Phe Glu Ala Leu Gln Leu
            180                 185                 190

Ser Phe Lys Asn Met Cys Lys Leu Arg Pro Leu Leu Gln Lys Trp Val
        195                 200                 205

Glu Glu Ala Asp Asn Asn Glu Asn Leu Gln Glu Ile Cys Lys Ala Glu
    210                 215                 220
```

```
Thr Leu Val Gln Ala Arg Lys Arg Lys Arg Thr Ser Ile Glu Asn Arg
225                 230                 235                 240

Val Arg Gly Asn Leu Glu Asn Leu Phe Leu Gln Cys Pro Lys Pro Thr
            245                 250                 255

Leu Gln Gln Ile Ser His Ile Ala Gln Gln Leu Gly Leu Glu Lys Asp
        260                 265                 270

Val Val Arg Val Trp Phe Cys Asn Arg Arg Gln Lys Gly Lys Arg Ser
    275                 280                 285

Ser Ser Asp Tyr Ala Gln Arg Glu Asp Phe Glu Ala Ala Gly Ser Pro
    290                 295                 300

Phe Ser Gly Gly Pro Val Ser Phe Pro Leu Ala Pro Gly Pro His Phe
305                 310                 315                 320

Gly Thr Pro Gly Tyr Gly Ser Pro His Phe Thr Ala Leu Tyr Ser Ser
            325                 330                 335

Val Pro Phe Pro Glu Gly Glu Ala Phe Pro Pro Val Ser Val Thr Thr
        340                 345                 350

Leu Gly Ser Pro Met His Ser Asn
        355                 360

<210> SEQ ID NO 2
<211> LENGTH: 1410
<212> TYPE: DNA
<213> ORGANISM: Homo sapiens

<400> SEQUENCE: 2
ccttcgcaag ccctcatttc accaggcccc cggcttgggg cgccttcctt ccccatggcg      60
ggacacctgg cttcggattt cgccttctcg cccctccag gtggtggagg tgatgggcca     120
ggggggccgg agccgggctg ggttgatcct cggacctggc taagcttcca aggccctcct    180
ggagggccag gaatcgggcc gggggttggg ccaggctctg aggtgtgggg gattccccca    240
gccccccgcc gtatgagttc gtggggggga tggcgtactg tgggcccag gttggagtgg     300 ggctagtgcc ccaaggcggc ttggagacct ctcagcctga gggcgaagca ggagtcgggg    360
tggagagcaa ctccgatggg gcctccccgg agccctgcac cgtcacccct ggtgccgtga    420
agctggagaa ggagaagctg gagcaaaacc cggaggagtc ccaggacatc aaagctctgc    480
agaaagaact cgagcaattt gccaagctcc tgaagcagaa gaggatcacc ctgggatata    540
cacaggccga tgtggggctc accctggggg ttctatttgg gaaggtattc agccaaacga    600
ccatctgccg ctttgaggct ctgcagctta gcttcaagaa catgtgtaag ctgcggccct    660
tgctgcagaa gtgggtggag gaagctgaca caatgaaaa tcttcaggag atatgcaaag    720
cagaaaccct cgtgcaggcc cgaaagagaa agcgaaccag tatcgagaac cgagtgagag    780
gcaacctgga gaatttgttc ctgcagtgcc cgaaacccac actgcagcag atcagccaca    840
tcgcccagca gcttgggctc gagaaggatg tggtccgagt gtggttctgt aaccggcgcc    900
agaagggcaa gcgatcaagc agcgactatg cacaacgaga ggattttgag gctgctgggt    960 ctccttctc aggggaccag tgtcctttc tctggcccc agggccccat tttggtaccc     1020
caggctatgg gagccctcac ttcactgcac tgtactcctc ggtcccttc cctgaggggg     1080 aagcctttcc ccctgtctcc gtcaccactc tgggctctcc catgcattca aactgaggtg     1140
cctgcccttc taggaatggg ggacaggggg aggggaggag ctagggaaag aaaacctgga     1200
gtttgtgcca gggtttttgg gattaagttc ttcattcact aaggaaggaa ttggaacacc     1260
aaagggtggg ggcaggggag tttggggcaa ctggttggag ggaaggtgaa gttcaatgat    1320
```

```
gctcttgatt ttaatcccac atcatgtatc acttttttct taaataaaga agcctgggac    1380
acagtagata gacacactta aaaaaaaaaa                                    1410
```

<210> SEQ ID NO 3
<211> LENGTH: 305
<212> TYPE: PRT
<213> ORGANISM: Homo sapiens

<400> SEQUENCE: 3

```
Met Ser Val Asp Pro Ala Cys Pro Gln Ser Leu Pro Cys Phe Glu Ala
1               5                   10                  15

Ser Asp Cys Lys Glu Ser Ser Pro Met Pro Val Ile Cys Gly Pro Glu
            20                  25                  30

Glu Asn Tyr Pro Ser Leu Gln Met Ser Ser Ala Glu Met Pro His Thr
        35                  40                  45

Glu Thr Val Ser Pro Leu Pro Ser Ser Met Asp Leu Leu Ile Gln Asp
    50                  55                  60

Ser Pro Asp Ser Ser Thr Ser Pro Lys Gly Lys Gln Pro Thr Ser Ala
65                  70                  75                  80

Glu Lys Ser Val Ala Lys Lys Glu Asp Lys Val Pro Val Lys Lys Gln
                85                  90                  95

Lys Thr Arg Thr Val Phe Ser Ser Thr Gln Leu Cys Val Leu Asn Asp
            100                 105                 110

Arg Phe Gln Arg Gln Lys Tyr Leu Ser Leu Gln Gln Met Gln Glu Leu
        115                 120                 125

Ser Asn Ile Leu Asn Leu Ser Tyr Lys Gln Val Lys Thr Trp Phe Gln
    130                 135                 140

Asn Gln Arg Met Lys Ser Lys Arg Trp Gln Lys Asn Asn Trp Pro Lys
145                 150                 155                 160

Asn Ser Asn Gly Val Thr Gln Lys Ala Ser Ala Pro Thr Tyr Pro Ser
                165                 170                 175

Leu Tyr Ser Ser Tyr His Gln Gly Cys Leu Val Asn Pro Thr Gly Asn
            180                 185                 190

Leu Pro Met Trp Ser Asn Gln Thr Trp Asn Asn Ser Thr Trp Ser Asn
        195                 200                 205

Gln Thr Gln Asn Ile Gln Ser Trp Ser Asn His Ser Trp Asn Thr Gln
    210                 215                 220

Thr Trp Cys Thr Gln Ser Trp Asn Asn Gln Ala Trp Asn Ser Pro Phe
225                 230                 235                 240

Tyr Asn Cys Gly Glu Glu Ser Leu Gln Ser Cys Met Gln Phe Gln Pro
                245                 250                 255

Asn Ser Pro Ala Ser Asp Leu Glu Ala Ala Leu Glu Ala Ala Gly Glu
            260                 265                 270

Gly Leu Asn Val Ile Gln Gln Thr Thr Arg Tyr Phe Ser Thr Pro Gln
        275                 280                 285

Thr Met Asp Leu Phe Leu Asn Tyr Ser Met Asn Met Gln Pro Glu Asp
    290                 295                 300

Val
305
```

<210> SEQ ID NO 4
<211> LENGTH: 2098
<212> TYPE: DNA
<213> ORGANISM: Homo sapiens

<400> SEQUENCE: 4

```
attataaatc tagagactcc aggattttaa cgttctgctg gactgagctg gttgcctcat      60
gttattatgc aggcaactca ctttatccca atttcttgat acttttcctt ctggaggtcc     120
tatttctcta acatcttcca gaaaagtctt aaagctgcct taaccttttt tccagtccac     180
ctcttaaatt ttttcctcct cttcctctat actaacatga gtgtggatcc agcttgtccc     240
caaagcttgc cttgctttga agcatccgac tgtaaagaat cttcacctat gcctgtgatt     300
tgtgggcctg aagaaaacta tccatccttg caaatgtctt ctgctgagat gcctcacacg     360
gagactgtct ctcctcttcc ttcctccatg gatctgctta ttcaggacag ccctgattct     420
tccaccagtc ccaaaggcaa acaacccact tctgcagaga agagtgtcgc aaaaaaggaa     480
gacaaggtcc cggtcaagaa acagaagacc agaactgtgt tctcttccac ccagctgtgt     540
gtactcaatg atagatttca gagacagaaa tacctcagcc tccagcagat gcaagaactc     600
tccaacatcc tgaacctcag ctacaaacag gtgaagacct ggttccagaa ccagagaatg     660
aaatctaaga ggtggcagaa aaacaactgg ccgaagaata gcaatggtgt gacgcagaag     720
gcctcagcac ctacctaccc cagcctttac tcttcctacc accagggatg cctggtgaac     780
ccgactggga accttccaat gtggagcaac cagacctgga caattcaac ctggagcaac     840
cagacccaga acatccagtc ctggagcaac cactcctgga cactcagac tggtgcacc     900
caatcctgga caatcaggc ctggaacagt cccttctata actgtggaga ggaatctctg     960
cagtcctgca tgcagttcca gccaaattct cctgccagtg acttggaggc tgccttggaa    1020
gctgctgggg aaggccttaa tgtaatacag cagaccacta ggtattttag tactccacaa    1080
accatggatt tattcctaaa ctactccatg aacatgcaac ctgaagacgt gtgaagatga    1140
gtgaaactga tattactcaa tttcagtctg gacactggct gaatccttcc tctcccctcc    1200
tcccatccct cataggattt tcttgtttg gaaaccacgt gttctggttt ccatgatgcc     1260
catccagtca atctcatgga gggtggagta tggttggagc ctaatcagcg aggtttcttt    1320
tttttttttt ttcctattgg atcttcctgg agaaaatact tttttttttt tttttttga     1380
aacggagtct tgctctgtcg cccaggctgg agtgcagtgg cgcggtcttg gctcactgca    1440
agctccgtct cccgggttca cgccattctc ctgcctcagc ctcccgagca gctgggacta    1500
caggcgcccg ccacctcgcc cggctaatat tttgtatttt tagtagagac ggggtttcac    1560
tgtgttagcc aggatggtct cgatctcctg accttgtgat ccacccgcct cggcctccct    1620
aacagctggg atttacaggc gtgagccacc gcgccctgcc tagaaaagac attttaataa    1680
ccttggctgc cgtctctggc tatagataag tagatctaat actagtttgg atatctttag    1740
ggtttagaat ctaacctcaa gaataagaaa tacaagtaca aattggtgat gaagatgtat    1800
tcgtattgtt tgggattggg aggctttgct tattttttaa aaactattga ggtaaagggt    1860
taagctgtaa catacttaat tgatttctta ccgtttttgg ctctgttttg ctatatcccc    1920
taatttgttg gttgtgctaa tctttgtaga aagaggctc gtatttgctg catcgtaatg     1980
acatgagtac tgctttagtt ggtttaagtt caaatgaatg aaacaactat ttttccttta    2040
gttgatttta ccctgatttc accgagtgtt tcaatgagta aatatacagc ttaaacat      2098
```

<210> SEQ ID NO 5
<211> LENGTH: 321
<212> TYPE: PRT
<213> ORGANISM: Homo sapiens

<400> SEQUENCE: 5

```
His Ser Ala Arg Met Tyr Asn Met Met Glu Thr Glu Leu Lys Pro Pro
1               5                   10                  15

Gly Pro Gln Gln Thr Ser Gly Gly Gly Gly Asn Ser Thr Ala Ala
            20                  25                  30

Ala Ala Gly Gly Asn Gln Lys Asn Ser Pro Asp Arg Val Lys Arg Pro
                35                  40                  45

Met Asn Ala Phe Met Val Trp Ser Arg Gly Gln Arg Arg Lys Met Ala
    50                  55                  60

Gln Glu Asn Pro Lys Met His Asn Ser Glu Ile Ser Lys Arg Leu Gly
65                  70                  75                  80

Ala Glu Trp Lys Leu Leu Ser Glu Thr Glu Lys Arg Pro Phe Ile Asp
                85                  90                  95

Glu Ala Lys Arg Leu Arg Ala Leu His Met Lys Glu His Pro Asp Tyr
                100                 105                 110

Lys Tyr Arg Pro Arg Arg Lys Thr Lys Thr Leu Met Lys Lys Asp Lys
            115                 120                 125

Tyr Thr Leu Pro Gly Gly Leu Leu Ala Pro Gly Gly Asn Ser Met Ala
        130                 135                 140

Ser Gly Val Gly Val Gly Ala Gly Leu Gly Ala Gly Val Asn Gln Arg
145                 150                 155                 160

Met Asp Ser Tyr Ala His Met Asn Gly Trp Ser Asn Gly Ser Tyr Ser
                165                 170                 175

Met Met Gln Asp Gln Leu Gly Tyr Pro Gln His Pro Gly Leu Asn Ala
            180                 185                 190

His Gly Ala Ala Gln Met Gln Pro Met His Arg Tyr Asp Val Ser Ala
        195                 200                 205

Leu Gln Tyr Asn Ser Met Thr Ser Ser Gln Thr Tyr Met Asn Gly Ser
    210                 215                 220

Pro Thr Tyr Ser Met Ser Tyr Ser Gln Gln Gly Thr Pro Gly Met Ala
225                 230                 235                 240

Leu Gly Ser Met Gly Ser Val Val Lys Ser Glu Ala Ser Ser Ser Pro
                245                 250                 255

Pro Val Val Thr Ser Ser Ser His Ser Arg Ala Pro Cys Gln Ala Gly
                260                 265                 270

Asp Leu Arg Asp Met Ile Ser Met Tyr Leu Pro Gly Ala Glu Val Pro
            275                 280                 285

Glu Pro Ala Ala Pro Ser Arg Leu His Met Ser Gln His Tyr Gln Ser
        290                 295                 300

Gly Pro Val Pro Gly Thr Ala Ile Asn Gly Thr Leu Pro Leu Ser His
305                 310                 315                 320

Met

<210> SEQ ID NO 6
<211> LENGTH: 1085
<212> TYPE: DNA
<213> ORGANISM: Homo sapiens

<400> SEQUENCE: 6
cacagcgccc gcatgtacaa catgatggag acggagctga agccgccggg cccgcagcaa      60
acttcggggg gcggcggcgg caactccacc gcggcggcgg ccggcggcaa ccagaaaaac     120
agcccggacc gcgtcaagcg gcccatgaat gccttcatgg tgtggtcccg cgggcagcgg     180
cgcaagatgg cccaggagaa ccccaagatg cacaactcgg agatcagcaa gcgcctgggc     240
gccgagtgga aacttttgtc ggagacggag aagcggccgt tcatcgacga ggctaagcgg     300
```

```
ctgcgagcgc tgcacatgaa ggagcacccg gattataaat accggccccg gcggaaaacc       360
aagacgctca tgaagaagga taagtacacg ctgcccggcg ggctgctggc ccccggcggc       420
aatagcatgg cgagcggggt cggggtgggc gccggcctgg gcgcgggcgt gaaccagcgc       480
atggacagtt acgcgcacat gaacggctgg agcaacggca gctacagcat gatgcaggac       540
cagctgggct acccgcagca cccgggcctc aatgcgcacg gcgcagcgca gatgcagccc       600
atgcaccgct acgacgtgag cgccctgcag tacaactcca tgaccagctc gcagacctac       660
atgaacggct cgcccaccta cagcatgtcc tactcgcagc agggcacccc tggcatggct       720
cttggctcca tgggttcggt ggtcaagtcc gaggccagct ccagcccccc tgtggttacc       780
tcttcctccc actccagggc gccctgccag gccggggacc tccgggacat gatcagcatg       840
tatctccccg gcgccgaggt gccggaaccc gccgccccca gcagacttca catgtcccag       900
cactaccaga gcggcccggt gcccggcacg gccattaacg gcacactgcc cctctcacac       960
atgtgagggc cggacagcga actggagggg ggagaaattt tcaaagaaaa acgagggaaa      1020
tgggaggggt gcaaaagagg agagtaagaa acagcatgga gaaaacccgg tacgctcaaa      1080
aaaaa                                                                  1085

<210> SEQ ID NO 7
<211> LENGTH: 28
<212> TYPE: DNA
<213> ORGANISM: Artificial sequence
<220> FEATURE:
<223> OTHER INFORMATION: Primer sequence to Oct-4 from Homo sapien

<400> SEQUENCE: 7
aaagcggcag atggtcgttt ggctgaat                                           28

<210> SEQ ID NO 8
<211> LENGTH: 28
<212> TYPE: DNA
<213> ORGANISM: Artificial sequence
<220> FEATURE:
<223> OTHER INFORMATION: Primer sequence to Nanog from Homo sapien

<400> SEQUENCE: 8
tggcaggaga atttggctgg aactgcat                                           28
```

ISOLATION OF CD14 NEGATIVE, CD45 POSITIVE AND CD117 POSITIVE EMBRYONIC-LIKE STEM CELLS FREE OF MONOCYTES FROM HUMAN UMBILICAL CORD BLOOD MONONUCLEAR CELLS

CROSS-REFERENCE TO RELATED APPLICATION

This application is a continuation in part application of PCT/US06/038524 filed Oct. 3, 2006, which claims priority to U.S. Provisional Patent Application Ser. No. 60/724,328 filed Oct. 5, 2005. This application is also a continuation in part of PCT/US07/022260 filed on Oct. 18, 2007, which claim priority of U.S. Provisional Patent Application Ser. No. 60/852,901, filed Oct. 18, 2006 and U.S. Provisional Patent Application Ser. No. 60/926,846, filed Apr. 30, 2007. This application also claims priority of U.S. Provisional Patent Application Ser. No. 60/927,011, filed May 1, 2007. All applications are incorporated herein by reference.

BACKGROUND OF THE INVENTION

1. Field of the Invention

The present invention is related generally to embryonic-like stem cells isolated from human umbilical cord blood.

2. Background of the Invention

The increasing prevalence of chronic human diseases, e.g. cardiovascular disease, diabetes, and neuronal degenerative diseases, presents a challenge to find more effective therapies. Stem cell-based therapy, including embryonic and adult stem cells, provides a rational treatment tool for regenerative medicine and has potential to revolutionize modern therapeutics [A. Vats, R. C. Bielby, N. S. Tolley, R. Nerem, J. M. Polak, Stem cells, Lancet 366 (2005) 592-602; M. A. Hussain, N. D. Theise, Stem-cell therapy for diabetes mellitus, Lancet 364 (2004) 203-205; C. M. Rice, N. J. Scolding, Adult stem cells—reprogramming neurological repair? Lancet 364 (2004) 193-199; L. M. Hoffman, M. K. Carpenter, Characterization and culture of human embryonic stem cells, Nat Biotechnol. 23 (2005) 699-708]. Because of their high potential for self renewal and pluripotent differentiation capability, embryonic stem (ES) cells have become a very active area of investigation [A. Vats, R. C. Bielby, N. S. Tolley, R. Nerem, J. M. Polak, Stem cells, Lancet 366 (2005) 592-602; L. M. Hoffman, M. K. Carpenter, Characterization and culture of human embryonic stem cells, Nat Biotechnol. 23 (2005) 699-708; K. H. Wilan, C. T. Scott, S. Herrera, Chasing a cellular fountain of youth, Nat Biotechnol. 23 (2005) 807-815]. Ethical concerns, however, have limited their availability and practical usefulness [C. Dennis, Check E, 'Ethical' routes to stem cells highlight political divide, Nature 437 (2005) 1076-1077; M. Evans, Ethical sourcing of human embryonic stem cells—rational solutions? Nat Rev Mol Cell Biol. 6 (2005) 663-667]. Leaving aside these ethical concerns, using in vitro fertilization (IVF) and altered nuclear transfer (ANT) to generate ES cells is made problematic by the complexity of required technologies [M. Evans, Ethical sourcing of human embryonic stem cells—rational solutions? Nat Rev Mol Cell Biol. 6 (2005) 663-667; D. A. Melton, G. Q. Daley, C. G. Jennings, Altered nuclear transfer in stem-cell research—a flawed proposal, N Engl J Med. 351 (2004) 2791-2792].

Recently, human umbilical cord blood has been used as a source of stem cells to repopulate the hematopoietic system and other organs [J. Bonde, D. A. Hess, J. A. Nolta, Recent advances in hematopoietic stem cell biology, Curr Opin Hematol. 11 (2004) 392-398; K. K. Ballen, New trends in umbilical cord blood transplantation, Blood 105 (2005) 3786-3792; D. A. Peterson, Umbilical cord blood cells and brain stroke injury: bringing in fresh blood to address an old problem, J Clin Invest. 114 (2004) 312-314; V. Silani, L. Cova, M. Corbo, A. Ciammola, E. Polli, Stem-cell therapy for amyotrophic lateral sclerosis, Lancet 364 (2004) 200-202]. Cord blood provides an abundant source for generation of stem cells, including mesenchymal stem cells [K. Bieback, S. Kern, H. Kluter, H. Eichler, Critical parameters for the isolation of mesenchymal stem cells from umbilical cord blood, Stem Cells 22 (2004) 625-634; E. J. Gang, S. H. Hong, J. A. Jeong, S. H. Hwang, S. W. Kim, I. H. Yang, C. Ahn, H. Han, H. Kim, In vitro mesengenic potential of human umbilical cord blood-derived mesenchymal stem cells, Biochem Biophys Res Commun. 321 (2004) 102-108; G. Kogler, S. Sensken, J. A. Airey, T. Trapp, M. Muschen, N. Feldhahn, S. Liedtke, R. V. Sorg, J. Fischer, C. Rosenbaum, S. Greschat, A. Knipper, J. Bender, O. Degistirici, J. Gao, A. I. Caplan, E. J. Colletti, G. Almeida-Porada, H. W. Muller, E. Zanjani, P. Wernet, A new human somatic stem cell from placental cord blood with intrinsic pluripotent differentiation potential, J Exp Med. 200 (2004) 123-135] and monocyte-derived stem cells [Y. Zhao, T. Mazzone, Human umbilical cord blood-derived f-macrophages retain pluripotentiality after thrombopoietin expansion, Exp Cell Res. 310 (2005) 311-318]. Stem cells expressing ES molecular markers have been reported from cord blood after removal of hematopoietic cells (including deletion of all leukocyte common antigen CD45 positive cells) [C. P. McGuckin, N. Forraz, M. O. Baradez, S, Navran, J. Zhao, R. Urban, R. Tilton, L. Denner, Production of stem cells with embryonic characteristics from human umbilical cord blood, Cell Prolif. 38 (2005) 245-55]. However, the scarcity of this previously-described cell population [C. P. McGuckin, N. Forraz, M. O. Baradez, S, Navran, J. Zhao, R. Urban, R. Tilton, L. Denner, Production of stem cells with embryonic characteristics from human umbilical cord blood, Cell Prolif. 38 (2005) 245-55] in cord blood significantly restricts its practical application.

Several other embryonic-like stem cells derived from adult sources rather than embryonic sources have also been disclosed. For example, U.S. Pat. No. 7,045,148, United States Patent Applications Serial Numbers 2005/0148034, 2005/0118715, 2004/0028660, 2003/0235909, 2002/0160510, 2003/0180269 and International Patent Application Number WO 03/068937 disclose embryonic-like stem cells extracted from the placenta or from the umbilical cord blood. United States Patent Application Serial Number 2006/0078993 discloses embryonic-like stem cells derived from the amniotic membrane of umbilical cord. The stem cells disclosed in these patents or patent applications are of mesenchymal origin, which do not express the CD45 marker (CD45$^-$). In another example, United States Patent Application Serial Number 2006/0147426 discloses stem cells derived from human bone marrow.

Accordingly, better methods of isolating autologous stem cells are needed to overcome the challenges faced by current stem cell research, such as ethical concerns and immune rejection. Accordingly, there is a need in the art for methods of isolation of stem cells with embryonic-stem cell characteristics from readily available sources.

BRIEF SUMMARY OF THE INVENTION

The present invention discloses a type of stem cell isolated from human umbilical cord blood, designated herein as cord blood-stem cells (CB-SC). These novel stem cells are of hematopoeitic (and not mesenchymal) origin as indicated by the high expression of the CD45 marker (CD45+). These cells can be isolated and expanded using simple technology. CB-SC share properties with human ES cells and hematopoietic cells, including low immunogenicity, ability to proliferate and the ability to differentiate to multiple types of cells designated herein as cord blood-stem cells (CB-SC), which display the characteristics of embryonic stem cells and hematopoietic cells. These cells have the capability of proliferation and are able to differentiate to multiple types of cells. In addition, CB-SC display low immunogenicity and immune regulation. These cells are suitable for use in stem cell-based therapies for the treatment of diseases such as Parkinson's disease, diabetes, spinal cord damage, multiple sclerosis (MS) cardiovascular disease, stroke and birth defects, and can regulate autoimmune lymphocytes. The present invention further discloses that these cord-blood stem cells can also regulate autoimmune lymphocytes and can be used to prevent, treat, reduce, and/or delay onset of autoimmune disease such as type 1 diabetes.

In one aspect, the present invention discloses isolated embryonic-like stem cells from human umbilical-cord blood, designated herein as CB-SC, which are characterized by: (a) displaying embryonic stem cell characteristics; (b) displaying hematopoietic cell characteristics; (c) phenotypically distinct from lymphocytes, macrophages and monocytes; (d) phenotypically distinct from hematopoietic stem cells; (e) displaying low immunogenicity; and (f) displaying immune regulation on lymphocytes. These novel embryonic-like stem cells are capable of proliferation and are able to differentiate to multiple types of cells.

In another aspect, the invention discloses a composition and method for preventing, treating, and/or reducing an autoimmune disease in a mammalian subject. In an embodiment, the autoimmune disease is type 1 diabetes. In an embodiment, lymphocytes are treated with CB-SC by co-culturing the lymphocytes with CB-SC. An effective dose of the CB-SC-treated lymphocytes is then administered to the subject to prevent, treat, and/or reduce the autoimmune disease. In another embodiment, an effective dose of CB-SC is directly administrated to the subject to treat the autoimmune disease.

In a preferred embodiment, the embryonic stem characteristics include having phenotypes positive for stem cell markers Oct-4 and Nanog. In another embodiment, the hemotopoietic characteristics are characterized by being positive for the hematopoietic stem cell marker CD45. In a further embodiment, the stem cells are phenotypically distinct from lymphocytes, macrophages and monocytes by being negative for CD3, CD20, CD11b/Mac-1 and CD14 markers. In still another embodiment, the stem cells are phenotypically distinct from hematopoietic stem cells by being negative for CD34 marker. In still a further embodiment, the low immunogenicity of these stem cells is characterized by the stem cells not being able to stimulate lymphocyte proliferation in an allogeneic mixed lymphocyte reaction. In a further embodiment, the stem cells display immune regulation by inhibition of mitogen-stimulated lymphocyte proliferation and regulation of T cell subsets (CD4+ T cells, CD8+ T cells, and CD4+CD25+ regulatory T cells).

The embryonic-like stem cells of the present invention are capable of differentiating to a variety of cells, which include but are not limited to endothelial-like cells, neuronal-like cells, insulin-producing cells, oligodendrocytes, and megakaryocytes.

The present invention further discloses a composition for stem cell-based therapy comprising the embryonic-like stem cells of the present invention. In an embodiment, the embryonic-like stem cells of the present invention are used for treating hyperglycemia in a diabetic mammalian subject by administering the cells to the subject.

In yet another embodiment, the present invention discloses a method for isolating the embryonic-like stem cells of the present invention. The method comprises: (a) providing a sample of human umbilical cord blood; (b) removing red cells from the sample to obtain mononuclear cells; (c) culturing the mononuclear cells in a culture medium in a non-tissue culture treated culture vessel; and (d) obtaining a cell population which is attached to the culture vessel. The attached cell population can be detached from the culture vessel by, for example, incubation in lidocaine hydrochloride solution wherein the lidocaine hydrochloride is from about 0.1% to about 5%. Optionally, the attached cells can be detached by further incubating the cells with EDTA solution or EDTA solution containing trypsin (trypsin/EDTA) wherein the EDTA is from about 0.5 mM to about 2.5 mM, and the trypsin is from about 0.05% to about 0.25%. Furthermore, the cell culture does not require a cell feeder.

In one aspect, the invention discloses a method of harvesting embryonic-like stem cells from umbilical cord blood comprising extracting umbilical cord blood comprising umbilical cord blood mononuclear cells; culturing the mononuclear cells in growth medium, such that the mononuclear cells revert to embryonic-like stem cells; and isolating the embryonic-like stem cells. In some embodiments, the growth medium comprises RPMI 1640 medium and fetal bovine serum. The cells do not require feeder cell layers to grow in vitro and does not form teratomas when grown in vivo. Red cells can be removed from umbilical cord blood to obtain mononuclear cells prior to culturing. Culturing can further include seeding the mononuclear cells on a surface with a net positive charge, such as polystyrene and glass. Isolating the embryonic-like stem cells includes removing the cells attached to the surface. For example, the cells can be incubated with a solution comprising lidocaine hydrochloride and/or ethylenediamine tetraacetic acid (EDTA). In some embodiments, a substantially homogeneous population of embryonic-like stem cell can be isolated.

In some embodiments, isolating the embryonic-like stem cells can further include selecting cell that have a positive marker for at least one of Octamer-binding transcription factor 4 (Oct-4), Nanog homeobox (Nanog), SRY (sex determining region Y)-box 2 (Sox-2), CD9, and CD45, a negative marker for at least one of CD3, CD20, CD11b/Mac-1, CD11c, and CD14; and a negative marker for CD 34. In some embodiments, the CB-SC are positive for one or more of the following markers: activated leukocyte cell adhesion molecule (ALCAM), complement component 5a receptor 1 (C5AR1), CD37, CD63, CD74, colony stimulating factor 1 receptor (CSF1R), integrin alpha 3, and myosin heavy chain 9 (non-muscle).

In another aspect, the invention discloses a method of directing cell differentiation of embryonic-like stem cells by incubating the embryonic-like stem cells of the present invention with an inducer, wherein the inducer directs maturation of the embryonic-like stem cells into a defined population of cells. Non-limiting examples of inducers include Exendin-4, granulocyte monocyte colony stimulating factor (GM-CSF), granulocyte-macrophage colony-stimulating, nerve growth factor (NGF), 5-Aza-2'-deoxycytidine, retinoic acid (RA), dimethyl sulfoxide (DMSO), thrombopoietin, hepatocyte growth factor (HGF), vascular endothelial growth factor isoform165 (VEGF165), epidermal growth factor (EGF), erythropoietin (EPO), interleukin-2 (IL-2), IL-5, IL-7, IL-18, interferon-gamma, granulocyte-macrophage colony-stimulating factor (GM-CSF), macrophage colony-stimulating factor (M-CSF), phorbol 12-myristate 13-acetate (PMA), lipopolysaccharide (LPS), granulocyte colony-stimulating factor (G-CSF), all trans-retinoic acid (ATRA), vitaminD3, bone morphogenetic proteins (BMPs), brain derived neurotrophic factor (BDNF), glial derived neurotrophic factor (GDNF), growth factors, fibroblast growth factor (FGF), transforming growth factors (TGF), ciliary neurotrophic factor (CNTF), leukemia inhibitory factor (LIF), glial growth factor (GGF), tumor necrosis factors (TNF), interferon, insulin-like growth factors (IGF), colony stimulating factors (CSF), KIT receptor stem cell factor (KIT-SCF), interferon, triiodothyronine, thyroxine, erythropoietin, silencers, SHC (SRC-homology-2-domain-containing transforming protein), neuroproteins, proteoglycans, glycoproteins, neural adhesion molecules, and other cell-signaling molecules and mixtures, thereof. The defined population of cells can have properties of cells from the following non-limiting examples of cells: beta cell-like insulin-producing cells, neuronal cells, cardiomyocyte cells, megakaryocyte cells, endothelial cells, epithelial cells, red blood cells, lymphocytes, monocytes, macrophages, granulocytes, hepatocytes, nephrogenic cells, adipogenic cells, osteoblast cells, osteoclastic cells, alveolar cells, cardiac cells, intestinal cells, renal cells, and retinal cells. Differentiating can be carried out by transducing the cells with a vector that contains a nucleic acid encoding the inducer and expresses the inducer in the cells. The vector can be a plasmid, cosmid, bacteriophage, DNA virus, RNA virus, or retrovirus vector. For example, CB-SC can differentiate into hepatocytes when exposed to hepatocyte growth factor (HGF); into endothelial cells when exposed to vascular endothelial growth factor isoform165 (VEGF165); into epithelial cells when exposed to epidermal growth factor (EGF); into red blood cells when exposed to erythropoietin (EPO); into lymphocytes when exposed to interleukin-2 (IL-2), IL-5, IL-7, IL-18, interferon-gamma; into monocyte/macrophage when exposed to granulocyte-macrophage colony-stimulating factor (GM-CSF); into macrophage colony-stimulating factor (M-CSF) when exposed to phorbol, 12-myristate 13-acetate (PMA), lipopolysaccharide (LPS); into granulocyte when exposed to granulocyte colony-stimulating factor (G-CSF), all trans-retinoic acid (ATRA), vitaminD3; into osteoblast cells when exposed to bone morphogenetic proteins (BMPs).

In another aspect, the invention discloses an isolated embryonic-like stem cell harvested from human umbilical cord blood with a positive marker for at least one of Oct-4, Nanog, Sox-2, CD9, and CD45, a negative marker for at least one of CD3, CD20, CD11b/Mac-1, CD11c, and CD14; and a negative marker for CD 34. The isolated embryonic-like stem cell can further include at least one, or at least two, or preferably at least three of the following embryonic genes selected from the group consisting of Zinc finger protein 206 (ZNF206), Zic family member 3 heterotaxy 1 (ZIC3), Zic family member 2 (ZIC2), Growth associated protein 43 (GAP43), PR domain containing 14 (PRDM14), Protein tyrosine phosphatase, receptor-type, Z polypeptide 1 (PTPRZ1), Podocalyxin-like (PODXL), and Zinc finger protein 589 (ZNF589).

In some embodiments, the isolated embryonic-like stem cell is capable of differentiating into insulin-producing cells. The insulin-producing cells can express at least one, or preferably at least two, or more preferably at least three insulin gene transcription factors. Non-limiting examples of insulin gene transcription factors include leucine zipper MafA, Pdx-1 (pancreatic duodenal homeobox factor 1), NeuroD1 (neurogenic differentiation 1), HNF6 (hepatocyte nuclear factor 6), Nkx6.1 (Nk homeobox gene), and Nkx2.2.

In another aspect, the invention discloses a method of suppressing lymphocytes in a subject in need thereof, comprising co-culturing a first population of cells comprising embryonic-like stem cells with a second population of cells comprising lymphocytes, administering at least one of the treated first or second cell populations after co-culturing to a subject. In some embodiments, the second cell population is administered. The lymphocytes can be allogeneic lymphocytes, or autologous lymphocytes from peripheral blood. Culturing the lymphocytes with the embryonic-like stem cells modulates the lymphocytes. In some embodiments, following co-culturing with the embryonic-like stem cells, the T lymphocytes decrease the amount of inflammatory cytokines produced, and/or increase the amount of TGF-$\beta$1 produced. Following co-culturing, the lymphocytes can reduce expression of one or more of the inflammatory cytokines selected from the group TNF-$\alpha$, IL-$\beta$, IL-$\gamma$, IL-15, IL-17, IL-18, IL1$\beta$, IL-21, IL22, IL-23, IL-4, IL-5, and IL-6. The modulation of the T cells following co-culture with embryonic-like stem cells can be modulated through nitric oxide (NO) as demonstrated in the Examples. In other embodiments, the modulation can include decreasing intracellular IL-10 levels, increasing expression of CD69 on activated T lymphocytes, inhibiting proliferation of IL-2-stimulated lymphocytes, inhibiting proliferation of PHA-stimulated lymphocytes, increasing the percentage of $CD4^+CD62L^+$ T cells, $CD8^+CD62L^+$ T cells and/or $CD19^+CD62L^+$ B cells. Following administration to a subject, insulin production in the subject can be increased. The method can include up-regulating nitric oxide (NO) production. In some embodiments, the method can be used to treat, ameliorate the symptoms or delay onset of type I diabetes. The administered lymphocytes can migrate to the pancreas. In some embodiments, following co-culturing, the lymphocytes express the receptor CXCR-4, which is capable of binding to the SDF-1 (stromal derived factor 1) on islet cells. In another embodiments, following administration, the delivered lymphocytes can migrate to the pancreatic lymph nodes.

In yet another aspect, the invention discloses a method of treating diabetes in a mammalian subject in need thereof, comprising culturing embryonic-like stem cells from umbilical cord blood; and administering the cells to the subject in an amount effective to treat diabetes. The cells can be differentiated into insulin-producing cells. The administering step can be through any suitable method, for example, intraperitoneal (ip), intravenous (iv) or intraarterial injection. The cells can be administered in an amount of from about $1 \times 10^4$-$1 \times 10^9$ cells per subject. The method can be used to treat or ameliorate the symptoms of insulin-dependent diabetes. In some embodiments, the cells are administered into the pancreas of the subject. In some embodiments, the cells are encapsulated in an insulin-permeable capsule.

In a preferred embodiment, the umbilical cord blood is obtained from the subject. Alternatively, the umbilical cord blood can be obtained from an allogenic or xenogenic source. The embryonic-like stem cells can be obtained through collecting umbilical cord blood comprising umbilical cord blood mononuclear cells; culturing the mononuclear cells ex-vivo, such that the mononuclear cells revert to embryonic-like stem cells; and isolating the embryonic-like stem cells. The mononuclear cells can be seeded on a hydrophobic surface with a net positive charge. Isolating the cells can include isolating the cells attached to the surface.

In yet another embodiment, the invention discloses a pharmaceutical composition useful for the treatment of diabetes comprising, cord-blood insulin-producing cells in a pharmaceutically acceptable carrier, wherein the cord-blood insulin-producing cells are derived from umbilical cord blood. The composition can be an injectable composition. In some embodiments, the cells are encapsulated in an insulin-permeable capsule. The peripheral-blood insulin-producing cells can express at least one insulin gene transcription factor, or preferably two or more insulin gene transcription factors. In other embodiments, lymphocytes following co-culturing with CB-SC can be administered or co-administered to a subject together with the CB-SC. For example, lymphocytes that are positive for the CD62L marker and at least one of the following markers: CD4+, CD8+, and CD3+, can be administered.

BRIEF DESCRIPTION OF THE DRAWINGS

FIG. 1 shows the results of characterization of CB-SC for embryonic and hematopoietic cell markers. (A) Quantitation of attached cells per well over 12 days; (B) Expression of ES cell markers on 15-day CB-SC; (C) Expression of hematopoietic cell markers on 15-day CB-SC;

FIG. 4 is the regulation of CB-SC on CD69 molecule expressed by the sorted CD4+ and CD8+ T cells. The sorted CD4+ (A) and CD8+ (B) T cells were cocultured with CB-SC in the presence of IL-2 (500 U/ml) and PHA (10 μg/ml) for 5 days. CD69 expression was analyzed by flow analysis. Data represent mean (±SD) of three experiments;

FIG. 5A shows the inhibitory effects of CB-SC on the sorted CD4+CD25+ regulatory T cells. CD4+CD25+ regulatory T cells were sorted from allogeneic peripheral blood and cocultured with CB-SC for 5 days, in the presence of interleukin (IL)-2 500 U/ml. For cell sorting, cells were double immunostained with FITC-conjugated mouse anti-human CD4 and allophycocyanin (APC)-conjugated mouse anti-human CD25. CD4+CD25+ regulatory T cells were presented in transwell system as control and evaluate the action of cell-cell contacting on inhibition. Data represent one of at least three experiments with the similar results;

FIG. 5B is a bar graph showing that DNA methyltransferase (DNMT) activity of lymphocytes by CB-SC-derived NO can be significantly blocked by presence of a specific inducible nitric oxide synthase (iNOS) inhibitor 1400 W;

FIG. 8 shows the result of the examination of NO production and iNOS expression. A, Immunocytochemistry for iNOS expression in the PHA-treated CB-SC. Normal rabbit IgG (insert, top left) served as negative control for rabbit anti-iNOS polyclonal antibody. Images represent from 10 μg/ml PHA-stimulated CB-SC. Immunostaining results were obtained from three cord blood preparations and yielded the similar results. Scale bar, 47 μm. B, Assay for NO production. CB-SC were treated with PHA at different doses for 3-5 days. The supernatants were collected for NO examination using Griess reaction. Results represent mean (±SD) of three experiments;

FIG. 10 shows the differentiation of CB-SC into endothelial-like cells. CB-SC were treated with 50 ng/ml VEGF for 10-14 days and then prepared for immunostaining. Untreated cells served as control. (A) VEGF-treated or untreated CB-SC were stained with endothelial cell markers Flt-1, Flk-1, von Willebrand Factor (vWF), and CD146 (left panel); also evaluated with hematopoietic cell markers CD45 and CD117 (right panel). Scale bar, 6 μm. (B) Phase contrast image showed formation of cell chain-like structure in VEGF-treated CB-SC. Untreated cells served as control. Scale bar, 50 μm. Cells were photographed with a MicroMAX 5 MHz Digital Camera using Zeiss Axiovert 100TV Fluorescence microscope. Scale bar, 50 μm. The images are representative of five experiments;

FIG. 23A is a graph showing the percentage of diabetes incidence following days after treatment with $CD4^+CD62L^+$ T cells, $CD8^+CD62L^+$ T cells, or control (PBS);

FIG. 23B is a graph showing the percentage of diabetes incidence following days after treatment with $CD19^+CD62L^+$ B cells, $CD3^+CD62L^+$ T cells, or control (PBS);

FIG. 24A is a graph showing the results of the intraperitoneal glucose tolerance testing (IPGTT) in 7 week NOD mice over time;

FIG. 24B is a graph showing the results of the intraperitoneal glucose tolerance testing (IPGTT) in PBS-treated (control) mice over time;

FIG. 24C is a graph showing the results of the intraperitoneal glucose tolerance testing (IPGTT) in $CD4^+CD62L^+$ T cell-treated mice over time;

FIG. 24D is a graph showing the results of the intraperitoneal glucose tolerance testing (IPGTT) in $CD8^+CD62L^+$ T cell-treated mice over time;

FIG. 25A is a graph showing blood glucose levels in 3 mice following treatment with $CD4^+CD62L^+$ T cells;

FIG. 25B is a graph showing blood glucose levels in 3 mice following treatment with $CD8^+CD62L^+$ T cells.

DETAILED DESCRIPTION OF THE INVENTION

Figure 2:
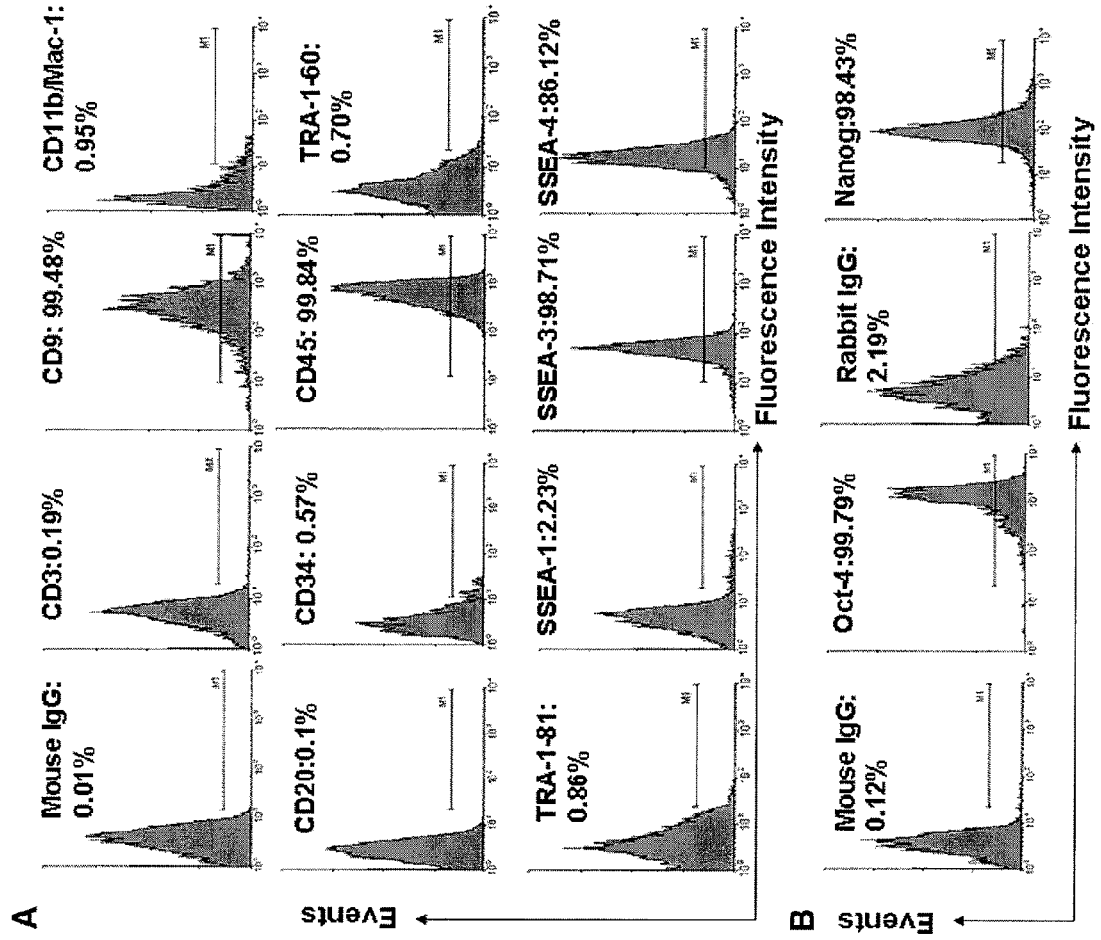
FIG. 2 is the result of flow analyses of embryonic and hematopoietic cell markers on CB-SC (A) and transcription factors (B)

The present invention discloses a novel population of isolated embryonic-like stem cells isolated from human umbilical cord blood. These stem cells, designated herein as cord blood-stem cells (CB-SC), represent a unique cell population displaying both embryonic and hematopoietic cell characteristics. CB-SC of the present invention are characterized by: (a) displaying embryonic stem cell characteristics; (b) displaying hematopoietic cell characteristics; (c) phenotypically distinct from lymphocytes, macrophages and monocytes; (d) phenotypically distinct from hematopoietic stem cells; (e) displaying low immunogenicity; and (f) displaying immune regulation. Furthermore, AB-SC are capable of proliferation and can differentiate to multiple types of cells. These cells are suitable for stem cell-based therapies. In some embodiments, these cord-blood stem cells are also capable of regulating autoimmune lymphocytes and can be used to prevent or treat an autoimmune disease such as type 1 diabetes.

In an embodiment, the present invention discloses a method for isolating the embryonic-like stem cells of the present invention. The method comprises: (a) providing a sample of human umbilical cord blood; (b) removing red cells from the sample to obtain mononuclear cells; (c) culturing the mononuclear cells in a culture medium in a non-tissue culture treated culture vessel; and (d) obtaining a cell population which is attached to the culture vessel. The attached cell population can be detached from the culture vessel by, for example, incubation in lidocaine hydrochloride solution wherein the lidocaine hydrochloride is from about 0.1% to about 5%. Optionally, the attached cells can be detached by further incubating the cells with EDTA solution or EDTA solution containing trypsin (trypsin/EDTA) wherein the EDTA is from about 0.5 mM to about 2.5 mM, and the trypsin is from about 0.05% to about 0.25%. Furthermore, the cell culture does not require a cell feeder. What is meant by "non-tissue culture treated culture vessel" as used herein is that the culture vessel has not been treated with vacuum gas plasma prior to cell culture. Examples of suitable culture vessels include, but are not limited to, chamber glass slides and Petri dishes.

The present invention discloses a novel type of stem cells isolated from human umbilical cord blood, designated herein as cord blood-stem cells (CB-SC). These novel stem cells are of blood (and not mesenchymal) origin as indicated by the high expression of the CD45 marker ($CD45^+$). These cells can be isolated and expanded using simple technology. CB-SC share properties with human ES cells and hematopoietic cells, including ability to proliferate and the ability to differentiate to other types of cells. Since these cells can be isolated from the umbilical cord blood of a subject, they are suitable for autologous stem cell therapies. The present invention also discloses the use of CB-SC to prevent or delay onset of diabetes, and to reverse or treat diabetes. As shown in the Examples, after co-culturing with CB-SC's, various populations of T lymphocytes can be isolated and administered to a subject to prevent or delay onset of diabetes, and/or to reverse or treat diabetes. For example, T cells that are positive for the CD62L marker (a marker for immature lymphocytes) can be isolated. CD8+CD62L+ T cells can significantly delay diabetes onset in a subject at risk. For example, administration of CD8+CD62L+ T cells was shown to modulate the initiation stage of autoimmune responses of type 1 diabetic NOD mice and significantly delayed diabetes onset. CD4+CD62L+ T cells and/or CD19+CS62L+ T cells can delay or prevent diabetes onset in a subject at risk thereof. Following administration of either CD4+CD62L+ T cells or CD19+CS62L+ T cells, diabetes was reversed in the established diabetic NOD mice, which were able to achieve euglycemia.

The present invention discloses isolated embryonic-like stem cells from human umbilical cord blood, designated herein as CB-SC, which display embryonic stem cell characteristics; display hematopoietic cell characteristics, are phenotypically distinct from lymphocytes, macrophages and monocytes; and are phenotypically distinct from hematopoietic stem cells. These novel embryonic-like stem cells are capable of proliferation and are able to differentiate to other types of cells.

In a preferred embodiment, the embryonic stem characteristics include having phenotypes of positive for stem cell markers Oct-4 (SEQ ID. Nos: 1 and 2), Nanog (SEQ ID. NO. 3 and 4), and Sox-2 (SEQ ID. NO. 5 and 6), together with other embryonic stem (ES) cell-related genes, e.g., Zinc finger and SCAN domain containing 10 (ZNF206, also named ZSCAN10), Zic family member 3 heterotaxy 1 (ZIC3), Zic family member 2 (ZIC2), Growth associated protein 43 (GAP43), PR domain containing 14 (PRDM14), Protein tyrosine phosphatase, receptor-type, Z polypeptide 1 (PTPRZ1), Podocalyxin-like (PODXL), Polyhomeotic homolog 1 (PHC1), and Zinc finger protein 589 (ZNF589). The sequences for Oct-4, Nanog, and Sox-2 can be found under GenBank Accession Nos. NM_002701, Z11898 and Q01860; GenBank Accession Nos. NM_024865 and NP_079141; and GenBank Accession Nos. Z31560 and CAA83435, respectively. The sequences for the following markers can be found at the respective GenBank Accession numbers: activated leukocyte cell adhesion molecule (ALCAM) (GenBank Accession No. NP_001618); complement component 5a receptor 1 (C5AR1) (GenBank Accession No. AAO65969); CD37 (GenBank Accession No. CAG46675); CD63 (GenBank Accession No. CAG46893); CD74 (GenBank Accession No. NP_001020329); colony stimulating factor 1 receptor (CSF1R) (GenBank Accession No. NP_005202); integrin alpha 3 (GenBank Accession No. EAW94647); and myosin heavy chain 9 (non-muscle). (GenBank Accession No. NM_002473).

In another embodiment, the hemotopoietic characteristics are characterized by being positive for the leukocyte common antigen CD45. In a further embodiment, the stem cells are phenotypically distinct from lymphocytes, dendritic cells, macrophages and monocytes by being negative for CD3, CD20 (B-lymphocyte cell-surface antigen B1, Accession No. M27394), CD11c (integrin, alpha X, Accession No. NM_000887), CD11b/Mac-1 (complement component 3 receptor 3 subunit, Accession No. NM_000632) and CD14 (Accession Nos. NM_001040021 and P08571) markers. In still another embodiment, the stem cells are phenotypically distinct from hematopoietic stem cells by being negative for CD34 marker (Hematopoietic progenitor cell antigen CD34, Accession No. P28906) (Craig et al. 1994, British Journal of Haematology, 88:24-30; Lansdorp, P. A I. and Dragowaka, W. (1992) J. Exp. Med. 175:1501-1509; Sutherland, H. J., et al. (1989), Blood 74.1563-1570)).

In one embodiment, the embryonic-like stem cells of the present invention are capable of differentiating to other cells such as but are not limited to insulin-producing cells. The embryonic-like stem cells display the receptor of glucagon-like peptide 1 (GLP-1). Administration of exendin-4, a long-acting agonist of GLP-1, can improve their insulin production and cell differentiation. As shown in the Examples, the embryonic-like stem cells give rise to functional insulin-producing cells when transplanted into the streptozotocin (STZ)-induced diabetic NOD-scid mice. In the present invention, we disclose that CB-SC exist in human umbilical cord blood and have the capability to produce insulin.

The CB-SC are capable of proliferation, producing insulin, and behave like islet β-islet cell progenitors. In some embodiments, the insulin producing cells can be characterized by positive expression of one or more insulin gene transcription factors. Examples of insulin gene transcription factor include but are not limited to leucine zipper MafA, Pdx-1 (pancreatic duodenal homeobox factor 1), NeuroD1 (neurogenic differentiation 1), HNF6 (hepatocyte nuclear factor 6, also known as Onecut1), Nkx6.1 (Nk homeobox gene), and Nkx2.2.

Since CB-SC can give rise to multiple cell types, such as but are not limited to, beta cells, neuronal cells, cardiomyocyte cells, megakaryocyte cells, endothelial cells, epithelial cells, red blood cells, lymphocytes, monocytes, macrophages, granulocytes, hepatocytes, nephrogenic cells, adipogenic cells, osteoblast cells, osteoclastic cells, alveolar cells, cardiac cells, intestinal cells, renal cells, and retinal cells in presence of different inducers, as demonstrated by displaying different lineage-specific markers and unique morphologies.

The present invention further discloses a composition for stem cell-based therapy comprising the embryonic-like stem cells of the present invention. In some embodiments, the embryonic-like stem cells of the present invention are used for treating hyperglycemia in a diabetic mammalian subject by administering the cells to the subject. In other embodiments, the embryonic-like stem cells of the present invention can be co-cultured with T lymphocytes, thereby enhancing the production of various populations of T cells that can prevent, delay, treat, and/or reduce diabetes. In some embodiments, CD62L+ T cells can be administered to a subject to delay onset, reduce or ameliorate diabetes. In other embodiments, CD8+CD62L+ T cells can be administered to a subject to delay diabetes onset in a subject. In yet other embodiments, T cells that are positive for CD62L and positive for at least one of CD19 or CD4 can be administered to reduce diabetes or ameliorate diabetes in a subject. For example, CD4+CD62L+ T cells and/or CD19+CD62L+ T cells can be administered to a subject, wherein glucose levels in said subject are reduced to levels with normal ranges for said subject. In some embodiments, the CB-SC-treated lymphocytes can be expanded in vitro by using lymphocyte growth factors. Non-limiting examples of growth factors that can be used to expand the population of CB-SC treated lymphocytes and/or specific subpopulations of CB-SC treated lymphocytes (such as, for example, CD4+CD62L+ T cells or CD8+CD62L+ T cells) include IL-2, anti-CD3 antibody (anti-CD3Ab), IL-3, or human serum.

In yet another embodiment, the present invention discloses a method for isolating the embryonic-like stem cells of the present invention. The method comprises providing a sample of umbilical cord blood; removing red cells from the sample to obtain mononuclear cells; culturing the mononuclear cells on a hydrophobic surface with a net positive charge and obtaining a cell population which is attached to the surface. The attached cell population can be detached from the surface by, for example, incubation with lidocaine hydrochloride. The lidocaine hydrochloride can be in the range of about 0.1% to about 5%. Optionally, the attached cells can be detached by further incubating the cells with EDTA solution or EDTA solution containing trypsin (trypsin/EDTA). The EDTA can be in the range from about 0.5 mM to about 2.5 mM, and the trypsin can be in the range from about 0.05% to about 0.25%. Furthermore, the cell culture does not require a cell feeder. These cells are suitable for stem cell-based therapies, particularly autologous stem cell therapies.

The terms used in this invention are, in general, expected to adhere to standard definitions generally accepted by those having ordinary skill in the art of molecular biology. A few exceptions, as listed below, have been further defined within the scope of the present invention.

As used herein, the terms "embryonic stem cell" refers to a stem cell that is derived from the inner cell mass of a blastocyst (e.g., a 4- to 7-day-old human embryo) and that is pluripotent. The terms "embryonic-like stem cell", "cord blood-stem cell (CB-SC)", and "cord blood derived insulin-producing cells (CB-IPC)" are used interchangeably herein to refer to a stem cell that is not derived from the inner cell mass of a blastocyst. An embryonic-like stem cell is pluripotent. The embryonic-like stem cells display at least a subset of characteristics of embryonic stem cells (ES) and hematopoietic cells. In some embodiments, adult peripheral blood can be used in a similar manner to umbilical cord blood to derive embryonic-like stem cells of the present invention.

As used herein, the term "pluripotential", "pluripotential for differentiation" or "pluripotent" refers that the cell is positive for one or more of the pluripotent markers such as but are not limited to Oct-4, Nanog, and Sox-2 and the cell has the potential to differentiate to at least a subset of the mammalian body's approximately 260 cell types upon appropriate stimulations such as by the appropriate growth factors.

As used herein, the term "totipotent cell" refers to a cell that is able to form a complete embryo (e.g., a blastocyst).

As used herein, the term "stem cell" refers to a master cell that can reproduce indefinitely to form the specialized cells of tissues and organs. A stem cell is a developmentally pluripotent or multipotent cell. A stem cell can divide to produce two daughter stem cells, or one daughter stem cell and one progenitor ("transit") cell, which then proliferates into the tissue's mature, fully formed cells. The "stem cell" used herein includes "progenitor cells" unless otherwise noted.

The term "subject" refers to any living organism in which an immune response is elicited. The term refers to a living animal or human in need of treatment for, or susceptible to, a condition involving an unwanted or undesirable microorganism, e.g., a particular treatment for having an unwanted pathogenic cell as defined below. The term subject includes, but is not limited to, humans, nonhuman primates such as chimpanzees and other apes and monkey species; farm animals such as cattle, sheep, pigs, goats and horses; domestic mammals such as dogs and cats; laboratory animals including rodents such as mice, rats and guinea pigs, and the like. The term does not denote a particular age or sex. Thus, adult and newborn subjects, as well as fetuses, whether male or female, are intended to be covered. In preferred embodiments, the subject is a mammal, including humans and nonhuman mammals. In the most preferred embodiment, the subject is a human.

The term "undifferentiated" as used herein refers to pluripotent embryonic stem cells which have not developed a characteristic of a more specialized cell. As will be recognized by one of skill in the art, the terms "undifferentiated" and "differentiated" are relative with respect to each other. A stem cell which is "differentiated" has a characteristic of a more specialized cell. Differentiated and undifferentiated cells are distinguished from each other by several well-established criteria, including morphological characteristics such as relative size and shape, ratio of nuclear volume to cytoplasmic volume; and expression characteristics such as detectable presence of known markers of differentiation. A marker of differentiation indicating that cells are differentiated or undifferentiated includes a protein, carbohydrate, lipid, nucleic acid, functional characteristic and/or morphological characteristic which is specific to a differentiated cell.

As used herein, the term "substantially homogeneous" when applied to cells, refers to a population of cells, wherein at least about 70%, and preferably about 80%, more preferably 90% of the cells in the population are of the same cell type. Examples of cell types include, but are not limited to, embryonic-like stem cells, beta cell-like insulin-producing cells, neuronal cells, cardiomyocyte cells, megakaryocyte cells, endothelial cells, epithelial cells, red blood cells, lymphocytes, monocytes, macrophages, granulocytes, hepatocytes, nephrogenic cells, adipogenic cells, osteoblast cells, osteoclastic cells, alveolar cells, cardiac cells, intestinal cells, renal cells, retinal cells, and the like. In some embodiments, the term "substantially homogeneous" describes a population of cells wherein at least about 70%, and preferably about 80%, more preferably 90% of the cells in the population are undifferentiated. In a further embodiment a substantially homogeneous population of cells is one in which more than 95% of the cells are undifferentiated. In another embodiment, a substantially homogeneous population of cells is one in which more than 99% of the cells are undifferentiated. A population of cells can be assayed for one or more markers of differentiation to determine whether the population of cells is substantially homogeneous.

The production and/or maintenance of a substantially homogeneous population of embryonic-like stem cells and/or a differentiated cell type may be measured by assessing the proportion of cells for particular markers of undifferentiated cells and/or differentiated cells. For example, relative ratios of transcription products for markers of undifferentiated cells such as Oct4, neuroprogenitor markers such as nestin and Ngn-3, and markers of mature neuron markers such as $\beta$-tubulin and TPH2 is assessed by quantitative RT-PCR. Also, production and localization of markers of undifferentiated cells can be assessed by immunocytochemistry.

Markers of undifferentiated stem cells and differentiated cells are assayed by any of various methods such as antibody-based detection techniques using an antibody specific for a particular marker. Antibody-based techniques include immunofluorescence and immunoblotting. Further assays include assays for detection of mRNAs encoding a particular marker. Such assays include polymerase chain reaction, blot hybridization (also known as Northern blots) and in situ hybridization. Details of these and other such assays are described herein and in standard references including J. Sambrook and D. W. Russell, Molecular Cloning: A Laboratory Manual, Cold Spring Harbor Laboratory Press; 3rd ed., 2001; F. M. Ausubel, Ed., Short Protocols in Molecular Biology, Current Protocols; 5th ed., 2002; and E. Harlow and D. Lane, Antibodies: A Laboratory Manual, Cold Spring Harbor Laboratory Press, 1988.

As used herein, the term "culture medium" refers generally to any substance or preparation used for the cultivation of living cells. A "cell culture" refers to a growth of cells in vitro; although the cells proliferate they do not organize into tissue per se.

As used herein, the terms "treat," "treating," "treatment," and the like refer to reducing or ameliorating a disorder and/or symptoms associated therewith. Although not precluded, treating a disorder or condition does not require that the disorder, condition or symptoms associated therewith be completely eliminated. As used herein, the terms "prevent,"

"preventing," "prevention," and the like include "prophylactic treatment" which refers to reducing the probability of developing a disorder or condition in a subject, who does not have, but is at risk of or susceptible to developing a disorder or condition.

The term "administration" or "administering" is used throughout the specification to describe the process by which embryonic-like stem cells according to the present invention are delivered to a subject. The embryonic-like stem cells can be administered a number of ways including parenteral (such term referring to intravenous and intraarterial as well as other appropriate parenteral routes), intrathecal, intraventricular, intraparenchymal (including into the spinal cord, brainstem or motor cortex), intracisternal, intracranial, intrastriatal, and intranigral, among others which term allows the cells to migrate to the site where needed. The compositions according to the present invention can be used without treatment with an inducer ("untreated", i.e., without further treatment in order to promote differentiation of cells within the stem cell sample) or after treatment ("treated") with an inducer or other agent which causes the embryonic-like stem cells to differentiate into cells exhibiting a favorable phenotype. Administration will often depend upon the disease or condition treated and can preferably be via a parenteral route, for example, intravenously, by administration into the cerebral spinal fluid or by direct administration into the affected tissue in the brain or other body site. For example, in the case of diabetes, the preferred route of administration will into the pancreas. In the case of Alzheimer's disease, Huntington's disease and Parkinson's disease, the preferred route of administration will be a transplant directly into the striatum (caudate cutamen) or directly into the substantia nigra (Parkinson's disease). In the case of amyotrophic lateral sclerosis (Lou Gehrig's disease) and multiple sclerosis, the preferred administration is through the cerebrospinal fluid. In the case of lysosomal storage disease, the preferred route of administration is via an intravenous route or through the cerebrospinal fluid. In the case of stroke, the preferred route of administration will depend upon where the stroke is, but will often be directly into the affected tissue (which may be readily determined using MRI or other imaging techniques). In the case of heart disease, the method of administration can be by direct infusion into the affected area, or it can be by the intravenous route to allow transmigration through the circulatory system and "homing" to the affected site.

The terms "grafting" and "transplanting" and "graft" and "transplantation" are used throughout the specification synonymously to describe the process by which embryonic-like stem cells or other cells according to the present invention are delivered to the site where the cells are intended to exhibit a favorable effect, such as repairing damage to a patient's central nervous system, treating autoimmune diseases, treating diabetes, treating neurodegenerative diseases, or treating the effects of nerve, muscle and/or other damage caused by birth defects, stroke, cardiovascular disease, a heart attack or physical injury or trauma or genetic damage or environmental insult to the body, caused by, for example, disease, an accident or other activity. The embryonic-like stem cells or other cells for use in the present invention can also be delivered in a remote area of the body by any mode of administration as described above, relying on cellular migration to the appropriate area in the body to effect transplantation.

The term "essentially" is used to describe a population of cells or a method which is at least 90% effective, more preferably at least about 95% effective and even more preferably at least 98% effective. Thus, a method which "essentially" eliminates a given cell population, eliminates at least about 90% of the targeted cell population, most preferably at least about 98% of the cell population. Embryonic-like stem cells according to the present invention, in certain preferred embodiments, are essentially free of hematopoietic cells (i.e., negative for hematopoietic stem cell marker CD34), essentially free of lymphocyte (i.e., negative for lymphocyte markers CD3, CD20, and CD90), essentially free of monocyte/macrophage antigens CD11b/Mac-1 and CD14, essentially free of dendritic cell antigen CD11c, and essentially free of mesenchymal (CD45⁻) cells.

The term "non-tumorigenic" refers to the fact that the cells do not give rise to a neoplasm or tumor. The embryonic-like stem cells for use in the present invention are generally free from neoplasia and cancer.

The term "inducer," as used herein, describes agents which may be added to cell culture (which term includes any cell culture medium which may be used to grow differentiated cells according to the present invention) containing pluripotent stem which will induce the cells to a desired cellular phenotype. Non-limiting examples of induces for use in the present invention include, for example, Exendin-4, granulocyte monocyte colony stimulating factor (GM-CSF), granulocyte-macrophage colony-stimulating, nerve growth factor (NGF), 5-Aza-2'-deoxycytidine, retinoic acid (RA), dimethyl sulfoxide (DMSO), thrombopoietin, hepatocyte growth factor (HGF), vascular endothelial growth factor isoform165 (VEGF165), epidermal growth factor (EGF), erythropoietin (EPO), interleukin-2 (IL-2), IL-5, IL-7, IL-18, interferon-gamma, granulocyte-macrophage colony-stimulating factor (GM-CSF), macrophage colony-stimulating factor (M-CSF), phorbol 12-myristate 13-acetate (PMA), lipopolysaccharide (LPS), granulocyte colony-stimulating factor (G-CSF), all trans-retinoic acid (ATRA), vitaminD3, bone morphogenetic proteins (BMPs), brain derived neurotrophic factor (BDNF), glial derived neurotrophic factor (GDNF), growth factors, fibroblast growth factor (FGF), transforming growth factors (TGF), ciliary neurotrophic factor (CNTF), leukemia inhibitory factor (LIF), glial growth factor (GGF), tumor necrosis factors (TNF), interferon, insulin-like growth factors (IGF), colony stimulating factors (CSF), KIT receptor stem cell factor (KIT-SCF), interferon, triiodothyronine, thyroxine, erythropoietin, silencers, SHC(SRC-homology-2-domain-containing transforming protein), neuroproteins, proteoglycans, glycoproteins, neural adhesion molecules, and other cell-signaling molecules and mixtures, thereof.

Isolation of Cord Blood-Stem Cells from Human Umbilical Cord Blood

Umbilical cord blood has provided an important source of stem cells for research as it has unique advantages compared to other sources of stem cells: no ethical concerns, no risk to the donors, and low risk of graft-versus-host disease (GVHD) [K. K. Ballen, New trends in umbilical cord blood transplantation, Blood 105 (2005) 3786-3792; P. R. Sanberg, A. E. Willing, S. Garbuzova-Davis, S. Saporta, G. Liu, C. D. Sanberg, P. C. Bickford, S. K. Klasko, N. E1-Badri, Umbilical cord blood-derived stem cells and brain repair, Ann NY Acad Sci. 1049 (2005) 67-83; D. A. Peterson, Umbilical cord blood cells and brain stroke injury: bringing in fresh blood to address an old problem, J Clin Invest. 114 (2004) 312-314]. The present invention discloses a population of novel embryonic-like stem cells isolated from embryonic cord blood. They are designated herein as cord blood-stem cells (CB-SC). As used herein, the terms "umbilical cord blood" and "cord blood" are interchangeable.

According to the methods of the invention, CB-SC represent the attached population of cells obtained from culturing the mononuclear cells of the umbilical cord blood after the removal of the red blood cells. These cells are generated using a very basic cell culture medium with a low percentage of serum (e.g., 7% fetal bovine serum), and without cell feeders. This is in contrast to ES cells generated using cell feeders. The requirement of cell feeders for such cells raises potential contamination problems [M. Richards, C. Y. Fong, W. K. Chan, P. C. Wong, A. Bongso, Human feeders support prolonged undifferentiated growth of human inner cell masses and embryonic stem cells, Nat Biotechnol. 20 (2002) 933-936]. An exemplified method of obtaining the CB-SC is shown in Example 1 below. The attached cell population from culturing the mononuclear cells in this Example represented approximately 5% of the mononuclear cells. The cells can be cultured in a culture vessel that is non-tissue culture treated (i.e., no vacuum gas plasma-treated). Examples of such a culture vessel include but are not limited to chamber glass slides and Petri dishes. The cells cannot be cultured in a culture dish which has been vacuum gas plasma-treated. The attached cell population can be detached from the culture vessel by, for example, incubation in lidocaine hydrochloride solution wherein the lidocaine hydrochloride is from about 0.1% to about 5%. Optionally, the attached cells can be detached by further incubating the cells with EDTA solution or EDTA solution containing trypsin (trypsin/EDTA) wherein the EDTA is from about 0.5 mM to about 2.5 mM, and the trypsin is from about 0.05% to about 0.25%. These cells are found to be able to proliferate with an estimated doubling time of about 2.8 days based on a growth curve generated over 12 days (FIG. 1A). Using the growth conditions in Example 1, CB-SC can be passaged up to a total of 7 passages over 2 months with the cells passaged every 5 to 7 days. Proliferation decreased after 3 months in culture. However, it is very likely that further optimization of growth conditions with growth factors may improve their potential for longer term proliferation. Examples of these growth factors include but are not limited to leukemia inhibitory factor (LIF), basic fibroblast growth factor (bFGF), interleukin 3, thrombopoietin (TPO), insulin, transferin, all trans-retinoic acid, vitamin D, vitamins, activins, and different concentration of serums.

As compared to other reported cord blood-derived stem cells [K. Bieback, S. Kern, H. Kluter, H. Eichler, Critical parameters for the isolation of mesenchymal stem cells from umbilical cord blood, Stem Cells 22 (2004) 625-634; E. J. Gang, S. H. Hong, J. A. Jeong, S. H. Hwang, S. W. Kim, I. H. Yang, C. Ahn, H. Han, H. Kim, In vitro mesengenic potential of human umbilical cord blood-derived mesenchymal stem cells, Biochem Biophys Res Commun. 321 (2004) 102-108; G. Kogler, S. Sensken, J. A. Airey, T. Trapp, M. Muschen, N. Feldhahn, S. Liedtke, R. V. Sorg, J. Fischer, C. Rosenbaum, S. Greschat, A. Knipper, J. Bender, O. Degistirici, J. Gao, A. I. Caplan, E. J. Colletti, G. Almeida-Porada, H. W. Muller, E. Zanjani, P. Wernet, A new human somatic stem cell from placental cord blood with intrinsic pluripotent differentiation potential, J Exp Med. 200 (2004) 123; M. Aoki, M. Yasutake, T. Murohara, Derivation of functional endothelial progenitor cells from human umbilical cord blood mononuclear cells isolated by a novel cell filtration device, Stem Cells 22 (2004) 994-1002; D. A. Ingram, L. E. Mead, H. Tanaka, V. Meade, A. Fenoglio, K. Mortell, K. Pollok, M. J. Ferkowicz, D. Gilley, M. C. Yoder, Identification of a novel hierarchy of endothelial progenitor cells using human peripheral and umbilical cord blood, Blood 104 (2004) 2752-2760; N. Baal, K. Reisinger, H. Jahr, R. M. Bohle, O. Liang, K. Munstedt, C. V. Rao, K. T. Preissner, M. T. Zygmunt, Expression of transcription factor Oct-4 and other embryonic genes in CD133 positive cells from human umbilical cord blood, Thromb Haemost. 92 (2004) 767-775; M. Yu, Z. Xiao, L. Shen, L. Li, Mid-trimester fetal blood-derived adherent cells share characteristics similar to mesenchymal stem cells but full-term umbilical cord blood does not, Br J Haematol. 124 (2004) 666-675; F. M. Cicuttini, K. Welch, A. W. Boyd, Characterization of CD34+ HLA-DR-CD38+ and CD34+HLA-DR-CD38-progenitor cells from human umbilical cord blood, Growth Factors 10 (1994) 127-134], CB-SC are different by displaying the following characteristics: retention of hematopoietic cell antigen CD45 in long-term culture and expression of both ES cell and hematopoietic cell markers. Additionally, both immunocytochemistry and flow analysis demonstrated that CB-SC are negative for CD34 and macrophage marker CD11b/Mac-1, which is significantly different from the previously reported cord blood monocyte-derived stem cells, f-macrophage [Y. Zhao, T. Mazzone, Human umbilical cord blood-derived f-macrophages retain pluripotentiality after thrombopoietin expansion, Exp Cell Res. 310 (2005) 311-318].

McGuckin et al. isolated SSEA-3$^+$, SSEA-4$^+$, and Oct-4$^+$ ES cell-like cells from a non-hematopoietic cell population (CD45$^-$) of cord blood [C. P. McGuckin, N. Forraz, M. O. Baradez, S, Navran, J. Zhao, R. Urban, R. Tilton, L. Denner, Production of stem cells with embryonic characteristics from human umbilical cord blood, Cell Prolif. 38 (2005) 245-55]. Compared with CB-SC, these cells grew in clumps and did not spread out in microflasks. Importantly, the rarity of this cell in cord blood (about 0.21% of mononuclear cells [C. P. McGuckin, N. Forraz, M. O. Baradez, S, Navran, J. Zhao, R. Urban, R. Tilton, L. Denner, Production of stem cells with embryonic characteristics from human umbilical cord blood, Cell Prolif. 38 (2005) 245-55] poses a key limitation for therapeutic usefulness.

What is meant by "isolated" in the present invention is that the CB-SC are separated from other cells, such as the red blood cells and other unattached mononuclear cells, found in the umbilical cord blood through one or more isolation methods such as, but are not limited to, mechanical separation or selective culturing. The "isolated" CB-SC population does not have to be pure. Other cell types may be present. The other cell types present may be totally different from CB-SC, or they may be transformed from CB-SC during the cell culture and subsequent passage of the cells. In a preferred embodiment, the isolated population is made up of greater than 50% CB-SC. In yet another preferred embodiment, the isolated population is made up of greater than 75% CB-SC. In a further preferred embodiment, the isolated population is made up of greater than 90% CB-SC.

CB-SC Displaying Embryonic Stem (ES) Cell Characteristics

CB-SC in the present invention displays embryonic stem (ES) cell characteristics. What is meant by "embryonic stem cell characteristics" in the present invention is that the stem cells express two critical transcription factors, Oct-4 and Nanog, which are related to the self-renewal and pluripotentiality of ES cells [S. H. Orkin, Chipping away at the Embryonic Stem Cell Network, Cell 122 (2005) 828-830]. In a preferred embodiment, markers characteristic of embryonic stem cell also include other markers such as but are not limited to the stage-specific embryonic antigen SSEA-3 and SSEA-4 [I. Klimanskaya, Y. Chung, L. Meisner, J. Johnson, M. D. West, R. Lanza, Human embryonic stem cells derived without feeder cells, Lancet 365 (2005) 1636-1641]. In yet another preferred embodiment, the "embryonic stem cell characteristics" may further include the weak expression of tumor rejection antigens such as but are not limited to TRA- 1-60 and TRA-1-81. In a further embodiment, the "embryonic stem cell characteristics" may further include no expression of SSEA-1.

In yet another preferred embodiment, the "embryonic stem cell characteristics" can further include expressions of other embryonic stem (ES) cell-related genes, e.g., Zinc finger and SCAN domain containing 10 (ZNF206, also named ZSCAN10), Zic family member 3 heterotaxy 1 (ZIC3), Zic family member 2 (ZIC2), Growth associated protein 43 (GAP43), PR domain containing 14 (PRDM14), Protein tyrosine phosphatase, receptor-type, Z polypeptide 1 (PT-PRZ1), Podocalyxin-like (PODXL), Polyhomeotic homolog 1 (PHC1), and Zinc finger protein 589 (ZNF589).

Immunostaining results (FIG. 1B) showed strong expression of ES cell-specific markers by CB-SC, including the two critical transcription factors Oct-4 and Nanog (related to self-renewal and pluripotentiality of ES cells [S. H. Orkin, Chipping away at the Embryonic Stem Cell Network, Cell 122 (2005) 828-830]), along with stage-specific embryonic antigen (SSEA)-3 and SSEA-4 [I. Klimanskaya, Y. Chung, L. Meisner, J. Johnson, M. D. West, R. Lanza, Human embryonic stem cells derived without feeder cells, Lancet 365 (2005) 1636-1641]. These cells also showed weak expression of tumor rejection antigen TRA-1-60 and TRA-1-81, and no expression of SSEA-1.

CB-SC Displaying Hematopoietic Cell Characteristics

CB-SC of the present invention displays hematopoeitic characteristics, which herein is defined as being positive for the leukocyte common antigen CD45 (CD45 positive, or CD45$^+$). Other markers that also indicate displaying of hematopoietic cell characteristics may include markers such as, but are not limited to, tetraspanin CD9 and stem cell factor receptor CD117.

Cells attached overnight were stained with antibodies to leukocyte common antigen CD45 and other hematopoietic cell markers, along with DAPI staining; Immunostaining CB-SC on day 1 after isolation demonstrated the presence of hematopoietic cell antigens including tetraspanin CD9, leukocyte common antigen CD45, and stem cell factor receptor CD117 (data not shown). The strong expression of CD45 by CB-SC is an indication that these cells are of hematopoietic origin, which are different from many other adult stem cells which are of mesenchymal origin and are CD45 negative (CD45$^-$).

CB-SC Phenotypically Different from Hematopoietic Stem Cells

CB-SC are phenotypically different from hematopoeitic stem cells. Hematopoeitic stem cells are characterized by being positive for the CD34 marker (CD34$^+$). Immunostaining studies indicated that CB-SC are CD34 negative (CD34$^-$) (FIG. 1B), and, therefore, are phenotypically different from hematopoeitic stem cells.

CB-SC Phenotypically Different from Lymphocytes, Macrophages and Monocytes

CB-SC do not express human monocyte/macrophage specific antigens CD14 and CD11b/Mac-1, T lymphocyte marker CD3, or B lymphocyte marker CD20 (data not shown). These results indicate that CB-SC are phenotypically distinct from lymphocytes, macrophages and monocytes, and CB-SC are not monocyte-derived.

CB-SC Displaying Low Immunogenicity and Immune Regulation

Figure 3:
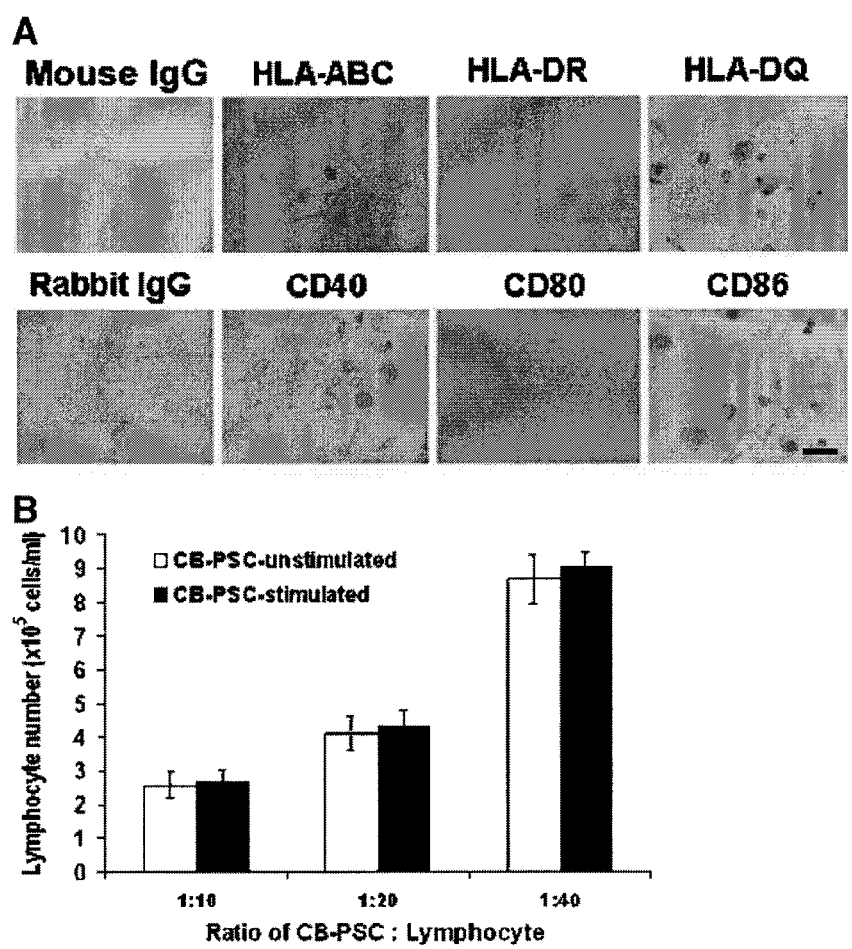
FIG. 3 is the evaluation of the immunogenicity of CB-SC. (A) Examination of immune-associated markers on CB-SC. Immunostaining results were obtained from four cord blood preparations and yielded the similar results. Normal rabbit IgG served as negative for HLA-ABC polyclonal antibody; Isotype-matched mouse IgG antibody served as negative control for other monoclonal antibodies. Scale bar, 47 μm. (B) Mixed lymphocyte reaction (MLR). CB-SC were cocultured with allogeneic lymphocytes from peripheral blood for 6 days at different ratios. Cell number represents mean (±SD) of three experiments.

A major concern using stem cells for therapeutics is their immunogenicity, leading to immune rejection. Cellular immunogenicity is mainly determined by the major histocompatibility complex (MHC) including MHC class 1 molecule (HLA-ABC) and MHC Class II molecules (HLA-DR and HLA-DQ) [Drukker, G. Katz, A. Urbach, M. Schuldiner, G. Markel, J. Itskovitz-Eldor, B. Reubinoff, O. Mandelboim, N. Benvenisty, Characterization of the expression of MHC proteins in human embryonic stem cells, Proc Natl Acad Sci USA. 99 (2002) 9864-9869]. As shown in Example 4 below, immunostaining for two critical MHC molecules demonstrated that only 5% of cells expressed HLA-ABC, and HLA-DR was completely negative (FIG. 3A). These levels of expression are similar to levels of expression reported in human ES cells [Drukker, G. Katz, A. Urbach, M. Schuldiner, G. Markel, J. Itskovitz-Eldor, B. Reubinoff, O. Mandelboim, N. Benvenisty, Characterization of the expression of MHC proteins in human embryonic stem cells, Proc Natl Acad Sci USA. 99 (2002) 9864-9869]. Approximately 6% of cells showed weak expression for CD40 and CD80; ≈30% of cells expressed HLA-DQ; ≈22% of cells expressed CD86 (FIG. 3A).

Low immunogenicity of CB-SC can also be readily demonstrated with a functional analysis using the mixed lymphocyte reaction as described in Example 5 below. As shown in FIG. 3B, CB-SC did not stimulate lymphocyte proliferation in an allogeneic mixed lymphocyte reaction, consistent with low immunogenicity demonstrated by immunostaining.

Not to be bound by any specific theory, the low immunogenicity of CB-SC can contribute to the ability of CB-SC to regulate T-lymphocytes. Following co-culture of T lymphocytes with CB-SC the T lymphocytes amount of inflammatory cytokines produces by the T cells was reduced 2-3 fold, while the amount of TGF-β1 was increased by 2-3 fold. Examples of inflammatory cytokines that were reduced by co-culture with CB-SC include TNF-α, IL-β, IL-γ, IL-15, IL-17, IL-18, IL1β, IL-21, IL22, IL-23, IL-4, IL-5, and IL-6. As shown in Example 7 below, CB-SC, when cocultured with allogeneic peripheral blood lymphocytes in the presence of the mitogen phytohaemagglutinin (PHA) or physiological growth factor interleukin (IL)-2, decreases the percentage of PHA-stimulated CD8$^+$ T cells and IL-2-stimulated CD4$^+$ CD25$^+$ regulatory T cells, along with normalization of the CD4/CD8 ratio and decreasing of intracellular IL-10 level. CD69 molecule, a negative regulator on activated T lymphocytes, was significantly increased on both CD4$^+$ and CD8$^+$ T lymphocytes after coculture with CB-SC (FIG. 4). In addition, CB-SC significantly inhibits the proliferation of IL-2- and/or PHA-stimulated lymphocytes. Mechanism studies showed that nitric oxide (NO) partially mediated this inhibitory effect, as demonstrated by blocking with a powerful nitric oxide synthase inhibitor (N-omega-nitro-L-arginine, L-NNA). Cell-cell contacting play a critical role in IL-2 treatment, as demonstrated by using transwell culture system (FIG. 5A). Furthermore, mechanistic studies demonstrated that CB-SC-produced nitric oxide (NO) contributes to the modulation of CB-SC on regulatory T lymphocytes. The epigenetic regulation on DNA methyltransferase (DNMT) activity of lymphocytes by CB-SC-derived NO can be significantly blocked by presence of a specific inducible nitric oxide synthase (iNOS) inhibitor 1400 W (FIG. 5B).

CB-SC have the Capability for Proliferation

One of the key characteristics for a stem cell to be suitable for stem cell-based therapy is its capability for proliferation. As used herein, the term "capability for proliferation" refers that the cell expresses one or more self-renewal markers such as but are not limited to Nanog and the cell can proliferate. Preferably, the cell can proliferate indefinitely. What is meant by "proliferate" as used in the present disclosure is that the cell can grow and multiply in numbers when the cell is cultured. The terms "proliferate" and "expand" are used interchangeably herein.

As indicated by immunostaining studies (FIG. 1B), CB-SC are positive for the critical transcription factor Nanog related to self-renewal of ES cells. These cells are found to be able to proliferate with an estimated doubling time of 2.8 days based on a growth curve generated over 12 days (FIG. 1A). Using the growth conditions in Example 1 shown below, CB-SC can be passaged up to a total of 7 passages over 2 months with the cells passaged every 5 to 7 days. However, it is likely that further optimization of growth conditions may improve their potential for longer term proliferation.

CB-SC have the Ability to Differentiate to Multiple Types of Cells

Another key characteristic for a stem cell to be suitable for stem-cell therapy has the ability to differentiate to multiple types of cells. Preferably, the stem cell is pluripotent. Our data indicate that CB-SC, upon appropriate stimulations, can differentiate into a wide variety of types of cells with characteristics of three embryonic layers (mesoderm, ectoderm and endoderm), which include endothelial-like cells (which are mesoderm-derived [L. M. Hoffman, M. K. Carpenter, Characterization and culture of human embryonic stem cells, Nat Biotechnol. 23 (2005) 699-708; M. Baron, Induction of embryonic hematopoietic and endothelial stem/progenitor cells by hedgehog-mediated signals, Differentiation 68 (2001) 175-185]), neuronal-like cells (which are ectoderm-derived [L. M. Hoffman, M. K. Carpenter, Characterization and culture of human embryonic stem cells, Nat Biotechnol. 23 (2005) 699-708; L. Bally-Cuif, M. Hammerschmidt, Hammerschmidt. Induction and patterning of neuronal development, and its connection to cell cycle control, Curr Opin Neurobiol. 13 (2003) 16-25]), and insulin-producing cells (which are endoderm-derived [M. A. Hussain, N. D. Theise, Stem-cell therapy for diabetes mellitus, Lancet 364 (2004) 203-205; L. M. Hoffman, M. K. Carpenter, Characterization and culture of human embryonic stem cells, Nat Biotechnol. 23 (2005) 699-708]). Other cells that CB-SC can differentiate to include oligodendrocytes and megakaryocyte-like cells. It is very likely that CB-SC can differentiate to other types of cells as well.

As shown in Example 4 below (FIG. 1B), CB-SC is positive for both Oct-4 and Nanog which are critical transcription factors related to pluripotency. Therefore, it is reasonable to speculate that CB-SC are pluripotent.

CB-SC are Suitable for Stem Cell-Based-Therapies

The present invention provides a composition for stem cell-based therapies comprising CB-SC. The present invention further provides a method for stem cell-based therapies by the use CB-SC.

Embryonic stem (ES) cells display two unique properties: capability to proliferate and pluripotentiality for differentiation [A. Vats, R. C. Bielby, N. S. Tolley, R. Nerem, J. M. Polak, Stem cells, Lancet 366 (2005) 592-602]. Stem cell-based therapy, therefore, has significant potential to cure important, and common, human diseases [M. A. Hussain, N. D. Theise, Stem-cell therapy for diabetes mellitus, Lancet 364 (2004) 203-205; C. M. Rice, N. J. Scolding, Adult stem cells—reprogramming neurological repair? Lancet 364 (2004) 193-199]. However, a major limitation for stem cell-based therapy has been identification of a suitable source of stem cells. For instances, there are significant ethical issues for use of ES cells [C. Dennis, Check E, 'Ethical' routes to stem cells highlight political divide, Nature 437 (2005) 1076-1077; M. Evans, Ethical sourcing of human embryonic stem cells—rational solutions? Nat Rev Mol Cell Biol. 6 (2005) 663-667] and adult stem cells display reduced proliferation and differentiation ability [C. M. Rice, N. J. Scolding, Adult stem cells—reprogramming neurological repair? Lancet 364 (2004) 193-199].

CB-SC share the same key characteristics of embryonic stem cells in capability to proliferate and pluripotentiality for differentiation. Combining with their low immunogenicity, CB-SC are suitable for stem cell-based therapies in treatment of human diseases. In addition, CB-SC are readily available from umbilical cord blood, and they can be cultured and propagated in vitro to provide an abundant supply of cells for stem cell-based therapies. These properties of CB-SC can overcome the problem of inadequate availability and supply associated with ES cells and other adult stem cells displaying reduced proliferation and differentiation ability.

Use of CB-SC for Treating Hyperglycemia in Diabetic Subjects

The present invention further provides a method for treating hyperglycemia in a diabetic mammalian subject by administering CB-SC to a subject (ex., a diabetic mammalian subject). The administered CB-SC migrate to the pancreas of the subject and differentiate to functional insulin-producing cells in vivo, which in turn produce insulin in response to the high glucose level to control hyperglycemia in the subject.

Diabetes and its long-term complications are increasing in prevalence posing an important therapeutic challenge for individual patients and public health. Deficit of insulin-producing cells is the crucial issue for both type 1 and type 2 diabetic patients. In spite of the development and application of various insulin formulations, exogenous insulin neither achieves the same degree of glycemic control as that provided by endogenous insulin, nor completely prevents the long-term complications such as diabetic retinopathy, neuropathy, nephropathy, and diverse cardiovascular disorders [M. A. Hussain, N. D. Theise, Stem-cell therapy for diabetes mellitus, Lancet 364 (2004) 203-205]. These clinical challenges necessitate the development of more efficient treatments. Islet cell transplantation, a potential treatment, has been limited by a shortage of pancreas as a source of purified islets. Stem cell-derived insulin-producing cells, therefore, provide a promising approach for beta cell-replacement therapy [M. A. Hussain, N. D. Theise, Stem-cell therapy for diabetes mellitus, Lancet 364 (2004) 203-205]. Accumulating evidence suggests that insulin-producing cells derived from stem cells can normalize blood glucose in diabetic animal models [M. A. Hussain, N. D. Theise, Stem-cell therapy for diabetes mellitus, Lancet 364 (2004) 203-205]. However, in previous reports these cells were derived from ES cells and fetal tissues [G. K. Brolen, N. Heins, J. Edsbagge, H. Semb, Signals from the embryonic mouse pancreas induce differentiation of human embryonic stem cells into insulin-producing beta-cell-like cells, Diabetes 54 (2005) 2867-2874; Y. Hori, I. C. Rulifson, B. C. Tsai, J. J. Heit, J. D. Cahoy, S. K. Kim, Growth inhibitors promote differentiation of insulin-producing tissue from embryonic stem cells, Proc Natl Acad Sci USA. 99 (2002) 16105-16110; H. Segev, B. Fishman, A. Ziskind, M. Shulman, J. Itskovitz-Eldor, Differentiation of human embryonic stem cells into insulin-producing clusters, Stem Cells 22 (2004) 265-274; S. Miyazaki, E. Yamato, J. Miyazaki, Regulated expression of pdx-1 promotes in vitro differentiation of insulin-producing cells from embryonic stem cells, Diabetes 53 (2004) 1030-1037; M. Zalzman, L. Anker-Kitai, S. Efrat, Differentiation of human liver-derived, insulin-producing cells toward the beta-cell phenotype, Diabetes 54 (2005) 2568-2575; M. Zalzman, S. Gupta, R. K. Giri, I. Berkovich, B. S. Sappal, O. Karnieli, M. A. Zem, N. Fleischer, S. Efrat, Reversal of hyperglycemia in mice by using human expandable insulin-producing cells differentiated from fetal liver progenitor cells, Proc Natl Acad Sci USA. 100 (2003) 7253-7258], raising ethical concerns for their clinical application. CB-SC can correct hyperglycemia in diabetic mice, and restore euglycemia after an acute glucose challenge (IPGTT).

Figure 12:
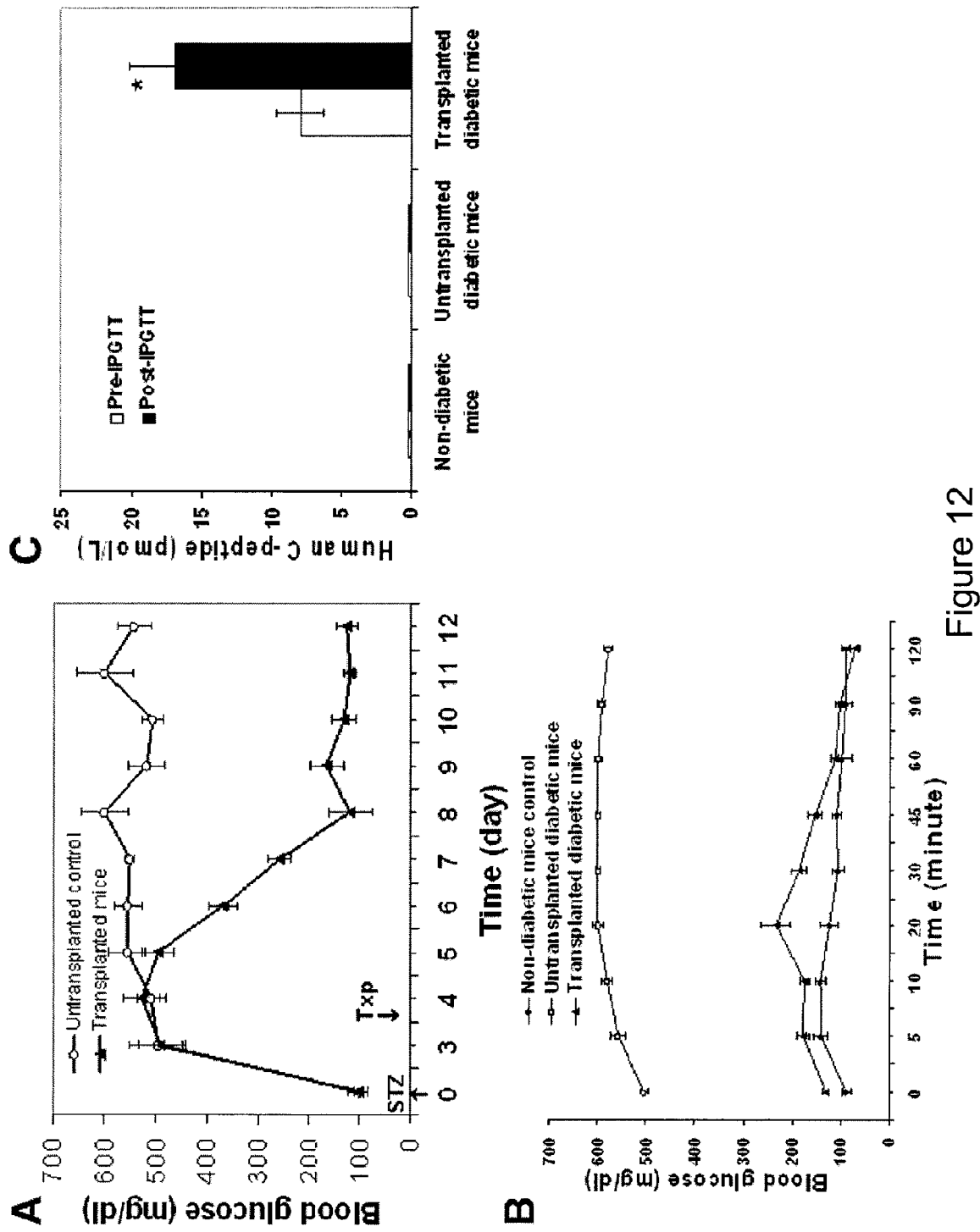
FIG. 12 shows that CB-SC differentiated into functional insulin-producing cells after transplantation into streptozotocin (STZ)-induced diabetic mice. (A) Kinetic examination showed decreasing of blood glucose levels post transplantation (Txp). N=7 for CB-SC-transplanted mice; n=8 for untransplanted diabetic mice. Glucose levels were measured from whole tail vein blood using an AccuChek glucose detector. (B) Intraperitoneal glucose tolerance testing (IPGTT) after 7 days following transplantation. N=3 for CB-SC-transplanted mice; n=4 for untransplanted diabetic mice, and n=3 for non-diabetic mice. (C) Human C-peptide detection in the sera of transplanted mice. Blood samples were collected during 20 min before and after IPGTT. N=3 for each group. Human C-peptide was examined by using an ultrasensitive human C-peptide enzyme-linked immunosorbent assay (ELISA) kit. Data represent mean (±SD). Asterisk (*) represents for p value<0.05.

As shown in Example 10 below, CB-SC injected into the peritoneal cavity of STZ-induced diabetic mice has the capability to correct hyperglycemia in these mice. Further, intraperitoneal glucose tolerance testing (IPGTT) demonstrated physiological responses of transplanted CB-SC cells. Blood glucose of normal non-diabetic mice peaked between 5-10 min and returned to normal level 30 min following glucose challenge. Blood glucose of CB-SC-transplanted diabetic mice peaked at 20 min, followed by a return to normal range after 60 min (FIG. 10B). However, blood glucose of CB-SC-untransplanted diabetic mice remained very high (>500 mg/dl) (FIG. 12B).

To substantiate that this reversal of hyperglycemia was associated with differentiation of CB-SC into insulin-producing cells, we also examined the production of human C-peptide (as an indicator of human insulin secretion) in the sera of CB-SC-transplanted diabetic mice. Human C-peptide production was undetectable in the sera of non-diabetic mice and untransplanted diabetic mice, but acutely increased in transplanted mice following glucose challenge. These results, in aggregate, provide evidence that CB-SC give rise to functional insulin-producing cells after transplantation into diabetic mice. This conclusion is supported by a recent report, which showed cord blood may contain progenitors that generate insulin-producing cells [S. Yoshida, F. Ishikawa, N. Kawano, K. Shimoda, S, Nagafuchi, S. Shimoda, M. Yasukawa, T. Kanemaru, H. Ishibashi, L. D. Shultz, M. Harada, Human cord blood—derived cells generate insulin-producing cells in vivo, Stem Cells 23 (2005) 1409-1416].

Generation of Lymphocyte Vaccine by Use of CB-SC in Preventing Autoimmune Disease.

The present invention provides a composition and method for preventing an autoimmune disease in a mammalian subject. The composition comprises the CB-SC of the present disclosure. An example of the autoimmune disease is type 1 diabetes. In an embodiment, lymphocytes are treated with CB-SC by coculturing the lymphocytes with CB-SC to obtain a vaccine of CB-SC-treated lymphocyte. An effective dose of the vaccine is then administered to a subject for preventing the autoimmune disease. Preferably, the CB-SC-treated lymphocytes are harvested from the coculture before administering to the subject. As illustrated in Example 15 below, vaccination with CB-SC-treated lymphocytes protect NOD mice for developing type 1 diabetes. It is important that the lymphocytes used in the present invention be histocompatible with the subject receiving the lymphocyte vaccine to avoid immune rejection. For clinical applications, lymphocytes may be obtained from the peripheral blood of the subject. It is preferable to use autologous lymphocytes as vaccines to treat autoimmune disease like type 1 diabetes to avoid immune rejection. In a further embodiment, the CB-SC can be administered directly to the subject to treat the lymphocytes in vivo within the subject to generate the lymphocyte vaccine for preventing the autoimmune disease.

Use of CB-SC to Treat Autoimmue Disease

In a still further embodiment, the present invention discloses a composition and method for treating autoimmune disease in a mammalian subject. The composition comprises the CB-SC of the present disclosure. An example of the autoimmune disease is type 1 diabetes. In an embodiment, an effective dose of the CB-SC is administered to a subject diagnosed with the autoimmune disease to treat the autoimmune disease. As illustrated in Example 16 below, CB-SC administered to diabetic mice with type 1 diabetes reduced the incidence of type 1 diabetes in the diabetic mice as compared to control not receiving the CB-SC treatment.

CB-SC Can Differentiate into Different Cell Types

CB-SC can differentiate into different cell types with and without the use of an inducer. In another aspect, the invention discloses a method of directing cell differentiation of embryonic-like stem cells by incubating the embryonic-like stem cells of the present invention with an inducer, wherein the inducer directs maturation of the embryonic-like stem cells into a defined population of cells. Non-limiting examples of inducers include Exendin-4, granulocyte monocyte colony stimulating factor (GM-CSF), granulocyte-macrophage colony-stimulating, nerve growth factor (NGF), 5-Aza-2'-deoxycytidine, retinoic acid (RA), dimethyl sulfoxide (DMSO), thrombopoietin, hepatocyte growth factor (HGF), vascular endothelial growth factor isoform165 (VEGF165), epidermal growth factor (EGF), erythropoietin (EPO), interleukin-2 (IL-2), IL-5, IL-7, IL-18, interferon-gamma, granulocyte-macrophage colony-stimulating factor (GM-CSF), macrophage colony-stimulating factor (M-CSF), phorbol 12-myristate 13-acetate (PMA), lipopolysaccharide (LPS), granulocyte colony-stimulating factor (G-CSF), all trans-retinoic acid (ATRA), vitaminD3, bone morphogenetic proteins (BMPs), brain derived neurotrophic factor (BDNF), glial derived neurotrophic factor (GDNF), growth factors, fibroblast growth factor (FGF), transforming growth factors (TGF), ciliary neurotrophic factor (CNTF), leukemia inhibitory factor (LIF), glial growth factor (GGF), tumor necrosis factors (TNF), interferon, insulin-like growth factors (IGF), colony stimulating factors (CSF), KIT receptor stem cell factor (KIT-SCF), interferon, triiodothyronine, thyroxine, erythropoietin, silencers, SHC(SRC-homology-2-domain-containing transforming protein), neuroproteins, proteoglycans, glycoproteins, neural adhesion molecules, and other cell-signalling molecules and mixtures, thereof. The defined population of cells can have properties of cells from the following non-limiting examples of cells: beta cell-like insulin-producing cells, neuronal cells, cardiomyocyte cells, megakaryocyte cells, endothelial cells, epithelial cells, red blood cells, lymphocytes, monocytes, macrophages, granulocytes, hepatocytes, nephrogenic cells, adipogenic cells, osteoblast cells, osteoclastic cells, alveolar cells, cardiac cells, intestinal cells, renal cells, and retinal cells. Differentiating can be carried out by transducing the cells with a vector that contains a nucleic acid encoding the inducer and expresses the inducer in the cells. The vector can be a plasmid, cosmid, bacteriophage, DNA virus, RNA virus, or retrovirus vector.

In one preferred embodiment, the differentiating step is carried out by transducing (sometimes also referred to as "engineering" or "transforming") the cells with a vector, or introducing into the cells a vector, that contains a nucleic acid encoding an inducer and expresses the inducer in the cells, or by activating the expression of an endogeneous nucleic acid encoding an inducer in the cells (e.g., engineering the cells to activate transcription of an endogeneous such as granulocyte monocyte colony stimulating factor (GM-CSF), granulocyte-macrophage colony-stimulating, nerve growth factor (NGF), retinoic acid (RA), thrombopoietin, hepatocyte growth factor (HGF), epidermal growth factor (EGF), erythropoietin (EPO), interleukin-2 (IL-2), IL-5, IL-7, IL-18, interferon-gamma, granulocyte-macrophage colony-stimulating factor, etc., such as by inserting a heterologous promoter in operative associated with an endogeneous differentiation factor, in accordance with known techniques. See, e.g., U.S. Pat. No. 5,618,698). Such exogenous nucleic acids may be of any suitable source, typically mammalian, including but not limited to rodent (mouse, hamster, rat), dog, cat, primate (human, monkey), etc.

For recombinant techniques any suitable vector may be used, including plasmids, cosmids, bacteriophages, DNA viruses, RNA viruses and retroviruses, all of which are known for the expression of a heterologous nucleic acid in stem cells, progenitor cells, etc., in substantially the same manner as known. See, e.g., U.S. Pat. Nos. 6,392,118; 6,309,883; 6,258,354; and 4,959,313. Such adenovirus vectors are also known and can be utilized in accordance with known techniques. See, e.g., U.S. Pat. Nos. 6,544,780; 6,503,498; 5,981,225; and 5,670,488; Since transient expression is useful in carrying out the present invention, the vector may be simply "naked", or linear, DNA. The vector should include a suitable promoter (such as an SV40 promoter, retrovirus LTR-promoter, or cytomegalovirus (CMV) promoter), operatively associated with the nucleic acid to constituitively express, or inducibly express, the differentiation factor in the cells. Expression may be stable expression or transient expression depending upon the specific system chosen, with transient expression currently preferred.

The cells can be protected from immune rejection by modifying cell expression of selected proteins in accordance with known techniques. See, e.g., US Patent Application 2002/0182728. For example, the cultured transdifferentiated cells can be transformed to express a protein or peptide which will inhibit or prevent the destructive immune process. Other useful proteins or peptides may be expressed. In addition, expression of autoantigens specific to the IDD process, such as GAD, 64 kD islet cell surface antigens, to the extent they may be expressed by the transdifferentiated cells, or any other markers identified on the cells, can be eliminated by standard gene knock-out or selection procedures to produce cells which are not or are less susceptible to autoimmune attack. Methods for producing such mutant or knock out cells are well known in the art and include, for example, homologous recombination methods disclosed in U.S. Pat. No. 5,286,632; U.S. Pat. No. 5,320,962; U.S. Pat. No. 5,342,761; and in WO 90/11354; WO 92/03917; WO 93/04169; WO 95/17911, all of which are herein incorporated in their entirety by reference. In addition, a universal donor cell is produced by preparing transdifferentiated cells modified so as not to express human leukocyte antigen (HLA) markers.

If desired, the cells can be frozen or cryopreserved prior to use, and then thawed to a viable form. Methods of freezing or cryopreserving cells (for subsequent return to viable form) are well known in the art. For example, cryopreservation of cells can involve freezing the cells in a mixture of a growth medium and another liquid that prevents water from forming ice crystals, and then storing the cells at liquid nitrogen temperatures (e.g., from about −80 to about −196° C.). See, e.g., U.S. Pat. No. 6,783,964 to Opara.

Formulations and Administration

CBSC or their differentiated progeny can be administered to a subject by a several methods available to the art, including but not limited to localized injection, catheter administration, systemic injection, intraperitoneal injection, parenteral administration, intracranial injection, intra-arterial injection, intravenous injection, intraplacental injection, intrauterine injection, intrathecal administration, intraventricular administration, intracisternal injection, intrastriatal administration, intranigral administration, intramuscular injection, surgical injection into a tissue of interest or via direct application to tissue surfaces (e.g., during surgery or on a wound).

A method to potentially increase cell survival is to incorporate CBSC or other cells of interest (ex. CD62L+ T cells, CD8+CD62L+ T cells, CD4+CD62L+ T cells, etc.) into a biopolymer or synthetic polymer. Depending on the patient's condition, the site of injection might prove inhospitable for cell seeding and growth because of scarring or other impediments. Examples of biopolymer include, but are not limited to cells mixed with fibronectin, fibrin, fibrinogen, thrombin, collagen, and proteoglycans. This could be constructed with or without included cytokines, differentiation factors, angiogenesis factors and/or anti-apoptosis factors. Additionally, these could be in suspension. Another alternative is a three-dimension gel with cells entrapped within the interstices of the cell biopolymer admixture. Again cytokines, differentiation factors, angiogenesis factors and/or anti-apoptosis factors could be included within the gel. These could be deployed by injection via various routes described herein, via catheters or other surgical procedures.

The quantity of cells to be administered will vary for the subject being treated. In a preferred embodiment, between about $10^3$ to about $10^9$, more preferably about $10^4$ to about $10^8$, more preferably about $10^5$ to about $10^7$ CBSC can be administered to a human subject. The precise determination of what would be considered an effective dose may be based on factors individual to each patient, including their size, age, disease or injury, size of damage caused by the disease or injury and amount of time since the damage occurred.

When administering a therapeutic composition of the present invention, it will generally be formulated in a unit dosage injectable form (solution, suspension, emulsion). The doses may be single doses or multiple doses over a period of several days. The pharmaceutical formulations suitable for injection include sterile aqueous solutions and dispersions. The carrier can be a solvent or dispersing medium containing, for example, water, saline, phosphate buffered saline, polyol (for example, glycerol, propylene glycol, liquid polyethylene glycol, and the like) and suitable mixtures thereof.

Additionally, various additives which enhance the stability, sterility, and isotonicity of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, sorbic acid, and the like. In many cases, it will be desirable to include isotonic agents, for example, sugars, sodium chloride, and the like. Prolonged absorption of the injectable pharmaceutical form can be brought about by the use of agents delaying absorption, for example, aluminum monostearate and gelatin. According to the present invention, however, any vehicle, diluent, or additive used would have to be compatible with the cells.

Sterile injectable solutions can be prepared by incorporating the cells utilized in practicing the present invention in the required amount of the appropriate solvent with various amounts of the other ingredients, as desired.

In one embodiment, CBSCs can be administered initially, and thereafter maintained by further administration of CBSCs. For instance, CBSCs can be administered by one method of injection, and thereafter further administered by a different or the same method. In other embodiments, various populations of T lymphocytes that were isolated following co-culturing with CBSC can be administered to a subject. For example, CD8+CD62L+ and/or CD4+CD62L+ T cells can be administered initially, and thereafter maintained by further administration of CD8+CD62L+ and/or CD4+CD62L+ T cells. For instance, the CD8+CD62L+ and/or CD4+CD62L+ T cells can be administered by one method of injection, and thereafter further administered by a different or the same method.

Examples of compositions comprising CBSCs or various populations of T cells that are positive for the CD62L marker, include liquid preparations for administration, including suspensions; and, preparations for direct or intravenous administration (e.g., injectable administration), such as sterile suspensions or emulsions. Such compositions may be in admixture with a suitable carrier, diluent, or excipient such as sterile water, physiological saline, glucose, dextrose, or the like. The compositions can also be lyophilized. The compositions can contain auxiliary substances such as wetting or emulsifying agents, pH buffering agents, gelling or viscosity enhancing additives, preservatives, flavoring agents, colors, and the like, depending upon the route of administration and the preparation desired. Standard texts, such as Remington, The Science And Practice of Pharmacy (9.sup.th Ed. 1995), incorporated herein by reference, may be consulted to prepare suitable preparations, without undue experimentation. In the manufacture of a pharmaceutical formulation according to the invention, the cells are typically admixed with an acceptable carrier. The carrier must, of course, be acceptable in the sense of being compatible with any other ingredients in the formulation and must not be deleterious to the patient. The carrier may be a solid or a liquid, or both (e.g., hydrogels), and may be formulated with the cells as a unit-dose formulation. In one embodiment the cells are provided as a suspension in the carrier to reduce clumping of the cells.

Compositions of the invention are conveniently provided as liquid preparations, e.g., isotonic aqueous solutions, suspensions, emulsions or viscous compositions, which may be buffered to a selected pH. Liquid preparations are normally easier to prepare than gels, other viscous compositions, and solid compositions. Additionally, liquid compositions are somewhat more convenient to administer, especially by injection. Viscous compositions, on the other hand, can be formulated within the appropriate viscosity range to provide longer contact periods with specific tissues.

The choice of suitable carriers and other additives will depend on the exact route of administration and the nature of the particular dosage form, e.g., liquid dosage form (e.g., whether the composition is to be formulated into a solution, a suspension, gel or another liquid form, such as a time release form or liquid-filled form).

Solutions, suspensions and gels normally contain a major amount of water (preferably purified, sterilized water) in addition to the cells. Minor amounts of other ingredients such as pH adjusters (e.g., a base such as NaOH), emulsifiers or dispersing agents, buffering agents, preservatives, wetting agents and jelling agents (e.g., methylcellulose), may also be present. The compositions can be isotonic, i.e., they can have the same osmotic pressure as blood and lacrimal fluid.

The desired isotonicity of the compositions of this invention may be accomplished using sodium chloride, or other pharmaceutically acceptable agents such as dextrose, boric acid, sodium tartrate, propylene glycol or other inorganic or organic solutes. Sodium chloride is preferred particularly for buffers containing sodium ions.

Viscosity of the compositions, if desired, can be maintained at the selected level using a pharmaceutically acceptable thickening agent. Methylcellulose is preferred because it is readily and economically available and is easy to work with. Other suitable thickening agents include, for example, xanthan gum, carboxymethyl cellulose, PVA, ethyl cellulose, hydroxypropyl cellulose, carbomer, and the like. The preferred concentration of the thickener will depend upon the agent selected and the desired viscosity. Viscous compositions are normally prepared from solutions by the addition of such thickening agents.

A pharmaceutically acceptable preservative or cell stabilizer can be employed to increase the life of the compositions. Preferably, they will not affect the viability or efficacy of the cells as described in the present invention.

Compositions can be administered in dosages and by techniques available to those skilled in the medical and veterinary arts taking into consideration such factors as the age, sex, weight, and condition of the particular subject, and the composition form used for administration (e.g., solid vs. liquid).

Matrices are also used to deliver cells of the present invention to specific anatomic sites, where particular growth factors incorporated into the matrix, or encoded on plasmids incorporated into the matrix for uptake by the cells, can be used to direct the growth of the initial cell population. DNA can be incorporated within pores of the matrix, for example, during the foaming process used in the formation of certain polymer matrices. As the polymer used in the foaming process expands, it entraps the DNA within the pores, allowing controlled and sustained release of plasmid DNA. Such a method of matrix preparation is described by Shea, et al. (Nature Biotechnology (1999) 17: 551-554).

Plasmid DNA encoding cytokines, growth factors, or hormones can be trapped within a polymer gene-activated matrix carrier, as described by Bonadio, J., et al. (Nature Medicine (1999) δ: 753-759). The biodegradable polymer is then implanted near the brain or other neural tissue, where CBSCs are implanted and take up the DNA, which causes the CBSCs to produce a high local concentration of the cytokine, growth factor, or hormone, accelerating healing of the damaged tissue.

In some embodiments, the CBSCs, and/or various populations of T cells expressing the CD62L marker, are encapsulated. One goal in encapsulation in cell therapy is to protect allogeneic and xenogeneic cell transplants from destruction by the host immune response, thereby eliminating or reducing the need for immuno-suppressive drug therapy. Techniques for microencapsulation of cells are available to the art (see, for example, Chang, P., et al., Trends in Biotech. 1999; 17:78-83; Matthew, H. W., et al., ASAIO Trans. 1991; 37(3):M328-30; Yanagi, K., et al., ASAIO Trans. 1989; 35(3):570-2; Cai Z. H., et al., Artif Organs. 1988; 12(5):388-93; Chang, T. M., Artif Organs. 1992; 16(1):71-4). Materials for microencapsulation of cells include, for example, polymer capsules, dendrimer, liposome, alginate-poly-L-lysine-alginate microcapsules, barium poly-L-lysine alginate capsules, barium alginate capsules, polyacrylonitrile/polyvinylchloride (PAN/PVC) hollow fibers, and polyethersulfone (PES) hollow fibers. U.S. Pat. No. 5,639,275, for example, describes improved devices and methods for long-term, stable expression of a biologically active molecule using a biocompatible capsule containing genetically engineered cells.

For the purposes described herein, either autologous, allogeneic or xenogenic CBSCs of the present invention can be administered to a subject, either in differentiated or undifferentiated form, genetically altered or unaltered, by direct injection to a desired site, systemically, on or around the surface of an acceptable matrix, or in combination with a pharmaceutically acceptable carrier.

Following transplantation, the growth and/or differentiation of the administered CBSCs or progeny, or various T cell populations expressing the CD62L marker, and the therapeutic effect of the CBSCs or progeny, or various T cell populations expressing the CD62L marker, may be monitored. For example, the functionality of CBSCs administered to treat damaged neuronal tissue may be monitored by analyzing behavioral studies before an after administration of the CBSCs, or the functionality of CBSCs, or various T cell populations expressing the CD62L marker, administered to treat diabetes by monitoring blood glucose and/or insulin levels.

Following administration, the immunological tolerance of the subject to the CBSCs or progeny derived therefrom various T cell populations expressing the CD62L marker can be tested by various methods known in the art to assess the subject's immunological tolerance to the cells. In cases where subject's tolerance of the cells is suboptimal (e.g., the subject's immune system is rejecting the exogenous CBSCs), therapeutic adjunct immunosuppressive treatment, which is available to the art, of the subject may be performed.

EXAMPLES

This invention is further illustrated by the following examples which should not be construed as limiting. The following experiments were performed to demonstrate various aspects of the invention. Statistical analyses of data in the following examples were performed by the paired Student's t-test to determine statistical significance. Values are given as mean±SD (standard deviation).

Mouse anti-human monoclonal antibodies to CD3, CD9, CD11b/Mac-1 (Clone ICRF44), CD14, FITC-conjugated CD14 (clone M5E2), CD20, CD31, CD34 (clone 563), R-PE-conjugated mouse anti-human CD34 monoclonal antibody (clone 563), CD45 (clone HI30), FITC-conjugated CD45, human leukocyte antigen (HLA)-DR, HLA-DQ, HLAABC, isotype-matched antibody IgG1κ, and FITC-conjugated IgG were purchased from BD Pharmingen (San Diego, Calif.). Mouse monoclonal antibodies to human CD40, CD80 (B7-1), CD86 (B7-2), CXCR4, and rabbit anti-mouse CXCL12 alpha subunit (SDF-1α) were from eBioscience (San Diego, Calif.). Mouse anti-human Thy-1 (CD90), embryonic transcription factor Oct-4 monoclonal antibodies, rabbit anti-human embryonic transcription factor Nanog and alpha 1C (Cav1.2) polyclonal antibodies were from Chemicon International Inc. (Temecula, Calif.). Rabbit anti-human polyclonal antibody CD117 was from NeoMarkers. Rabbit anti-human polyclonal antibodies: PDX-1, NeuroD, NKX6.1, Glut-2, Sur1, glucokinase regulator protein (GCKR) and normal rabbit IgG were from Santa Cruz Biotechnology (Santa Cruz, Calif.); PC-1 (also named PC1/3) and PC-2 were from Abcam (Cambridge, Mass.). Recombinant human macrophage colony-stimulating factor (M-CSF), mouse anti-human insulin, and anti-glucagon monoclonal antibodies were purchased from Sigma (St. Louis, Mo.). FITC- or Rhodamine (TRITC)-labeled AffiniPure Donkey anti-mouse IgG antibody was obtained from Jackson ImmunoResearch Laboratories (West Grove, Pa.). Alexa Fluor 568-labeled goat anti-rabbit IgG (H+L) highly cross-adsorbed second antibody and Zymosan A BioParticles were from Molecular Probes (Eugene, Oreg.).

Example 1

Isolation of Cord Blood-Stem Cells (CB-SC) from Human Umbilical Cord Blood and Cell Culture Cell Culture Human umbilical cord blood samples (50-100 ml/unit) were obtained from healthy donors (Life-Source Blood Services, Glenview, Ill.). Mononuclear cells were isolated using Ficoll-Hypaque ($\gamma$=1.077, Sigma), followed by removing red blood cells using Red Blood Cell Lysis buffer (eBioscience, San Diego, Calif.). Mononuclear cells were seeded into 8-Well Lab-Tek II Chamber Slides (Fisher Scientific) at 1-2× $10^5$ cells/ml, 0.5 ml/well in RPMI 1640 medium supplemented with 7% fetal bovine serum (Invitrogen, Carlsbad, Calif.), and incubated at 37° C., 8% $CO_2$ conditions. Cells at 70-80% confluence were passaged every 5-7 days with the fresh RPMI 1640 medium supplemented with 7% fetal bovine serum at ratio 1:2. To expand cells on a large scale, mononuclear cells were initially seeded in 150×15 mm Petri dishes (Becton Dickinson Labware, Franklin Lakes, N.J.) at 1×$10^6$ cells/ml, 25 ml/dish in RPMI 1640 medium supplemented with 7% fetal bovine serum. Cells were passaged every 10-14 days at a ratio of 1:2. Because CB-SC tightly adhered to the culture dishes, they were resistant to routine trypsin-EDTA (0.53 mM EDTA), or 5 mM EDTA for detachment. We therefore incubated the attached cells in 3.5% lidocaine hydrochloride (Sigma) with 0.5 mM EDTA (diluted from 0.5M EDTA, PH 8.0, Invitrogen Corporation, Carlsbad, Calif.) for 5-8 minutes at room temperature to harvest cells for in vitro analysis and in vivo transplantation. Trypsin/EDTA may be used following lidocaine detachment in order to facilitate cell detachment and keep cell viability.

The attached cell population obtained by culturing the mononuclear cells of cord blood cultured in the 8-well Lab-Tek chamber slides (approximately 5% of mononuclear cells) could proliferate. These cells were therefore passaged every 5-7 days, up to a total of 7 passages over 2 months. Based on a growth curve generated over 12 days (FIG. 1A), we estimated the doubling time of CB-SC to be 2.8 days. Cell proliferation ability decreased in the longer-term cultures (over 3 months).

Flow Analysis and Cell Sorting

Flow analysis was preformed as previously described. Cells were detached by incubation in 3.5% lidocaine hydrochloride (Sigma) with 0.5 mM EDTA for 5-8 minutes at room temperature to harvest cells [Y. Zhao, H. Wang, T. Mazzone. *Exp Cell Res.* 312, 2454 (2006)]. For single staining, isotype-matched IgG1κ served as negative control for mouse monoclonal antibodies; normal rabbit IgG served as negative control for rabbit polyclonal antibody including CD117. For double stainings, cells were initially performed intracellular staining as previously described [Y. Zhao, H. Wang, T. Mazzone. *Exp Cell Res.* 312, 2454 (2006)]. Then, cells were staining with another primary antibody FITC-conjugated CD45. The isotypematched FITC-conjugated IgG (BD Pharmingen) served as negative control. After staining, cells were analyzed using a CyAn ADP (DakoCytomation) and Summit v4.2 software. For cell sorting, freshly isolated PBMC were stained with FITC-conjugated mouse antihuman CD14 monoclonal antibody (BD Pharmingen). The isotype-matched FITC-conjugated IgG served as negative control. After flow analysis and confirming high purity (>99.9%), CD14 cell population was collected and then seeded in the 8-Well Lab-Tek II Chamber Slide at 1×$10^5$ cells/ml, 0.5 ml/well in RPMI 1640 medium supplemented with 7% fetal bovine serum, and incubated at 37° C., 8% $CO_2$ conditions.

Example 2

Immunochemistry

Immunostaining was performed as previously described with minor modifications [Y. Zhao, T. Mazzone, Human umbilical cord blood-derived f-macrophages retain pluripotentiality after thrombopoietin expansion, Exp Cell Res. 310 (2005) 311-318]. The cells were incubated for 20 minutes at room temperature with ImmunoPure Peroxidase Suppressor (Pierce, Rockford, Ill.) to block endogenous perioxidase activity. For fluorescence-labeled immunostaining, this step was omitted. After incubation with primary antibodies, cells were stained with ABC kit (Vector Laboratories, Burlingame, Calif.). Immunostaining was performed using the following antibodies: mouse anti-human monoclonal antibodies CD3, CD9, CD11b/Mac-1 (Clone ICRF44), CD20, CD34 (clone 563), R-PE-conjugated mouse anti-human CD34 monoclonal antibody (clone 563), CD45 (HI30), FITC-conjugated mouse anti-human CD45 monoclonal antibody (HI30), CD146 (Clone P1H12), human leukocyte antigen (HLA)-DR, HLA-DQ, isotype-matched antibody $IgG_{1}\kappa$ were purchased from BD Pharmingen; mouse monoclonal antibodies SSEA-1, SSEA-3, SSEA-4, TRA-1-60, TRA-1-81, Oct-4, Thy-1 (CD90), synaptophysin, and tyrosine hydroxylase (TH) were from Chemicon International Inc. (Temecula, Calif.); mouse monoclonal antibodies CD11b and anti-human von Willebrand factor (vWF) were from Sigma (Saint Louis, Mo.); microtubule-associated protein (MAP) 1B antibody was from NeoMarkers. Rabbit anti-human polyclonal antibodies: Nanog antibody and glutamate decarboxylase$_{65/67}$ antibody were from Chemicon; γ-aminobutyric acid (GABA) antibody was from Sigma; antibodies CD117, Flt-1 (vascular endothelial growth factor receptor 1, VEGF R1), Flk-1 (VEGF R2) were from NeoMarkers. Rabbit anti-human HLA-ABC polyclonal antibody was from Santa Cruz Biotechnology (Santa Cruz, Calif.). Mouse monoclonal antibodies to human CD40, CD80 (B7-1), and CD86 (B7-2) were from eBioscience (San Diego, Calif.). Cells were then incubated with primary antibodies, the mouse $IgG_{1}\kappa$ (as control for mouse monoclonal antibodies), and normal rabbit IgG (as control for rabbit polyclonal antibodies, Santa Cruz). FITC- or rhodamine (TRITC)-conjugated AffiniPure Donkey anti-mouse IgG antibodies were obtained from Jackson ImmunoResearch Laboratories, INC. (West Grove Pa.). Alexa Fluor 568-conjugated second antibody was from Molecular Probes (Carlsbad, Calif.). After staining, the slides were mounted with Mounting Medium (Vector Laboratories, Burlingame, Calif.). Pancreatic slides were counterstained with hematoxylin for 8-10 min after immunostaining. Cells were viewed and photographed using a Zeiss Axiocam Color Camera with Zeiss Axioskop Histology/Digital Fluorescence microscope. The images were acquired with the manufacturer's software and edited using Adobe Photoshop Elements 2.0. When we evaluated cell percentage of expression of cells antigens, we used mouse or rabbit IgG staining as controls for background staining (<1%). Any cellular staining higher than the background staining, were regarded as positive staining and then quantified. At least 400 cells were evaluated from five randomly selected fields of each slide.

For double staining assay in the differentiation of endothelial-like cells, both VEGF-treated and untreated cells first completed incorporating acetylated low density lipoprotein labeled with 1,1-diocatadecyl-3,3,3,3-tetramethylindo-carbocyanine perchlorate (Dil-Ac-LDL, Biomedical Technologies Inc., Stroughton, Mass.), and then were fixed with 4% formaldehyde for 20 min at room temperature and used for immunostaining with specific cell surface marker CD146 as described above. PCR array was performed on the CB-SC using $RT^2$ Profiler PCR Array kit (SuperArray Bioscience Corporation). Additional gene markers for the CB-SC, such as activated leukocyte cell adhesion molecule (ALCAM), complement component 5a receptor 1 (C5AR1), CD37, CD63, CD74, colony stimulating factor 1 receptor (CSF1R), integrin alpha 3, myosin heavy chain 9 (non-muscle), were identified.

Example 3

Flow Analysis

For intracellular staining, cells were fixed with 4% paraformaldehyde for 20 min and then permeabilized with 0.5% Triton X-100 (Sigma) for 5-6 min at room temperature. For cell surface staining, the fixation and permeabilization steps were omitted. Cells were incubated with 2.5% horse serum (Vector Laboratories) at room temperature to block non-specific staining. Cells were incubated with primary antibodies for 45 min at 4° C. and then washed with cold PBS. Cells were stained with FITC-conjugated second antibodies for another 45 min at 4° C. and followed by flow analysis. Isotype-matched mouse $IgG_{1\kappa}$ antibody or normal rabbit IgG served as negative controls. After staining, cells were analyzed using a Beckman-Coulter Elite ESP.

Western Blot

Cells cultured in Petri dishes were washed with PBS and then solubilized with RIPA buffer (150 mM NaCl, 1.0% NP-40, 0.5% DOC, 0.1% SDS, 50 mM Tris (PH 8.0)) with a cocktail of protease inhibitors (Sigma). After forcing through a 21 G needle for 5 times, cell lysate was centrifuged at 12,000×g for 10 min at 4° C. Proteins samples (20 μg each) were mixed with a loading buffer (50 mM Tris, 10% SDS, 10% glycerol, 10% 2mercaptoethanol, 2 mg of bromphenol blue) in a volume ratio of 1:1, boiled, loaded, and separated by electrophoresis on 10% SDS gel. Human ES cell lysate served as positive control; mononuclear cells served as additional control for CB-SC. The separated proteins were then transferred to a nitrocellulose membrane, blocked with 5% non-fat dry milk in TBST for 1 h and incubated with different antibodies: including mouse anti human Oct-4 (1:500) and rabbit anti-human antibodies (1:1,000) to Nanog, PDX-1, NeuroD, NKX6.1, PC-1 and PC-2, diluted in PBST for 1 h at room temperature. After washing, the blot was exposed to a horseradish peroxidase-conjugated secondary antibody (1:2, 000; Pierce) in PBS-T. The immunocomplexes were visualized by the enhanced chemiluminescence (ECL, GE healthcare) method. Beta-actin served as an internal loading control.

In Situ Hybridization

To examine expression of Oct-4 mRNA, Nanog mRNA, and insulin mRNA, we performed in situ hybridization as previously described [Y. Zhao, T. Mazzone. *Exp Cell Res*. 310, 311 (2005)]. In brief, cells were fixed with 4% cold formaldehyde at 4° C. for 15 minutes. After blocking the endogenous peroxidase with ImmunoPure Peroxidase Suppressor (Pierce, Rockford, Ill.), the cells were used for in situ hybridization following the protocols provided by GeneDetect.com Ltd (Bradenton, Fla.). The biotin-labeled oligonucleotide probes to human Oct-4 (5'-AAAGCGGCA-GATGGTCGTTTGGCTGAAT-3' (SEQ ID NO: 7), NM002701) and Nanog (5'-TGGCAGGAGAATTTG-GCTGGAACTGCAT-3' (SEQ ID NO: 8), NM 024865) antisenses were obtained from Sigma-Genosys. The biotin-labeled oligonucleotide probes to human insulin antisense, sense control, and poly d(T) control were obtained from GeneDetect.com Ltd. Cells were incubated with the probes in hybridization buffer (DakoCytomation, Carpinteria, Calif.) at dilution 1:100 (1 μg/ml), 37° C. for 16-18 hours. The signals were detected using the Tyramide Signal Amplification System for In Situ Hybridizations by following their protocols as provided in the kit (DakoCytomation, Carpinteria, Calif.). The cells were viewed using a 40× oil immersion objective under the Zeiss Axioskop Histology/Digital Fluorescence microscope (Hallbergmoos, Germany), and then photographed with a Zeiss Axiocam Color Camera (Hallbergmoos, Germany). To confirm human PB-SC migrated into mouse pancreatic islets, we initially performed immunostaining using human C-peptide antibody (1:2,000, Linco Research, ST. Charles, Mo.), and then performed fluorescence in situ hybridization (FISH) using the human CEP® X/Y DNA Probe Kit (Vysis, Des Plaines, Ill.), following the manufacturer's protocols.

Example 4

Characterization of CB-SC

Immunostaining CB-SC on day 1 after isolation demonstrated the presence of hematopoietic cell antigens including tetraspanin CD9, leukocyte common antigen CD45, and stem cell factor receptor CD117 (data not shown). These cells did not express the macrophage marker CD11b/Mac-1, T lymphocyte marker CD3, B lymphocyte marker CD20, or the hematopoietic stem cell marker CD34 (data not shown). These results suggest that CB-SC are phenotypically distinct from macrophages, lymphocytes, and previously characterized CD34+ hematopoietic stem cells. To further characterize these cells, we evaluated expression of embryonic markers. Immunostaining results showed strong expression of ES cell-specific markers, including two critical transcription factors Oct-4 and Nanog (related to self-renewal and pluripotentiality of ES cells [S. H. Orkin, Chipping away at the Embryonic Stem Cell Network, Cell 122 (2005) 828-830]), along with stage-specific embryonic antigen (SSEA)-3 and SSEA-4 [I. Klimanskaya, Y. Chung, L. Meisner, J. Johnson, M. D. West, R. Lanza, Human embryonic stem cells derived without feeder cells, Lancet 365 (2005) 1636-1641]. Immunostaining showed that >90% of cells displayed embryonic transcription factors Oct-4 and Nanog, which are related to the self renewal of embryonic stem cells [Orkin S H: Chipping away at the Embryonic Stem Cell Network. *Cell* 122: 828-830, 2005]. Western blot and in situ hybridization further confirmed their protein and mRNA expressions. Human embryonic stem (ES) cell lysate served as positive control; and freshly isolated umbilical cord blood mononuclear cells served as additional control. CB-SC also showed weak expression of tumor rejection antigen (TRA)-1-60 and TRA-1-81, and no expression of SSEA-1 (FIG. 1B). Consistent with staining results at the early stage, all cells strongly expressed hematopoietic cell markers, including CD9, CD45, and CD117, but remained negative for CD3, CD11b/Mac-1, CD20, CD34, and CD90/Thy-1 surface antigens (FIG. 1C). Notably, flow analysis demonstrated that CB-SC maintained in 7% FBS-RPMI 1640 medium retained these phenotypes for over 2 months (FIGS. 2 A and B). The above results were obtained from 8 cord blood units yielding similar results, including fresh and liquid nitrogen-frozen preparations. Based on our current studies, CB-SC can be generated from every cord blood unit. Together, these data indicate CB-SC represent a unique cell population displaying both embryonic and hematopoietic cell characteristics.

Example 5

Immunogenicity-Associated Phenotypes of CB-SC

A major concern using stem cells for therapeutics is their immunogenicity, leading to immune rejection. Cellular immunogenicity is mainly determined by the major histocompatibility complex (MHC) including MHC class 1 molecule (HLA-ABC) and MHC Class II molecules (HLA-DR and HLA-DQ) [Drukker, G. Katz, A. Urbach, M. Schuldiner, G. Markel, J. Itskovitz-Eldor, B. Reubinoff, O. Mandelboim, N. Benvenisty, Characterization of the expression of MHC proteins in human embryonic stem cells, Proc Natl Acad Sci USA. 99 (2002) 9864-9869]. To more fully characterize CB-SC, we evaluated CB-SC for immunogenicity-associated phenotypes including HLA-ABC, HLA-DR, and HLA-DQ; along with immune response-related costimulating molecules CD40, CD80, and CD86. Immunostaining for two critical MHC molecules demonstrated that only 5% of cells expressed HLA-ABC, and HLA-DR was completely negative (FIG. 3A). These levels of expression are similar to levels of expression reported in human ES cells [Drukker, G. Katz, A. Urbach, M. Schuldiner, G. Markel, J. Itskovitz-Eldor, B. Reubinoff, O. Mandelboim, N. Benvenisty, Characterization of the expression of MHC proteins in human embryonic stem cells, Proc Natl Acad Sci USA. 99 (2002) 9864-9869]. Approximately 6% of cells showed weak expression for CD40 and CD80; ≈30% of cells expressed HLA-DQ; ≈22% of cells expressed CD86 (FIG. 3A).

Example 6

Effect of CB-SC on Stimulating the Proliferation of Allogeneic Lymphocytes

To more fully evaluate their immunogenicity, we performed a functional analysis using the mixed lymphocyte reaction. CB-SC as stimulator were seeded in 8-Well Lab-Tek II Chamber Slides at $1 \times 10^5$ cells/ml, 0.5 ml/well in RPMI 1640 medium supplemented with 7% fetal bovine serum and incubated at 37° C., 8% $CO_2$ conditions overnight. Allogenetic lymphocyte as responder were collected from buffy coats of healthy donors (Life-Source Blood Services, Glenview, Ill.) after removing all attached cells and then cocultured with CB-SC in triplicate at increasing CB-SC:Lymphocyte ratios (1:10, 1:20, and 1:40). Lymphocyte cultures without CB-SC served as controls. After 6 days, the suspended lymphocytes were collected and counted. As shown in FIG. 3B, CB-SC did not stimulate lymphocyte proliferation in an allogeneic mixed lymphocyte reaction, consistent with low immunogenicity demonstrated by immunostaining.

Example 7

Immune Regulation of CB-SC on T-Lymphocytes

In order to further understand the relationship between lymphocytes and CB-SC, we studied the immune regulation of CB-SC on T-lymphocytes.

CB-SC adhere very tightly to the culture dishes and display large rounded morphology, it is easy to distinguish between CB-SC and lymphocytes. CB-SC growing at 80% confluence were used for coculture with allogeneic lymphocytes. Allogeneic lymphocytes were collected from buffy coats of healthy donors (Life-Source Blood Services, Glenview, Ill.) after Ficoll-Hypaque separation followed by removing all attached cells and then cocultured with CB-SC at the ratio (1:10) [Zhao, Y., H. Wang, and T. Mazzone. 2006. Identification of stem cells from human umbilical cord blood with embryonic and hematopoietic characteristics. *Exp Cell Res.* 2006, 312: 2454-2464. DOI: 10.1016/j.yexcr.2006.04.008. April 26; (Epub ahead of print)] of CB-SC.

For PHA stimulation, lymphocyte suspensions ($1 \times 10^6$ cells/ml) with or without PHA (10 µg/ml, Sigma) were seeded onto CB-SC cell cultures in regular culture medium. PHA-stimulated lymphocytes without CB-SC served as positive control; lymphocytes cultured only in regular medium served as negative control. Lymphocytes cocultured with CB-SC without PHA stimulation served as an additional negative control. For IL-2 stimulation, IL-2 (500 U/ml, eBioscience) was used. After 5-6 days, the suspended lymphocytes were collected for cell count and/or flow analysis.

To evaluate the effect of cell-cell contact on inhibition of lymphocyte proliferation, CB-SC were fixed with 2.5% glutaraldehyde for 2 hours at room temperature followed by five washes with PBS and then used for coculture experiments as described above. Unfixed CB-SC from same cord blood units served as controls. Additionally, we employed transwell culture system with 0.4 µm size (Sigma) to plant lymphocytes.

In experiments where $N^{\omega}$-nitro-L-arginine (L-NNA, Sigma) was used to inhibit NO synthase, the drug (200 µM L-NNA) was added 1 h before PHA stimulation and then administrated 200 µM/day for additional two days. [Ziche, M., L. Morbidelli, E. Masini, S. Amerini, H. J. Granger, C. A. Maggi, P. Geppetti, and F. Ledda. 1994. Nitric oxide mediates angiogenesis in vivo and endothelial cell growth and migration in vitro promoted by substance P. *J Clin Invest.* 94:2036-2044].

Flow analysis was preformed as previously described [Zhao, Y., H. Wang, and T. Mazzone. 2006. Identification of stem cells from human umbilical cord blood with embryonic and hematopoietic characteristics. *Exp Cell Res.* 2006, 312: 2454-2464. DOI: 10.1016/j.yexcr.2006.04.008. April 26; (Epub ahead of print)]. In brief, for intracellular IL10 staining, cells were fixed with 4% paraformaldehyde for 20 min and then permeabilized with 0.5% Triton X-100 (Sigma) for 5-6 min at room temperature. Cells were incubated with 2.5% horse serum (Vector Laboratories) at room temperature to block non-specific staining. Cells were incubated with mouse anti-human IL-10 monoclonal antibody (R&D Systems, Minneapolis, Minn.) for 45 min at 4° C. and then washed with cold PBS. Cells were stained with FITC-conjugated second antibody for another 45 min at 4° C. and followed by flow analysis. For cell surface staining, the fixation and permeabilization steps were omitted. Cells were incubated with FITC-conjugated mouse anti-human CD4, PE-conjugated mouse anti-human CD8, and allophycocyanin (APC)-conjugated mouse anti-human CD25 (eBioscience, San Diego, Calif.) for 45 min at 4° C. and followed by flow analysis. Isotype-matched mouse IgG1κ antibody (BD Pharmingen) served as negative control. After staining, cells were analyzed using a CyAn ADP (DakoCytomation).

NO production was determined by using the Griess reagent [Ziche, M., L. Morbidelli, E. Masini, S. Amerini, H. J. Granger, C. A. Maggi, P. Geppetti, and F. Ledda. 1994. Nitric oxide mediates angiogenesis in vivo and endothelial cell growth and migration in vitro promoted by substance P. *J Clin Invest.* 94:2036-2044] (1% sulfanilamide, 0.1% naphthylenediamine dihydrochloride, 2.5% H3PO4, Sigma) in supernatants of PHA-stimulated and/or -unstimulated CB-SC. CB-SC were seeded at $1 \times 10^5$ cells/ml (0.5 ml/well) in 8-Well Lab-Tek II Chamber Slides. After attachment overnight, PHA was administrated to cell culture at different doses: 0, 2.5, 5, 10, 20 µg/ml in 0.5 ml culture medium/well. Supernatants were collected after treatment for 3-5 days for examination of NO production [Ziche, M., L. Morbidelli, E. Masini, S. Amerini, H. J. Granger, C. A. Maggi, P. Geppetti, and F. Ledda. 1994. Nitric oxide mediates angiogenesis in vivo and endothelial cell growth and migration in vitro promoted by substance P. *J Clin Invest.* 94:2036-2044]. Absorbance was measured at 540 nm. Diluted Sodium nitrite (NaNO2, Sigma) solution was served as standard curve to calculate the amount of NO. The PHA-treated and untreated cells were used for iNOS immunostaining as described below.

For iNOS examination, immunostaining was performed as previously described with minor modifications [Zhao, Y., H. Wang, and T. Mazzone. 2006. Identification of stem cells from human umbilical cord blood with embryonic and hematopoietic characteristics. *Exp Cell Res.* 2006, 312: 2454-2464. DOI: 10.1016/j.yexcr.2006.04.008. April 26; (Epub ahead of print)]. In brief, PHA-treated and untreated cells were fixed with 4% paraformaldehyde for 20 min and then permeabilized with 0.5% Triton X-100 (Sigma) for 5-6 min at room temperature. After blocking endogenous perioxidase activity and non-specific binding, cells were incubated with rabbit anti-inducible nitric oxide synthase (iNOS) polyclonal antibody (Biomol International, Plymouth Meeting, Pa.). Then, cells were stained with ABC kit (Vector Laboratories, Burlingame, Calif.). Normal rabbit IgG (Santa Cruz) served as negative control. Cells were viewed and photographed using a Zeiss Axiocam Color Camera with Zeiss Axioskop Histology/Digital Fluorescence microscope.

Regulation of CB-SC on $CD4^+$, $CD8^+$ T Lymphocytes and CD4/CD8 Ratio

To evaluate immune regulation of CB-SC on T cell subsets, CB-SC were initially cocultured with unsorted lymphocytes in the presence of different stimulators including IL-2 and PHA. Compared with lymphocytes alone, results showed that PHA stimulation could significantly increase the percentage of $CD8^+$ T cells and decrease $CD4^+$ T cell percentage by more than 2-fold respectively (p<0.05), with no changes on $CD4^-CD8^-$ T cells (Table 1); IL-2 stimulation could increase the percentage of $CD4^-CD8^-$ T cells, but failed to affect CD4/CD8 ratio. After coculture with CB-SC, the percentage of $CD4^-CD8^-$ T cells was significantly improved in both IL-2 and PHA stimulation (p<0.05 and P<0.01, respectively); the percentage of $CD8^+$ T-cell in PHA stimulation was reduced to control level by coculture with CB-SC, the decreasing of $CD4^+$ T cell percentage was significantly reversed, and therefore CD4/CD8 ratio was significantly upregulated (p<0.05) (Table 1).

Above results suggest that CB-SC may display negative regulation on IL-2- or PHA-activated T cells. To date, increasing evidence demonstrate that CD69 molecule function as an important negative regulator on activated lymphocytes [Sancho D, Gomez M, Sanchez-Madrid F. CD69 is an immunoregulatory molecule induced following activation. *Trends Immunol.* 2005, 26:136-140]. To further evaluate effects of CB-SC on T cell subset at single cell level, we examined CD69 expression on the sorted $CD4^+$ T cells and $CD8^+$ T cells after coculture with CB-SC. Compared with lymphocyte control, CD69 expression was upregulated considerably in PHA-stimulated $CD4^+$ and $CD8^+$ T cells, only slightly upregulation in IL-2 stimulation (FIGS. 4 A and B). After coculture with CB-SC, however flow analysis demonstrated that CD69 expression was further significantly increased on both $CD4^+$ T cells (FIG. 4A) and $CD8^+$ T cells (FIG. 4B) in both IL-2- and PHA-activated lymphocytes (p<0.05). It indicates that CB-SC display immune regulation on both $CD4^+$ and $CD8^+$ T cell subsets.

TABLE 1

Regulation of human peripheral blood lymphocyte subsets by CB-SC.

| Treatments | CD4⁻CD8⁻ T cells (%) | | CD4⁺ T cells (%) | | CD8⁺ T cells (%) | | CD4/CD8 ratio | |
|---|---|---|---|---|---|---|---|---|
| Lymphocytes | 8.11 ± 3.54 | | 65.65 ± 5.26 | | 22.85 ± 4.54 | | 2.87 ± 0.64 | |
| Lymphocytes + IL-2 | 19.09 ± 3.9 | ] * | 60.13 ± 7.02 | | 20.30 ± 2.85 | | 2.96 ± 0.71 | |
| Lymphocytes + IL-2 + CB-SC | 41.01 ± 5.3 | | 43.02 ± 11.04 | | 15.03 ± 5.80 | | 2.92 ± 0.28 | |
| Lymphocytes + PHA | 6.34 ± 1.42 | ] ** | 18.35 ± 5.03 | ] * | 75.12 ± 2.8 | ] ** | 0.24 ± 0.08 | ] * |
| Lymphocytes + PHA + CB-SC | 30.96 ± 9.67 | | 38.76 ± 7.94 | | 27.18 ± 2.30 | | 1.42 ± 0.48 | |
| Lymphocytes + CB-SC | 34.13 ± 15.25 | | 45.22 ± 3.64 | | 20.19 ± 10.9 | | 2.23 ± 0.94 | |

Note: After 5-day coculture at a 1:10 ratio of CB-SC: lymphocytes in the presence or absence of stimulators (500 U/ml IL-2 or 10 μg/ml PHA), the suspended lymphocytes were collected for flow analysis using CyAn ADP (DakoCytomation). Lymphocytes only cultured in regular culture medium served as negative control (top row). Lymphocytes cocultured with CB-SC in the absence of PHA served as additional negative control (bottom row). Cells were double stained with FITC-conjugated mouse anti-human CD4 and PE-conjugated mouse anti-human CD8 antibodies. Isotype-matched IgG$_{1\kappa}$ served as negative control. Data represent mean (±SD) from three experiments. Asteristic (*) represents for P value<0.05, ** for P value<0.01.

Regulation of CB-SC on CD4⁺ CD25⁺ Regulatory T Lymphocytes

Increasing evidence shows that regulatory T cells (Tregs) play a critical role in regulation of immune responses and homeostasis [Randolph, D. A. and C. G. Fathman. 2006. Cd4+Cd25+ regulatory T cells and their therapeutic potential. *Annu Rev Med.* 57: 381-402; Choileain, N. N. and H. P. Redmond. 2006. Regulatory T-cells and autoimmunity. *J Surg Res.* 130:124-135; Paust, S. and H. Cantor. 2005. Regulatory T cells and autoimmune disease. *Immunol Rev.* 204: 195-207]. To evaluate effects of CB-SC on CD4⁺ CD25⁺ Tregs, we performed cell sorting analysis using the sorted CD4⁺ CD25⁺ Tregs from human peripheral blood. Results showed that IL-2 (500 U/ml) could significantly stimulate the proliferation of CD4⁺ CD25⁺ Tregs, but was inhibited after coculture with CB-SC. To evaluate action of cell-cell contacting, CB-SC were cocultured with IL-2-stimulated CD4⁺ CD25⁺ Tregs presented in transwell system. Results showed that the proliferation of IL-2-stimulated CD4⁺ CD25⁺ Tregs was reversed after CD4⁺ CD25⁺ Tregs were separated from CB-SC (FIG. 5). It suggests that cell-cell contacting plays a more important role than soluble factors on the inhibition of proliferation of IL-2-stimulated CD4⁺ CD25⁺ Tregs.

Regulation of CB-SC on Interleukin-10 (IL-10) Production

Figure 6:
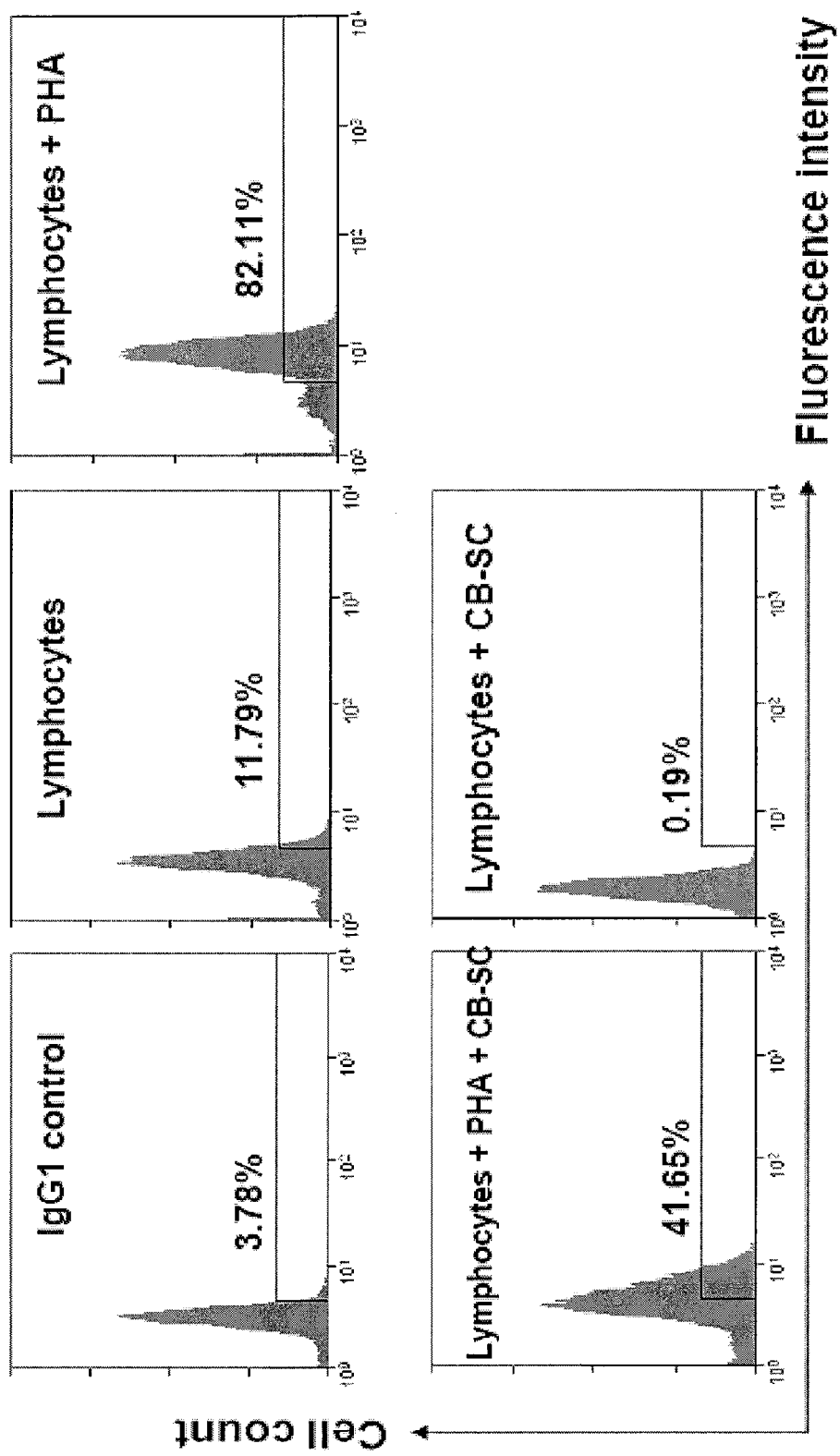
FIG. 6 shows the result of flow analysis of intracellular IL-10 production. Allogeneic lymphocytes were cocultured with CB-SC at ratio 1:10 of CB-SC: lymphocytes, in the presence or absence of mitogen PHA. After coculture for 5-6 days, cells were permeabalized and evaluated for intracytoplasmic IL-10 level by flow cytometry. Isotype-matched mouse IgG$_{1\kappa}$ antibody served as negative control. Data represent one of at least three experiments with the similar results.

IL-10 plays a critical role in mediating immune regulation on Th1 and Th2 immune responses. Monocytes and B lymphocytes are the major source for human IL-10 [Moore, K. W., A. O'Garra, R. de Waal Malefyt, P. Vieira, and T. R. Mosmann. 1993. Interleukin-10. *Annu Rev Immunol* 11: 165-190]. However, IL-10 is also produced other cell types including regulatory T cells [Hawrylowicz, C. M. and A. O'Garra. 2005. Potential role of interleukin-10-secreting regulatory T cells in allergy and asthma. *Nat Rev Immunol.* 5:271-83; Hawrylowicz, C. M. 2005. Regulatory T cells and IL-10 in allergic inflammation. *J Exp Med.* 202: 1459-1463; Battaglia, M., C. Gianfrani, S. Gregori, and M. G. Roncarolo. 2004. IL-10-producing T regulatory type 1 cells and oral tolerance. *Ann N Y Acad Sci.* 1029: 142-153], CD8⁺ T lymphocytes, mast cells, eosinophils, and keratinocytes [Moore, K. W., A. O'Garra, R. de Waal Malefyt, P. Vieira, and T. R. Mosmann. 1993. Interleukin-10. *Annu Rev Immunol* 11:165-190; Hawrylowicz, C. M. and A. O'Garra. 2005. Potential role of interleukin-10-secreting regulatory T cells in allergy and asthma. *Nat Rev Immunol.* 5:271-83; Hawrylowicz, C. M. 2005. Regulatory T cells and IL-10 in allergic inflammation. *J Exp Med.* 202: 1459-1463; Battaglia, M., C. Gianfrani, S. Gregori, and M. G. Roncarolo. 2004. IL-10-producing T regulatory type 1 cells and oral tolerance. *Ann N Y Acad Sci.* 1029: 142-153; Del Prete, G., M. De Carli, F. Almerigogna, M. G. Giudizi, R. Biagiotti, and S. Romagnani. 1993. Human IL-10 is produced by both type 1 helper (Th1) and type 2 helper (Th2) T cell clones and inhibits their antigen-specific proliferation and cytokine production. *J Immunol* 150: 353-360]. To evaluate IL10 production, we performed intracytoplasmic IL-10 analysis at single cell level using flow analysis. Results showed that 12% of untreated lymphocytes were positive for IL10; PHA stimulation could significantly enhance IL-10 production (FIG. 6). However, percentage of IL-10-positive cells in PHA-stimulated lymphocytes was decreased from 80% to 42% after coculture with CB-SC (FIG. 6).

Figure 7:
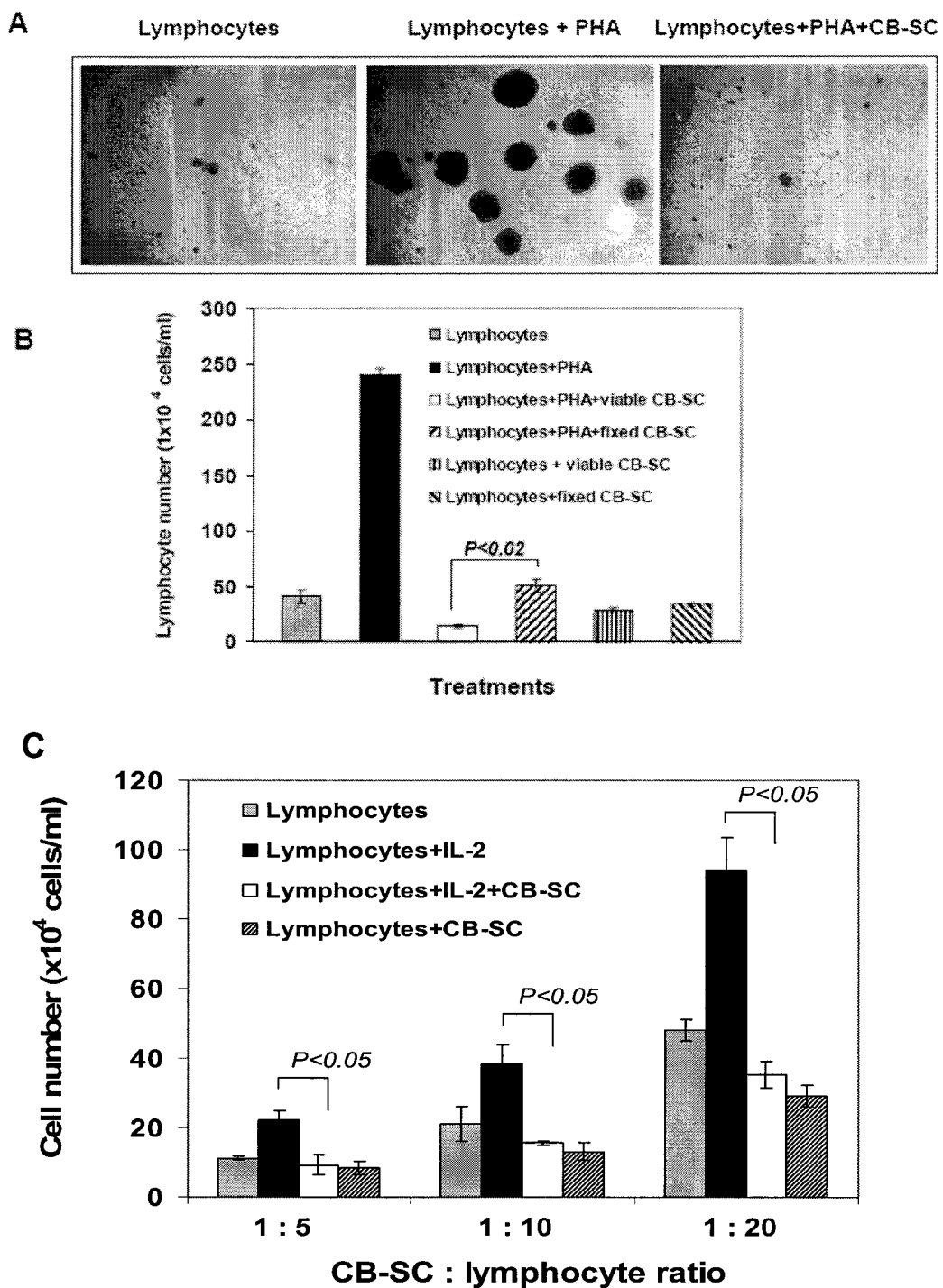
FIG. 7 shows the inhibitory effects of CB-SC on the PHA-stimulated lymphocyte proliferation. A, Cell clump formation by phase contrast microscope. PHA-stimulated lymphocytes formed larger cell clumps (middle panel); CB-SC (attached cells) cocultured with PHA-stimulated lymphocytes formed smaller cell clump (marked in red circle). Original magnification, ×50. B, Quantification of lymphocyte number. Allogeneic lymphocytes were cocultured with CB-SC for 5-6 days at ratio 1:10 of CB-SC:lymphocytes, in the presence or absence of mitogen PHA. C, CB-SC were cocultured with allogeneic lymphocytes at different ratios in the presence or absence of 500 U/ml IL-2. Data represent mean (±SD) of four experiments.

Inhibitory Effects of CB-SC on PHA-Stimulated Lymphocyte Proliferation and Role of Nitric Oxide Using phase-contrast microscopy, we observed that lymphocytes formed numbers of cell clumps of different size after stimulation with PHA in the absence of CB-SC (FIG. 7A, middle panel). However, the number of cell clumps was significantly reduced in the presence of CB-SC; most of lymphocytes were individually scattered in the culture medium and only a few cell clumps of very small size were observed (FIG. 7A, right panel). We further quantified cell number in different groups. Quantification of cell number showed a significant decrease in the PHA-stimulated lymphocyte proliferation by viable CB-SC (FIG. 7B, p<0.01). These results suggested that CB-SC could significantly inhibit the proliferation of PHA-stimulated allogeneic lymphocytes. To evaluate cell-to-cell contacting on this inhibition, we cocultured lymphocytes with 2.5% glutaraldehyde-fixed CB-SC. Results showed that lymphocyte proliferation was still significantly inhibited and but remained significantly higher in cocultured with the fixed CB-SC than that observed with viable CB-SC (FIG. 7B, p<0.02). These results suggest that both soluble factors and cell-to-cell contact participated in the inhibition of PHA-stimulated lymphocyte proliferation by CB-SC.

Next, we evaluated effects of CB-SC on physiological factor IL-2-stimulated lymphocyte proliferation. Using IL-2 (500 U/ml) as potent stimulator can significantly stimulate lymphocyte proliferation. However, their proliferation were significantly inhibited after coculture with CB-SC at different ratios (FIG. 7C, P<0.05). It suggests that CB-SC could inhibit the proliferation of both PHA- and IL-2-stimulated lymphocytes.

Figure 9:
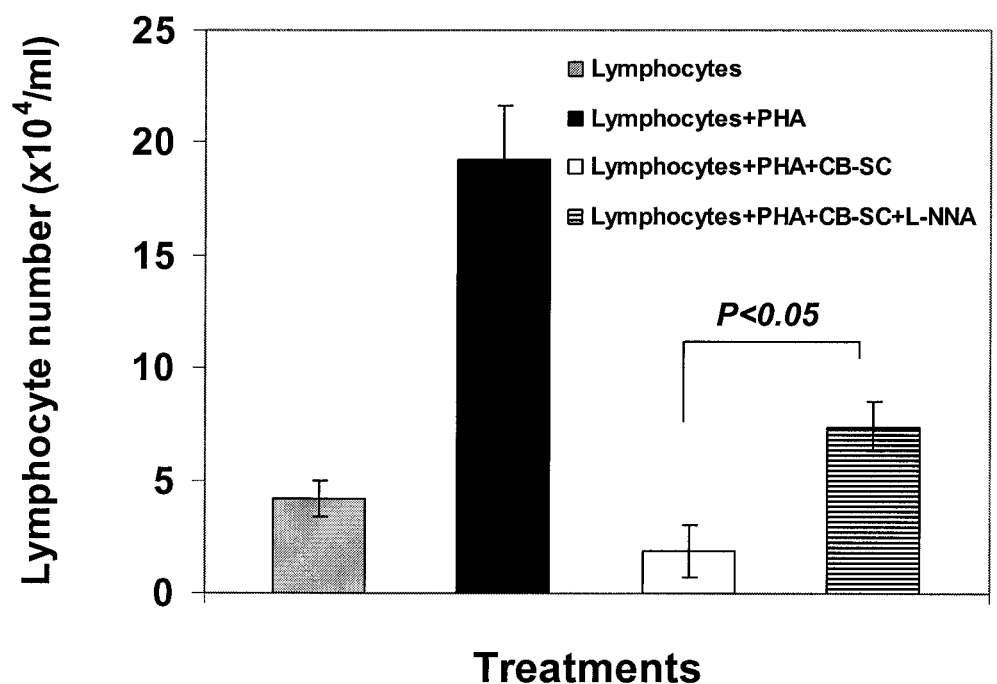
FIG. 9 shows the blocking effects of iNOS inhibitor L-NNA on the lymphocyte proliferation inhibited by coculture with CB-SC. PHA-stimulated lymphocytes were cocultured with CB-SC in the presence or absence of the iNOS inhibitor L-NNA (200 μM/day for 3 days). After coculture for 4 days, lymphocytes were harvested for cell count. Cell number represents mean (1 SD) of three experiments.

To find which soluble factor participated in above process, we evaluated whether CB-SC expressed inducible nitric oxide synthase (iNOS) and produced NO in the presence of PHA. Immunostaining results initially demonstrated that CB-SC increased the expression of iNOS after treatment with PHA (FIG. 8A, right panel). PHA-untreated CB-SC showed background level of iNOS (FIG. 8A, left panel). Using Griess reaction [Y. Zhao, T. Mazzone, Human umbilical cord blood-derived f-macrophages retain pluripotentiality after thrombopoietin expansion, Exp Cell Res. 310 (2005) 311-318; Y. Hori, X. Gu, X. Xie, S. K. Kim, Differentiation of insulin-producing cells from human neural progenitor cells, PLoS Med. 2 (2005) 347-356], we examined NO production. Results showed that PHA-treated CB-SC produced NO in a dose-dependent manner (FIG. 8B). To confirm NO mediated the inhibitory effects, we administered a powerful iNOS inhibitor L-NNA [Y. Zhao, T. Mazzone, Human umbilical cord blood-derived f-macrophages retain pluripotentiality after thrombopoietin expansion, Exp Cell Res. 310 (2005) 311-318 in the coculture of CB-SC with PHA-stimulated lymphocytes. The results demonstrated that cell number increased to a level about 4-fold higher in the presence of L-NNA than in the absence of L-NNA (FIG. 9, p<0.05). The data suggest that NO participated in inhibition of CB-SC on PHA-stimulated lymphocyte proliferation and could be partially blocked by administration of iNOS inhibitor (L-NNA).

Example 8

CB-SC Differentiation to Endothelial-Like Cells

We used CB-SC cultured for 1-2 months for experiments examining cell differentiation. For differentiation to endothelial-like cells, CB-SC were treated with 50 ng/ml vascular endothelial growth factor (VEGF, R&D System, Minneapolis, Minn.) in RPMI 1640 medium supplemented with 7% fetal bovine serum and incubated at 37° C., 8% $CO_2$. After 10-14 days, VEGF-treated and -untreated CB-SC were examined for endothelial-associated markers.

Immunostaining results showed that ≈97% of VEGF-treated CB-SC expressed endothelial cell markers including Flt-1 (VEGF receptor 1), Flk-1 (VEGF receptor 2), von Willebrand Factor (vWF), and 76% of cells were positive for transmembrane glycoprotein CD146 (FIG. 10A, bottom of left panel). Untreated CB-SC did not express these antigens (FIG. 10A, top of left panel). Hematopoietic antigens including CD45 and CD117 were down regulated in VEGF-treated cells (FIG. 10A, right panel). In vitro functional analysis showed that both the VEGF-treated and untreated CB-SC possessed strong ability to incorporate acetylated low density lipoprotein (Ac-LDL) (data not shown). Additionally, the cellular morphology of VEGF-treated CB-SC changed to broad endothelial-like cells with spontaneous formation of chain-like structures (FIG. 10B). We further characterized these structures with specific endothelial cell marker CD146 and endocytosis of Ac-LDL and showed that they were double positive (data not shown; Cells in chain-like structure were double stained with the acetylated low density lipoprotein (Ac-LDL) and CD146 and then merged. The merged image showed overlap of CD146 and Ac-LDL staining.)

Example 9

CB-SC Differentiation to Neuronal-Like Cells

Example 8 demonstrated that CB-SC produced endothelial-like cells, which arise from embryonic mesoderm [L. M. Hoffman, M. K. Carpenter, Characterization and culture of human embryonic stem cells, Nat Biotechnol. 23 (2005) 699-708; M. Baron, Induction of embryonic hematopoietic and endothelial stem/progenitor cells by hedgehog-mediated signals, Differentiation 68 (2001) 175-185]. We next evaluated the potential of CB-SC to differentiate to ectoderm-derived neuronal cells [L. M. Hoffman, M. K. Carpenter, Characterization and culture of human embryonic stem cells, Nat Biotechnol. 23 (2005) 699-708; L. Bally-Cuif, M. Hammerschmidt, Hammerschmidt. Induction and patterning of neuronal development, and its connection to cell cycle control, Curr Opin Neurobiol. 13 (2003) 16-25].

For differentiation to neuronal-like cells, CB-SC at 70% confluence were treated with 100 ng/ml nerve growth factor (NGF, R&D System) in RPMI 1640 medium supplemented with 7% fetal bovine serum in 8-well Lab-Tek chamber slides (Nunc, Naperville, Ill.) and incubated at 37° C., 8% $CO_2$. After 10-14 days, NGF-treated and -untreated CB-SC were examined with neuronal markers.

Figure 11:
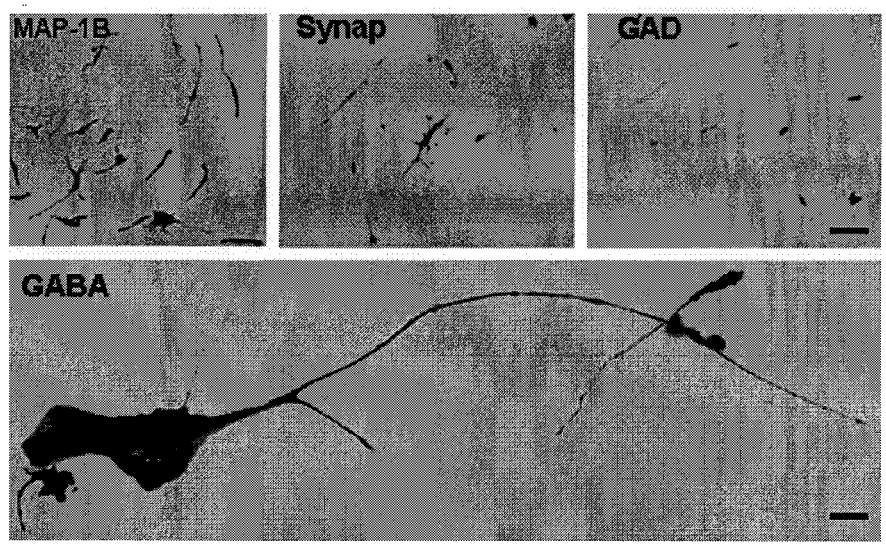
FIG. 11 shows the differentiation of CB-SC into neuronal-like cells. CB-SC were treated with 200 ng/ml NGF for 10-14 days and then prepared for immunostaining. Expression of neuronal cell-specific markers on NGF-treated cells. Scale bar is 37 μm. The images are representative of three experiments.

Following the treatment of CB-SC with NGF, CB-SC displayed elongated and/or branched morphologies and formed neuronal-like net works through elongated cell processes (FIG. 11). Immunostaining demonstrated they were positive for neuronal marker microtubule associated protein MAP-1B (FIG. 11); untreated cells (control) were negative or showed background staining (data not shown; NGF-untreated cells were stained with neuronal markers. Mouse IgG served as negative control for microtubule-associated protein-1b (MAP-1b) and synaptophysin (Synap); rabbit IgG served as negative control for γ-aminobutyric acid (GABA) and glutamate $decarboxylase_{65/67}$ (GAD)). To further evaluate neuronal phenotypes, we examined NGF-treated cells for neuronal function-associated markers [C. Andressen, S. Amhold, M. Puschmann, W. Bloch, J. Hescheler, R. Fassler, K. Addicks, Beta1 integrin deficiency impairs migration and differentiation of mouse embryonic stem cell derived neurons, Neurosci Lett. 251 (1998) 165-168]. As shown in FIG. 11, 85% of cells were positive for synaptophysin; 78% of cells expressed neuronal transmitter γ-aminobutyric acid (GABA) along with its critical synthesizing enzyme glutamic acid decarboxylase (GAD). Untreated CB-SC cells were negative for these markers (data not shown). Less than 5% of NGF-treated cells expressed dopaminergic neuron-associated tyrosine hydroxylase (TH) (data not shown). Hematopoietic antigens including CD9, CD45, and CD117 were down regulated following treatment with NGF (data not shown). Results suggest that NGF-treated CB-SC can give rise to GABAergic-like neurons.

Example 10

In Vivo Differentiation of CB-SC to Functional Insulin-Producing Cells

The above examples demonstrated that CB-SC can differentiate to mesoderm-derived endothelial-like cells, along with ectoderm-derived neuronal-like cells in vitro. To provide additional evidence of CB-SC's differentiation potential, we investigated whether CB-SC can differentiate into endoderm-derived insulin-producing cells [M. A. Hussain, N. D. Theise, Stem-cell therapy for diabetes mellitus, Lancet 364 (2004) 203-205; L. M. Hoffman, M. K. Carpenter, Characterization and culture of human embryonic stem cells, Nat Biotechnol. 23 (2005) 699-708] in vivo.

Because we transplanted human stem cells, the immune-deficient mice must be used to avoid immune rejection. To date, there is not an ideal type 1 diabetic model (caused by autoimmune destruction) available for xenograft transplantation. We therefore performed in vivo transplantation of CB-SC into streptozotocin (STZ)-induced diabetic Balb/c nude mice and evaluated their capacity to correct hyperglycemia.

Diabetes in Balb/c nude male mice was induced with a single intraperitoneal injection of streptozotocin (STZ) (Sigma) 220 mg/kg of body weight, freshly dissolved in citrate buffer (pH=4.5). Blood glucose levels were evaluated daily between 9 and 11 A.M. under nonfasting conditions. Diabetes was confirmed by the presence of weight loss, polyuria, and nonfasting blood glucose levels>350 mg/dl for 2 consecutive days. Diabetic mice were used for transplantation according to a protocol approved by the Animal Care Committee (ACC) of University of Illinois at Chicago. In brief, CB-SC at dosage of 5 million cells/mouse in 0.5 ml physiological saline was injected into the peritoneal cavity by injection with 27-gauge needle, normally on day 3 following the injection of streptozotocin. The control mice were injected only with an equal volume of physiological saline. Blood glucose levels were monitored using an AccuChek glucose detector (Roche Diagnostics, Indianapolis, Ind.).

Seven days after transplantation, we performed intraperitoneal glucose tolerance testing (IPGTT). Mice (CB-SC-transplanted diabetic mice, untransplanted diabetic mice, and non-diabetic mice) were fasted overnight (12 h). Mice were weighed and injected intraperitoneally with a bolus of glucose (2 mg/g of body weight). Blood was then drawn from a tail vein at 0, 5, 10, 20, 30, 45, 60, 90, and 120 min after glucose administration. Glucose levels were measured from whole tail vein blood as described above. To measure human C-peptide, blood samples were collected from the tail vein during a 20 min time period before and following IPGTT. Blood human C-peptide level was detected by using an ultra-sensitive human C-peptide enzyme-linked immunosorbent assay (ELISA) kit (Alpco Diagnostics, Windham, N.H.) following the manufacturer's protocols. This assay does not detect mouse C-peptide.

CB-SC-transplanted mice displayed significantly lower blood glucose levels (FIG. 12A). Further, intraperitoneal glucose tolerance testing (IPGTT) demonstrated physiological responses of transplanted CB-SC cells. Blood glucose of normal non-diabetic mice peaked between 5-10 min and returned to normal level 30 min following glucose challenge. Blood glucose of CB-SC-transplanted diabetic mice peaked at 20 min, followed by a return to normal range after 60 min (FIG. 12B). However, blood glucose of CB-SC-untransplanted diabetic mice remained very high (>500 mg/dl) (FIG. 12B).

To substantiate that this reversal of hyperglycemia was associated with differentiation of CB-SC into insulin-producing cells, we performed the following experiments. Due to the cross reactivity of antibodies between human and mouse insulin, we utilized an assay that is specific for human C-peptide (a by-product of insulin production) to evaluate human insulin secretion [Y. Hori, X. Gu, X. Xie, S. K. Kim, Differentiation of insulin-producing cells from human neural progenitor cells, PLoS Med. 2 (2005) 347-356; A. Hayek, G. M. Beattie, Experimental transplantation of human fetal and adult pancreatic islets, J Clin Endocrinol Metab. 82 (1997) 2471-2475; M. Zalzman, S. Gupta, R. K. Giri, I. Berkovich, B. S. Sappal, O. Karnieli, M. A. Zern, N. Fleischer, S. Efrat, Reversal of hyperglycemia in mice by using human expandable insulin-producing cells differentiated from fetal liver progenitor cells, Proc Natl Acad Sci USA. 100 (2003) 7253-8] from differentiated CB-SC cells. The results showed that human C-peptide was undetectable in mouse sera of CB-SC-untransplanted diabetic mice and normal non-diabetic mice, both prior to IPGTT and following IPGTT. In contrast, the human C-peptide level was significantly increased after IPGTT, to a level that was about 2 times higher than before IPGTT in the sera of the CB-SC-transplanted diabetic mice ($p<0.05$) (FIG. 12C). These experiments demonstrated that CB-SC differentiated into functional insulin-producing cells in diabetic mice.

CB-SC can proliferate and significantly increased in cell number. To evaluate the insulin-producing capability of the CB-SC, we examined the insulin gene transcription factors such as the basic leucine zipper MafA, Pdx-1 (pancreatic duodenal homeobox factor 1), NeuroD1 (neurogenic differentiation 1), HNF6 (hepatocyte nuclear factor 6, also known as Onecut1), Nkx6.1 (Nk homeobox gene), and Nkx2.2. We found that CB-SC significantly expressed these transcription factors and increased their levels in comparison with mononuclear cells; specifically for the β cell specific transcription factor MafA expression. MafA is a very specific insulin gene transcription factor for islet beta cells (Matsuoka T A, et al. Proc Natl Acad Sci USA. 2004; 101: 2930-2933); thus its expression indicates that the CB-SC are progenitors of insulin-producing cells.

Example 11

In Vitro Evidence for Differentiation of CB-SC to Insulin-Producing Cells

Cord Blood-Derived Stem Cells (CB-SC) Display Nestin.

Figure 13:
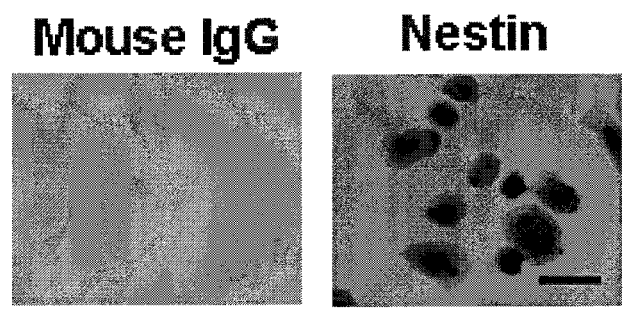
FIG. 13 shows the expression of nestin on CB-SC. Immunostaining of CB-SC with human nestin monoclonal antibody. Isotype-matched IgG1κ served as negative control.

To date, nestin as an intermediate filament protein has been regarded as the marker of a neuroendocrine progenitor cells and nestin-positive cells can give rise to insulin-producing cells. Immunostaining showed that CB-SC strongly expressed nestin (FIG. 13).

CB-SC Display the Potential to Give Rise to Insulin-Producing Cells.

Figure 14:
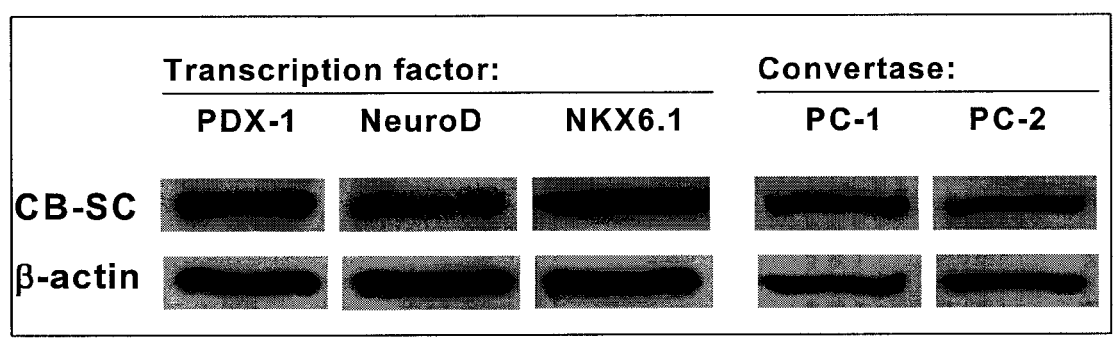
FIG. 14 is the result of Western blot for transcription factors including PDX-1, NeuroD, and NKX6.1, along with prohormone convertases PC-1 and PC-2. β-actin served as internal control.

To evaluate potential of CB-SC differentiating to insulin-producing cells, we also examined pancreatic islet β-cell development-associated transcription factors, including PDX-1, NeuroD and NKX6.1. Western blot demonstrated that CB-SC strongly expressed NeuroD, PDX-1 (a well-known transcription factor essential for beta cell development), and NKX6.1 (that commits pancreatic progenitors to β cells) (FIG. 14). CB-SC also expressed prohormone convertase PC1 and PC2 (FIG. 14), which are usually presented in islet β cells and other cellular tissues associated with peptide synthesis.

Expression of Glucagon-Like Peptide 1 (GLP-1) Receptor on CB-SC

Figure 15:
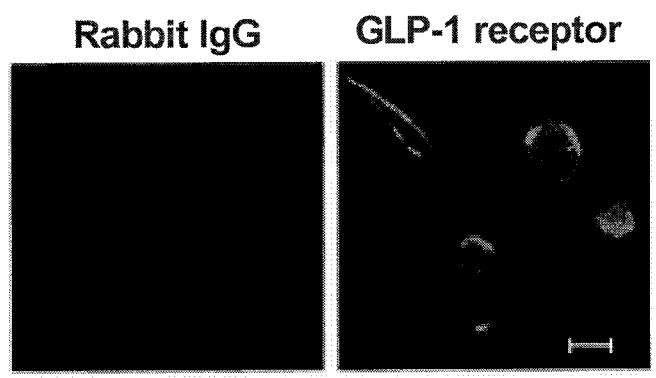
FIG. 15 shows the result of immunostaining for GLP-1receptor on CB-SC. Cells were cultured in 8-well Lab-Teck II chamber slides in regular culture medium and used for immunostaining with rabbit anti-human GLP-1 receptor polyclonal antibody. Normal rabbit IgG served as control for immunostaining. Scale bar, 20 μm. Cells were photographed using Zeiss LSM 510 confocal microscope.

Exendin-4, a long-acting agonist of GLP-1, can stimulate both beta cell differentiation and proliferation. Immunostainings have demonstrated around 76% of CB-SC expressed glucagon-like peptide 1 (GLP-1) receptor (FIG. 15). To optimize differentiation of CB-SC into insulin-producing cells and improve their therapeutic potential, therefore we have administrated exendin-4, in combination with high glucose and/or lipopolysaccharide (LPS).

In Vitro Differentiation of CB-SC to Insulin-Producing Cells.

In the presence of 10 ng/ml exendin-4+50 ng/ml lipopolysaccharide (LPS)+25 mM glucose, CB-SC could improve insulin production from 95.7±29 to 288.5±22 pg/mg cell protein, and C-peptide production from 4.3±1.4 to 11.11±2.7 fmol/mg cell protein.

Example 12

Differentiation of CB-SC to Oligodendrocytes

Figure 16:
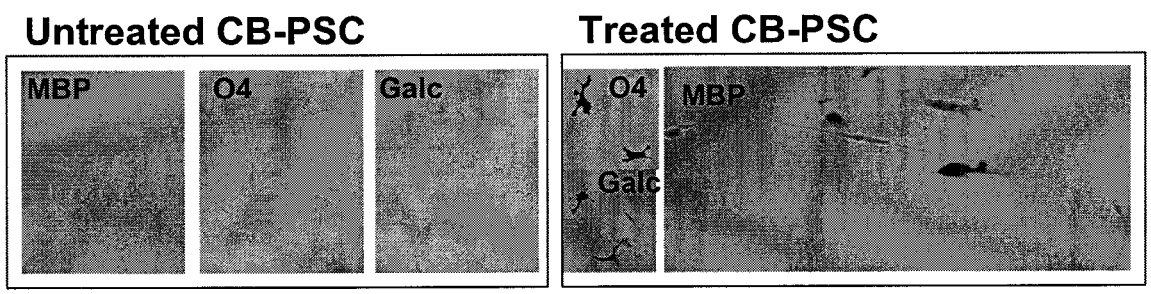
FIG. 16 shows the differentiation of CB-SC into the oligodendrocyte. CB-SC were treated with 200 ng/ml NGF for 10-14 days. Expression of oligodendrocyte-specific markers on NGF-treated CB-PSC, including myelin basic protein (MBP) (67-74), sulfatide O4, and galactocerebroside (Galc). Original magnification: ×400.

In the presence of nerve growth factor (NGF, 200 ng/ml), we also found some of cells acquired oligodendrocytes-like morphology, with shorter branched cellular processes. Immunostaining results demonstrated that 25-29% of cells expressed specific oligodendrocyte markers myelin basic protein (MBP) (67-74), sulfatide O4, and galactocerebroside (Galc, a major glycolipid in mylin) (FIG. 16, right panel). However, no expression was observed in the NGF-untreated cells (FIG. 16, left panel).

Example 13

Differentiation of CB-SC to Megakaryocyte-Like Cells

We treated CB-SC with thrombopoietin (TPO, 10 ng/ml). Cells were analyzed for megakaryocyte surface markers and their ploidy status. The results showed that around 70% of TPO-treated cells expressed megakaryocyte specific marker CD41b (data not shown; the differentiation of CB-SC into the megakaryocyte was observed through immunostaining. CB-SC were treated with 10 ng/ml TPO for 10-14 days. Immunostaining showed expression of megakaryocyte-specific marker CD41b on differentiated CB-SC. DAPI staining showed polyploidy nuclear and an undifferentiated cell with regular size of nuclear. Original magnification: ×400)). Dapi staining showed that these positive cells appeared with polyploidy nuclear. However, untreated cells failed to express these antigens with regular size of nuclear.

Example 14

Expression of Chemokine Receptor CXCR4 on CB-SC

Figure 17:
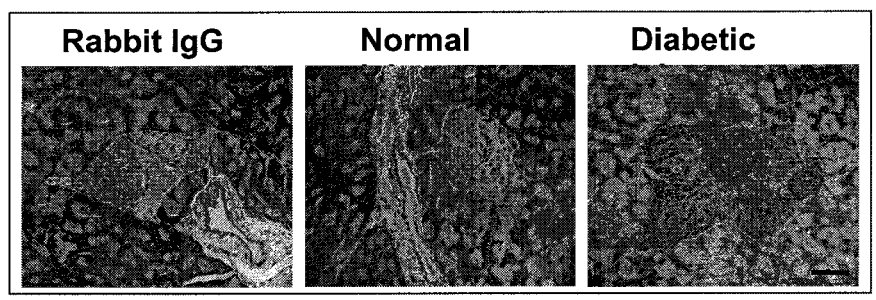
FIG. 17 shows the expression of SDF-1 in Rabbit IgG, normal islets, and diabetic islets (Scale bar, 36 μm)
Figure 18:
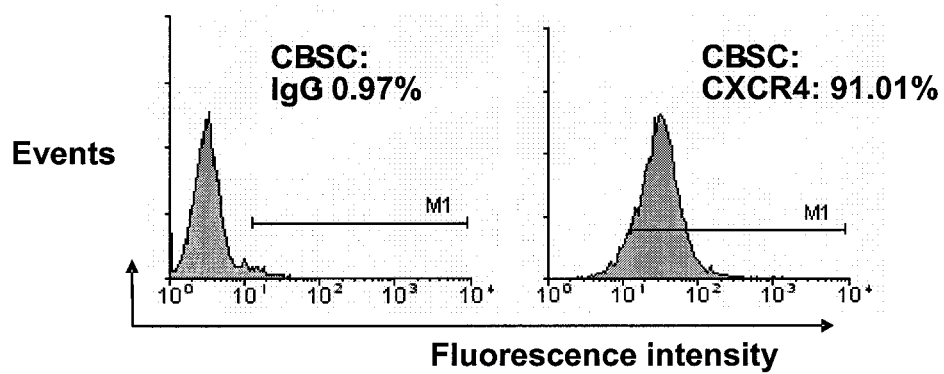
FIG. 18 is the result of flow analyses showing the expression of the SDF-1 diabetic islet receptor CXCR4 on CB-SC. Data represent one of three experiments with the similar results.

Recently, increasing evidence demonstrate that the chemokine stromal cell-derived factor-1 (SDF-1) and its receptor, CXCR4, play an essential role in mediating hematopoietic stem cell homing. To evaluate the mechanism of CB-SC homing, we performed immunostaining analysis on the STZ-induced diabetic pancreatic islets. Results showed that diabetic pancreatic islets displayed SDF-1, but lack expression in pancreatic islets of normal NOD-scid mice (FIG. 17). Notably, CB-SC expressed SDF-1 receptor CXCR4 (FIG. 18). The data suggest that SDF-1/CXCR4 may contribute to guiding of CB-SC into pancreatic islets.

Example 15

Using CB-SC-Treated Lymphocytes as a Vaccine to Prevent Autoimmune Disease (e.g. Type 1 Diabetes)

NOD/LtJ mice were used as a model for studying type 1 diabetes. NOD/LtJ mice is an art-reconized model of type 1 diabetes. In the NOD/LtJ mice, their autoimmune lymphocytes can selectively destroy the islet beta cells and cause diabetes. Therefore, NOC/LtJ mice can spontaneously develop diabetes and serve as a good model for autoimmune-caused type 1 diabetes, especially the female NOD/LtJ mice develop autoimmune-caused type 1 diabetes at a higher incidence.

Figure 19:
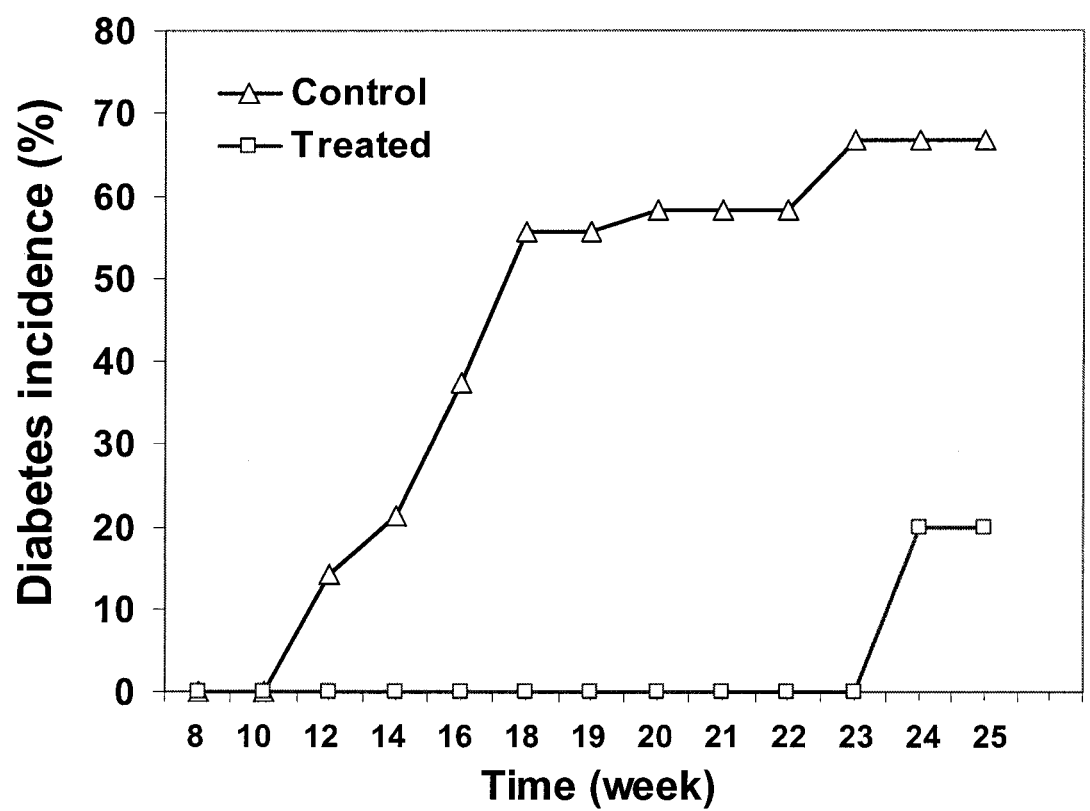
FIG. 19 shows that CB-SC-treated lymphocytes significantly delayed and protected NOD mice for generation of diabetes.
Figure 20:
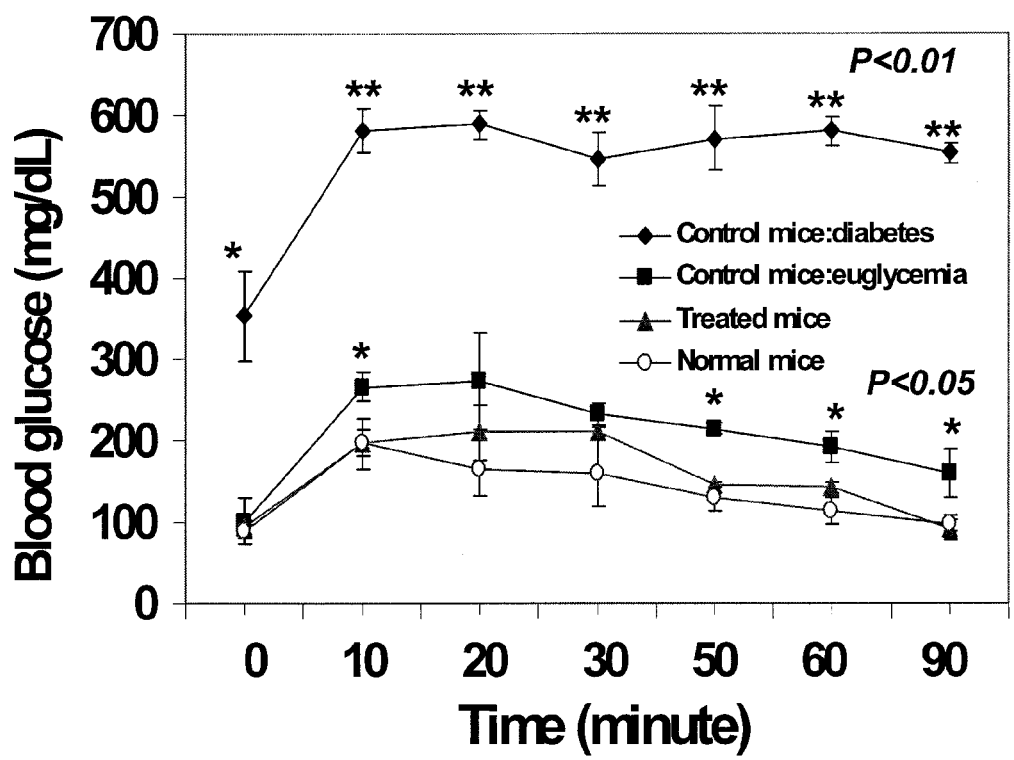
FIG. 20 shows the result of glucose tolerance testing (IP-GTT) demonstrating that there were no big difference between the group of CB-SC-treated lymphocytes and the group of normal mice.

Mouse lymphocytes were isolated from 6-week female NOD/LtJ mouse spleens and then cocultured with CB-SC at a ratio of 1:10 of CB-SC:lymphocytes. After coculturing with CB-SC for 4-5 days, the floated lymphocytes were collected for in vivo vaccination and administrated into the 6-week-old NOD mice (1-2 million lymphocytes/mouse, i.p., n=5). Physiological saline and non-cocultured mouse lymphocytes served as controls. Mice were examined for protection against diabetes, including monitoring blood glucose, measuring body weight, performing glucose tolerance tests, blood insulin tests, and histological examinations. The results demonstrated that CB-SC-treated mouse lymphocytes could significantly delay and protect NOD mice for generation of diabetes, with only 20% of diabetes incidence on week 30; however, control mice reached about 75% of diabetes incidence (FIG. 19). Glucose tolerance testing (IPGTT) demonstrated that there were no significant difference between the group of CB-SC-treated lymphocytes and the group of normal mice (FIG. 20); importantly 30% of control mice even with euglycemia still showed the impaired glucose tolerance test (FIG. 20).

Figure 21:
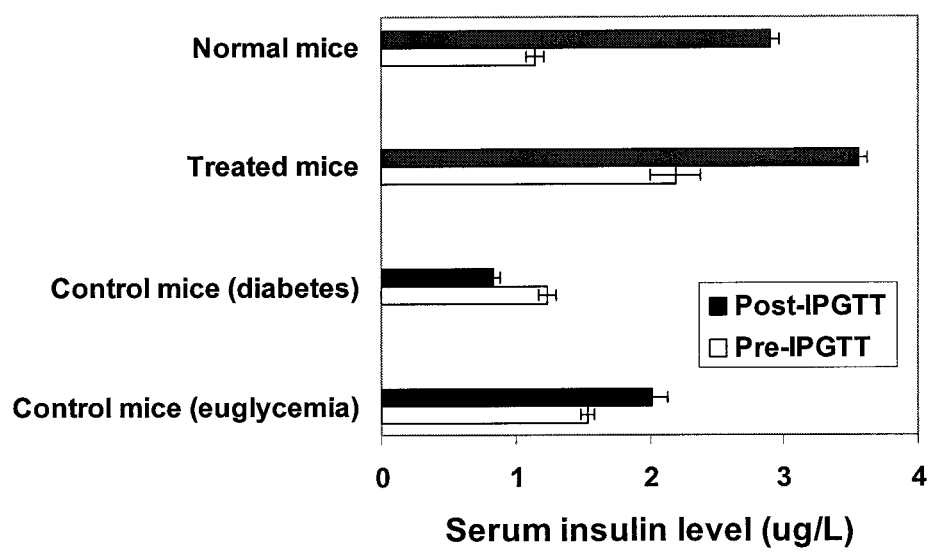
FIG. 21 is a bar graph showing that mouse blood insulin levels pre- and post intraperitoneal glucose tolerance testing (IPGTT) for normal mice, mice treated with CB-SC-treated lymphocytes, control mice (with established diabetes), and control mice (with euglycemia)
Figure 22:
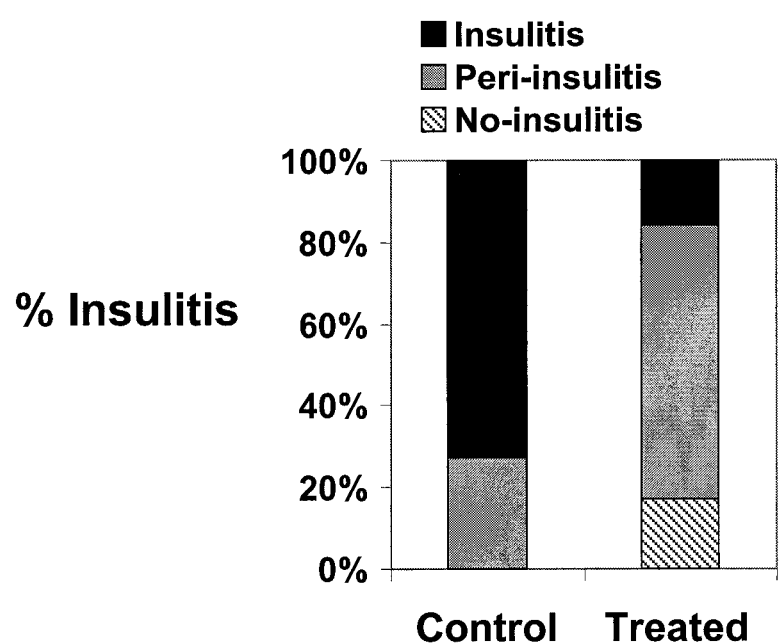
FIG. 22 is a bar graph showing the percentage insulitis in control mice versus mice treated with CB-SC-treated lymphocytes.

Using an ELISA kit, mouse blood insulin levels were evaluated both pre- and post IPGTT. Results showed that the group of CB-SC-treated lymphocytes displayed normal insulin level and response in response to high glucose challenge (FIG. 21); however, control mice displayed significantly low level of blood insulin levels and impaired responses (FIG. 21). Histology examinations (not shown) demonstrated that control mice displayed significantly more insulitis in comparison with the group of CB-SC-treated lymphocytes (FIG. 22). Taken together, these data confirmed that administration of CB-SC-treated lymphocytes can significantly protect diabetes onset in type 1 diabetes. Human peripheral blood-derived stem cells (PB-SC) can also be used to prevent diabetes onset by using the co-cultured lymphocytes.

Flow analysis was used to determine the phenotypic changes of potential regulatory T cells after co-culturing with CB-SC. Pacific blue CD-62L, FITC-CD25, FITC-CD4, FITC-CD19, and PE-CD8 antibodies were used. Flow analysis demonstrated that the percentage of $CD4^+CD25^+$ Treg cells (approx. 1%) failed to show significant changes after coculture with CB-SC, while the percentage of $CD4^+CD62L^+$ T cells (approx. 12% (untreated) vs approx. 20% (treated)) and $CD8^+CD62L^+$ T cells (approx. 4% (untreated) vs approx. 17% (treated)) increased (data not shown). Additionally, the percentage of $CD19^+CD62L^+$ B cells (approx. 20% (untreated) vs approx. 28% (treated)) also increased after coculture with CB-SC.

Protocols for Treatment with Sorted $CD62L^+$ T Cells:

CB-SC growing at 80% confluence were used for coculture with NOD mouse lymphocytes (5-8 week ages). Mouse lymphocytes were collected from spleens after Ficoll-Hypaque separation and then cocultured with CB-SC at the 1:10 ratio of CB-SC: lymphocyte. After 3-5 days, the suspended lymphocytes are collected for cell count and/or flow analysis. A few lymphocytes adhering to CB-SC can be easily detached by trypsin-EDTA and also be counted. (note: BD-PSC (blood derived pluripotent stem cells, which include both CB-SC and PB-SC) are resistant to the detachment by using trypsin-EDTA).

After coculture with CB-SC, mouse lymphocytes will be stained with rat anti-mouse monoclonal antibodies (eBioscience): Alexfluora 647-conjugated CD3, FITC-conjugated CD4, PE-conjugated CD8, and allophycocyanin (APC)-conjugated CD25, FITC-conjugated DX5 (CD49b), and PE-Cy7 or pacific blue-conjugated CD62L for 45 min at 4° C. and followed by three-way cell sorting, using MoFlo (DakoCytomation). The isotype-matched FITC-conjugated IgG served as negative control. To block FcR binding and non-specific binding, rat anti-mouse CD16 (FcR) antibody and 0.5% BSA will be used for every staining. After flow analysis and confirming high purity (>98%), $CD4^+CD62L^+$ T cells and $CD8^+CD62L^+$ T cells were collected and then prepared for different experiments.

In Vivo Treatment with the Sorted T Cell Subpopulations

For diabetes prevention, the sorted T cell subpopulations following coculture with CB-SC, were administered into the 6-week female NOD mice (1 million cells/mouse, i.p., n=5). PBS served as control. NOD mice were monitored for diabetes development. Administration of human cord blood stem cell (CB-SC)-modulated T lymphocytes including both CD4$^+$CD62L$^+$ and CD8$^+$CD62L$^+$ T cells can significantly delay and prevent diabetes onset in the autoimmune-caused type 1 diabetes NOD mouse model. Interestingly, administration of CD8$^+$CD62L$^+$ T cells could considerably delay the diabetes onset (FIG. 23A); while CD4$^+$CD62L$^+$ T cells had less of an effect. These experiments were further confirmed by glucose tolerance testing (FIG. 24A-D). Therefore, CD8$^+$CD62L$^+$ T cells play an important role in the prevention of diabetes onset. Treatment with CD19$^+$CD62L$^+$ B cells could also delay and prevent diabetes onset in NOD mice, however had less effect than CD3$^+$CD62L$^+$ T cells (FIG. 23B).

For reverse diabetes, the sorted T cell subpopulations following coculture with CB-SC, were administered into the diabetic NOD mice (3 million cells/mouse, i.p., once a week for two consecutive weeks). Diabetes were confirmed by the presence of weight loss, polyuria, and blood glucose levels>250 mg/dl for two consecutive days and used for experiments.

Notably, treatment with CB-SC-modulated CD4$^+$CD62L$^+$ T cells (3 million cells/mouse, i.p., one dose per week for two consecutive weeks), can reverse diabetes and achieve euglycemia in the established diabetic NOD mice (3/3 of mice) (FIG. 25A). CD8$^+$CD62L$^+$ T cells did not reverse diabetes in the NOD mice. (FIG. 25B).

Regulatory T lymphocytes such as CD8$^+$CD62L$^+$ T cells modulate the initiation stage of autoimmune responses of type 1 diabetic NOD mice; while CD4$^+$CD62L$^+$ T cells play a key role in regulation of the effective stage of autoimmune responses of type 1 diabetic NOD mice. These regulatory T cells can produce TGF-beta 1 and/or other cytokines (e.g., IL-4, IL-10, IL-25) to modulate autoimmune responses. Another potential mechanism can be associated with cell-cell contacting via adhesive surface molecules (e.g., ICAMI) and costimulating molecules (e.g., CD28 and CD40L).

Example 16

Using CB-SC to Treat Autoimmune Diabetes

To test the therapeutic potential of CB-SC to treat type 1 diabetes, we established an autoimmune diabetes model using adoptively transferring of diabetes from the autoimmune-caused diabetic NOD/LtJ mouse to NOD-scid mouse (see Yamada S, et al. 2003 Ann N Y Acad Sci. 1005:211). In brief, lymphocytes were isolated from spleens of diabetic female NOD/LtJ mice (Jackson Laboratories, Bar Harbor, Me.) which were more than 16 weeks old. Spleens were teased apart into single cell suspensions. Lymphocytes were isolated by density-gradient centrifugation ($\gamma$=1.077 g/ml, Sigma, St. Louis, Mo.) as previously described. The cells were washed three times with 2% FCS-RPMI-1640 and kept on ice until time of transfer. Lymphocytes ($2\times10^7$) were injected (i.p., 200 (µl/ml) into 8 week-old NOD-scid mice. One to two weeks later, CB-SC at a dose 5-10 million cells/mouse were administered (i.p., n=5). Physiological saline served as control. Mice were followed for the development of hyperglycemia. Blood glucose was monitored weekly. Results demonstrated 100% (3/3) of control mice had developed diabetes; notably, mice treated with CB-SC only showed 20% (⅕) of diabetes incidence. These data demonstrated the therapeutic potential of CB-SC to treat autoimmune diabetes.

Example 17

Blood Stem Cell-Derived Insulin-Producing Cells Suppress the Proliferation of Autoimmune Lymphocytes As demonstrated above, CB-SC can differentiate into insulin-producing cells. Controlling autoimmune lymphocytes can be used to treat or ameliorate or reduce the risk of developing type 1 diabetes, because autoimmune lymphocytes can destroy not only the islet beta cells but also the stem cell-derived insulin-producing cells. This example establishes the efficacy of blood stem cell-derived insulin-producing cells to control those autoimmune lymphocytes without the addition of other demanding strategies.

The programmed death receptor-1 ligand 1 (PD-L1) expressed on CB-SC membrane, together with a soluble factor nitric oxide (NO) released by PHA-stimulated CB-SC, not prostaglandin E2 (PGE2) and transforming growth factor-β1 (TGF-β1), mainly contributed to the T cell suppression induced by CB-SC, as demonstrated by blocking experiments with a nitric oxide synthase inhibitor (N-omega-nitro-L-arginine, L-NNA) and a neutralizing antibody to PD-L1. To evaluate the therapeutic potential of blood stem cell-derived insulin-producing cells, we examined expressions of inducible nitric oxide synthase (iNOS) and PD-L1 in the embryonic-like stem cells after treatment with 10 nM Exendin4+10 ng/ml GM-CSF+25 mM glucose in 7% FBS-DMEM culture medium for 3-5 days. Results demonstrated that they expressed iNOS at high level (data not shown); low percentages of cells (5-10%) were also positive for PD-L1. Thus, the insulin-producing cells can regulate the diabetic lymphocytes through the soluble factors, such as NO, and also through cell-cell contact, such as through increased expression of programmed death receptor-1 ligand expressed on the embryonic-like stem cells that can suppress lymphocytes through the interaction with PDL receptor on lymphocytes. Furthermore, as discussed above, the epigenetic regulation on DNA methyltransferase (DNMT) activity of lymphocytes by CB-SC-derived NO can be significantly blocked by presence of a specific inducible nitric oxide synthase (iNOS) inhibitor 1400 W (FIG. 5B).

Notably, we found that human blood stem cells and/or blood stem cell-derived insulin-producing cells expressed carboxypeptidase M (CPM) and carboxypeptidase E (CPE), as demonstrated by real time PCR. The expression of CPM was further confirmed by immunostaining using the monoclonal antibody. Both carboxypeptidase M and carboxypeptidase E can hydrolyze the carboxy-terminal (C-terminal) peptide bond of proteins and peptides by releasing the last amino acid (argine) of the chain. For example in islet beta cells, after cleavage of proinsulin by protein convertases PC1/3 or PC2, the remaining COOH-terminal basic residues are removed from the B-chain (Arg$^{31}$-Arg$^{32}$) and C-peptide (Lys$^{64}$-Arg$^{65}$) by carboxypeptidase E (CPE) resulting in the formation of mature insulin and C-peptide (Docherty K, Hutton J C 1983 *Carboxypeptidase activity in the insulin secretory granule. FEBS Lett* 162:137-141). The released argine can serve as the substrate for iNOS and contribute to NO production (Hadkar V, et al. *Am J Physiol Lung Cell Mol Physiol.* 2004 July; 287 (1):L35-45).

Figure 26:
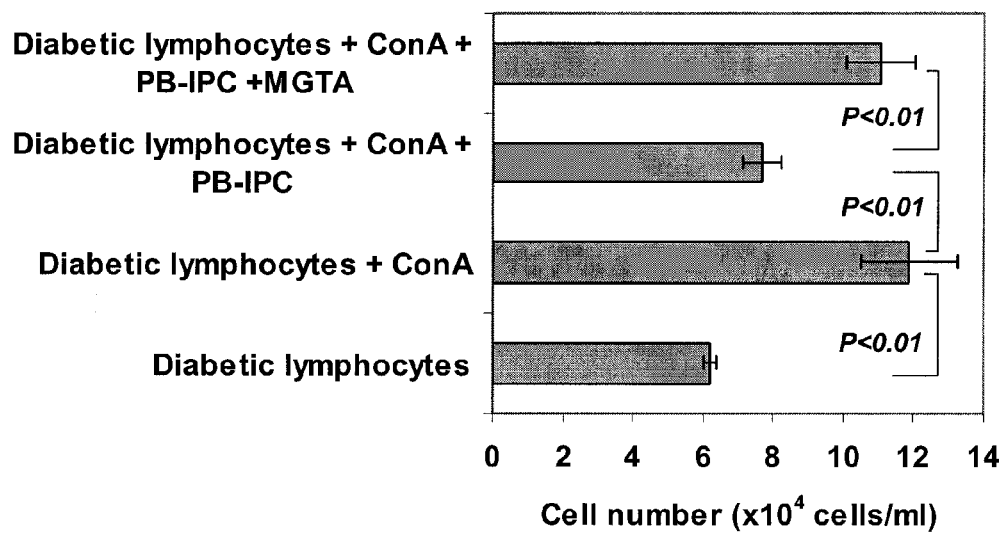
FIG. 26 is a bar graph showing lymphocyte proliferation demonstrating that embryonic-like stem cells can inhibit the proliferation of ConA-stimulated lymphocytes, and reverted in the presence of the specific carboxypeptidase inhibitor, carboxypeptidase inhibitor 2-mercaptomethyl-3-guanidino-ethylthiopropanoic acid (MGTA, 10 μM).

We demonstrate that carboxypeptidase-derived NO can contribute to the lymphocyte suppression of blood stem cell-derived insulin-producing cells. The specific carboxypeptidase inhibitor, carboxypeptidase inhibitor 2-mercaptomethyl-3-guanidinoethylthiopropanoic acid (MGTA, 10 μM) was applied to block carboxypeptidase. First, embryonic-like stem cells were differentiated by treatment with 10 nM Exendin4+10 ng/ml GM-CSF+25 mM glucose in 7% FBS-DMEM culture medium for 3-5 days. Second, autoimmune lymphocytes were isolated form the diabetic NOD mouse and then cocultured with these embryonic-like stem cells in the presence MGTA. The mouse lymphocyte mitogen concanavalin A (ConA) was used to stimulate the proliferation of lymphocytes. Results demonstrated that the embryonic-like stem cells could inhibit the proliferation of ConA-stimulated lymphocytes (p<0.01); and administration of carboxypeptidase inhibitor MGTA could completely revert their inhibition (p<0.01) (FIG. 26).

While the present invention has been described in terms of specific methods and compositions, it is understood that variations and modifications will occur to those skilled in the art upon consideration of the present invention. Those skilled in the art will appreciate, or be able to ascertain using no more than routine experimentation, further features and advantages of the invention based on the above-described embodiments. The practice of the present invention will employ and incorporate, unless otherwise indicated, conventional techniques of cell biology, cell culture, molecular biology, microbiology, genetic engineering, and immunology, which are within the skill of the art. While the present invention is described in connection with what is presently considered to be the most practical and preferred embodiments, it should be appreciated that the invention is not limited to the disclosed embodiments, and is intended to cover various modifications and equivalent arrangements included within the spirit and scope of the claims. Modifications and variations in the present invention may be made without departing from the novel aspects of the invention as defined in the claims. Accordingly, the invention is not to be limited by what has been particularly shown and described. All publications and references are herein expressly incorporated by reference in their entirety.

The invention claimed is:

1. A method for isolating stem cells, comprising:
   (a) providing a sample of human umbilical cord blood;
   (b) removing red cells from the sample to obtain mononuclear cells;
   (c) culturing the mononuclear cells in a culture medium in a non-tissue culture treated culture vessel having a hydrophobic surface with a net positive charge for a sufficient time to obtain a cell population negative for CD14 and positive for CD45 and CD 117, which is attached to the culture vessel and essentially free from mesenchymal stem cells and monocytes, wherein the cell culture does not require a cell feeder;
   and optionally further comprising
   (d) detaching the cells from the culture vessel by lidocaine EDTA detachment of cells and, optionally, subsequently digestion with trypsin EDTA.

2. The method of claim 1, further comprising incubating the attached cells with EDTA solution or EDTA solution containing trypsin wherein the EDTA is from about 0.5 mM to about 2.5 mM and the trypsin is from about 0.05% to about 0.25%.

3. A method of harvesting embryonic-like stem cells from umbilical cord blood, comprising:
   extracting umbilical cord blood comprising mononuclear cells;
   culturing the mononuclear cells in growth medium on a hydrophobic surface with a net positive charge for a sufficient time, such that the mononuclear cells attached to the surface are embryonic-like stem cells that are negative for CD14, positive for CD45 and CD117, and essentially free from mesenchymal stem cells and monocytes;
   isolating the embryonic-like stem cells by lidocaine EDTA detachment of cells and, optionally, subsequently digestion with trypsin EDTA, wherein the isolated stem cells are negative for CD14, positive for CD45 and CD117, and essentially free from mesenchymal stem cells and monocytes.

4. The method of claim 3, wherein the surface is selected from the group consisting of polystyrene and glass.

5. The method of claim 3, wherein the step of isolating the embryonic-like stem cells comprises isolating the cells attached to the surface.

6. The method of claim 3, wherein the step of isolating the embryonic-like stem cells further comprises selecting cells that have a positive marker for Octamer binding transcription factor 4 (Oct-4), Nanog homeobox (Nanog), and SRY (sex determining region Y)-box 2 (Sox-2); a negative marker for CD3, CD20, CD11c, CD11b/Mac-1, and CD34.

7. The method of claim 6, wherein the step of isolating the embryonic-like stem cells further comprises selecting cells that have a positive marker for activated leukocyte cell adhesion molecule (ALCAM), complement component 5a receptor 1 (C5AR1), CD37, CD63, CD74, colony stimulating factor 1 receptor (CSF1R), integrin alpha 3, and myosin heavy chain 9 (non-muscle).

8. The method of claim 3, wherein the step of isolating the embryonic-like stem cells further comprises isolating a substantially homogeneous population of embryonic-like stem cells.

9. The method of claim 3, wherein the growth medium comprises RPMI 1640 medium and fetal bovine serum.

10. The method of claim 3, wherein the step of extracting peripheral blood further comprises removing red cells from umbilical cord blood to obtain mononuclear cells.

11. The method of claim 1, wherein the embryonic-like stem cells are characterized by:
(a) displaying embryonic stem cell characteristics;
(b) displaying hematopoietic cell characteristics by being positive for hematopoietic stem cell marker CD45 and CD117;
(c) phenotypically distinct from lymphocytes, macrophages and monocytes by being negative for CD14;
(d) phenotypically distinct from hematopoietic stem cells;
(e) displaying low immunogenicity; and
(f) displaying immune regulation;
wherein the embryonic-like stem cells are capable of proliferation and are able to differentiate to multiple types of cells.

12. The method of claim 11, wherein the embryonic stem cell characteristics are characterized by positive phenotypes for stem cell markers Oct-4 and Nanog.

13. The method of claim 11, wherein the embryonic-like stem cells are phenotypically distinct from lymphocytes, macrophages and monocytes by being negative for CD3, CD20, CD14 and CD11b/Mac-1 markers.

14. The method of claim 11, wherein the embryonic-like stem cells are phenotypically distinct from hematopoietic stem cells by being negative for CD 34 marker.

15. The method of claim 11, wherein the low immunogenicity is characterized by substantially normal lymphocyte proliferation upon mixture of the stem cells with allogeneic lymphocytes.

16. The method of claim 11, wherein the immune regulation is characterized by inhibitory effects of the stem cells on T lymphocyte proliferation or by regulation of T cell subsets.

17. The method of claim 11, wherein the embryonic-like stem cells are capable of differentiating into at least one cell type selected from the group of endothelial-like cells, neuronal-like cells, insulin-producing cells, oligodendrocytes and megakaryocytes.

18. The method of claim 11, wherein the embryonic-like stem cells are capable of doubling about every 3 days.

19. The method of claim 11, wherein the embryonic-like stem cells are used for manufacturing a composition, wherein the composition comprises the embryonic-like stem cells and is administrated to a patient for treating Parkinson's disease, diabetes, spinal cord damage, multiple sclerosis (MS) cardiovascular disease, stroke, birth defects or hyperglycemia.

20. The method of claim 3, wherein the isolated embryonic-like stem cell comprises:
a positive marker for at least one of Oct-4, Nanog, and Sox-2;
a positive marker for CD45 and CD117;
a negative marker for at least one of CD3, CD20, CD11c, and CD11b/Mac-1;
a negative marker for CD14;
a negative marker for CD 90; and
a negative marker for CD 34.

21. The method of claim 20, wherein the isolated embryonic-like stem cell is capable of differentiating into insulin-producing cells.

22. The method of claim 21, wherein the insulin-producing cells expresses at least one insulin gene transcription factor.

23. The method of claim 21, wherein at least one insulin gene transcription factor is selected from the group consisting of leucine zipper MafA, Pdx-1 (pancreatic duodenal homeobox factor 1), NeuroD1 (neurogenic differentiation 1), HNF6 (hepatocyte nuclear factor 6), Nkx6.1 (Nk homeobox gene), and Nkx2.2.

24. The method of claim 21, wherein the isolated embryonic-like stem cell further comprises at least one of the following embryonic genes selected from the group consisting of Zinc finger protein 206 (ZNF206), Zic family member 3 heterotaxy 1 (ZIC3), Zic family member 2 (ZIC2), Growth associated protein 43 (GAP43), PR domain containing 14 (PRDM14), Protein tyrosine phosphatase, receptor-type, Z polypeptide 1 (PTPRZ1), Podocalyxin-like (PODXL), and Zinc finger protein 589 (ZNF589).

25. The method of claim 21, wherein the isolated embryonic-like stem cell further comprises at least one positive marker selected from the group consisting of activated leukocyte cell adhesion molecule (ALCAM), complement component 5a receptor 1 (C5AR1), CD37, CD63, CD74, colony stimulating factor 1 receptor (CSF1R), integrin alpha 3, and myosin heavy chain 9 (non-muscle).

* * * * *